US006951713B2

(12) United States Patent
Hei et al.

(10) Patent No.: US 6,951,713 B2
(45) Date of Patent: Oct. 4, 2005

(54) ABSORBING PATHOGEN-INACTIVATING COMPOUNDS WITH POROUS PARTICLES IMMOBILIZED IN A MATRIX

(75) Inventors: Derek J. Hei, Concord, CA (US); Michael S. Clarke, San Francisco, CA (US)

(73) Assignee: Cerus Corporation, Concord, CA (US)

( * ) Notice: Subject to any disclaimer, the term of this patent is extended or adjusted under 35 U.S.C. 154(b) by 0 days.

(21) Appl. No.: 10/016,323

(22) Filed: Dec. 10, 2001

(65) Prior Publication Data

US 2005/0142542 A1 Jun. 30, 2005

Related U.S. Application Data

(63) Continuation of application No. 09/112,068, filed on Jul. 8, 1998, now abandoned, which is a continuation-in-part of application No. 09/003,113, filed on Jan. 6, 1998, now abandoned, which is a continuation of application No. 08/779,885, filed on Jan. 6, 1997, now abandoned, which is a continuation of application No. 08/779,830, filed on Jan. 6, 1997, now abandoned.

(51) Int. Cl.[7] .................. A01N 1/02; A61K 35/14; C12N 7/06; C12M 1/00; C07K 1/00
(52) U.S. Cl. .................. 435/2; 424/529; 435/238; 435/283.1; 530/412; 530/413; 530/415
(58) Field of Search .................. 435/2, 180, 238, 435/283.1; 530/412, 413, 415; 424/529

(56) References Cited

U.S. PATENT DOCUMENTS

| 3,238,056 | A | 3/1966 | Pall et al. .................. 117/98 |
| 3,729,457 | A | 4/1973 | Davankov et al. ......... 525/332.2 |
| 3,975,481 | A | 8/1976 | Baumgaertner ............. 264/126 |
| 4,064,042 | A | 12/1977 | Kunin ........................ 210/692 |
| 4,110,391 | A | 8/1978 | Berzen et al. .............. 264/120 |
| 4,160,059 | A | 7/1979 | Samejima .................. 131/342 |
| 4,202,775 | A | 5/1980 | Abe et al. ................... 210/287 |
| 4,309,247 | A | 1/1982 | Hou et al. .................. 162/149 |
| 4,390,619 | A | 6/1983 | Harmening-Pittiglio ......... 435/2 |
| 4,460,530 | A | 7/1984 | Hanson et al. ............. 264/121 |
| 4,576,715 | A | 3/1986 | Michaels et al. ........... 201/347 |
| 4,594,202 | A | 6/1986 | Pall et al. ...................... 264/8 |
| 4,664,683 | A | 5/1987 | Degen et al. ................. 55/387 |
| 4,684,521 | A | 8/1987 | Edelson ....................... 424/529 |
| 4,693,981 | A | 9/1987 | Wiesehahn et al. ......... 435/238 |
| 4,727,027 | A | 2/1988 | Wiesehahn et al. ...... 435/173.2 |
| 4,728,432 | A | 3/1988 | Sugiyama et al. .......... 210/646 |
| 4,748,120 | A | 5/1988 | Wiesehahn ............... 435/173.3 |
| 4,777,069 | A | 10/1988 | Cederberg et al. .......... 428/113 |
| 4,880,843 | A | 11/1989 | Stein ........................... 521/98 |
| 4,925,880 | A | 5/1990 | Stein ........................... 521/98 |
| 4,935,141 | A | 6/1990 | Buck et al. ............. 210/500.38 |
| 4,943,373 | A | 7/1990 | Onishi et al. ........... 210/500.72 |
| 4,959,148 | A | 9/1990 | Clark, III .................... 210/635 |
| 4,985,153 | A | 1/1991 | Kuroda et al. .............. 210/782 |
| 5,019,311 | A | 5/1991 | Koslow ....................... 264/122 |
| 5,030,352 | A | 7/1991 | Varady et al. ........... 210/502.1 |
| 5,037,857 | A | 8/1991 | Maroldo et al. .............. 521/29 |
| 5,094,960 | A | 3/1992 | Bonomo ..................... 436/178 |
| 5,100,564 | A | 3/1992 | Pall et al. .................... 210/782 |
| 5,128,048 | A | 7/1992 | Stewart et al. .............. 210/749 |
| 5,137,926 | A | 8/1992 | Maroldo et al. .............. 521/29 |
| 5,147,722 | A | 9/1992 | Koslow ....................... 428/402 |
| 5,190,657 | A | 3/1993 | Heagle et al. .............. 210/645 |
| 5,234,608 | A | 8/1993 | Duff ........................... 210/806 |
| 5,269,917 | A | 12/1993 | Stankowski ................. 210/232 |
| 5,279,742 | A | 1/1994 | Markell et al. ............. 210/638 |
| 5,288,605 | A | 2/1994 | Lin et al. ........................ 435/2 |
| 5,328,758 | A | 7/1994 | Markell et al. ............... 442/35 |
| 5,354,262 | A | 10/1994 | Boehringer et al. ............ 604/4 |
| 5,407,581 | A | 4/1995 | Onodera et al. ............ 210/654 |
| 5,418,130 | A | 5/1995 | Platz et al. .................... 435/2 |
| 5,455,040 | A | 10/1995 | Marchant .................... 424/426 |
| 5,456,845 | A | 10/1995 | Nishimura et al. ......... 210/782 |
| 5,459,030 | A | 10/1995 | Lin et al. ........................ 435/2 |
| 5,468,536 | A | 11/1995 | Whitcomb et al. ........... 428/98 |
| 5,482,828 | A | 1/1996 | Lin et al. ........................ 435/2 |
| 5,486,293 | A | 1/1996 | Boschetti et al. ........... 210/635 |
| 5,486,410 | A | 1/1996 | Groeger et al. ............. 442/353 |
| 5,501,795 | A | 3/1996 | Pall et al. .................... 210/508 |
| 5,504,163 | A | 4/1996 | Tegen et al. ............. 525/332.2 |

(Continued)

FOREIGN PATENT DOCUMENTS

AU 6339190 4/1991

(Continued)

OTHER PUBLICATIONS

English Translation of PCT Application PCT/DE90/00691.

(Continued)

Primary Examiner—David M. Naff
(74) Attorney, Agent, or Firm—Morrison & Foerster LLP

(57) ABSTRACT

Methods and devices are provided for reducing the concentration of low molecular weight compounds in a biological composition, while substantially maintaining a desired biological activity of the biological composition. The device comprises highly porous adsorbent particles, and the adsorbent particles are immobilized by an inert matrix. The matrix containing the particles is contained in a housing, and the particles range in diameter from about 1 μm to about 200 μm. The matrix can be fibrous, and the particles can have a surface area greater than 750 m$^2$/g and a pore diameter between about 25 and 800 Å. The device can be used to adsorb and remove a pathogen-inactivating compound that is a nucleic acid-binding compound such as psoralen, an acridine derivative or a dye from a biological composition such as a blood product.

45 Claims, 15 Drawing Sheets

U.S. PATENT DOCUMENTS

| | | | |
|---|---|---|---|
| 5,531,902 A | 7/1996 | Gallup | 210/673 |
| 5,543,062 A | 8/1996 | Nishimura | 210/782 |
| 5,556,541 A | 9/1996 | Ruschke | 210/232 |
| 5,559,250 A | 9/1996 | Cook et al. | 549/282 |
| 5,571,666 A | 11/1996 | Floyd et al. | 435/2 |
| 5,593,823 A | 1/1997 | Wollowitz et al. | 435/2 |
| 5,605,746 A | 2/1997 | Groeger et al. | 442/347 |
| 5,607,766 A | 3/1997 | Berger | 428/373 |
| 5,616,254 A | 4/1997 | Pall et al. | 210/806 |
| 5,639,376 A | 6/1997 | Lee et al. | 210/645 |
| 5,660,731 A | 8/1997 | Piechocki et al. | 210/669 |
| 5,662,728 A | 9/1997 | Groeger | 96/153 |
| 5,773,384 A | 6/1998 | Davankov et al. | 502/402 |
| 5,817,354 A | 10/1998 | Mozaffar et al. | 424/271 |
| 5,871,900 A | 2/1999 | Wollowitz et al. | 435/2 |
| 5,882,517 A | 3/1999 | Chen et al. | 210/496 |
| 5,883,256 A | 3/1999 | Schuler et al. | 546/102 |
| 6,228,995 B1 | 5/2001 | Lee | 530/412 |
| 6,294,361 B1 * | 9/2001 | Horowitz et al. | 435/173.3 |
| 6,319,662 B1 | 11/2001 | Foley et al. | 435/2 |
| 6,348,309 B1 | 2/2002 | Mohr et al. | 435/2 |
| 6,544,727 B1 | 4/2003 | Hei | 435/2 |
| 2002/0045228 A1 | 4/2002 | Hei | 435/2 |
| 2002/0094568 A1 | 7/2002 | Hei | 435/2 |
| 2002/0115585 A1 | 8/2002 | Hei | 435/2 |
| 2002/0192632 A1 | 12/2002 | Hei et al. | 514/1 |
| 2004/0185544 A9 | 9/2004 | Hei | |
| 2004/0185553 A9 | 9/2004 | Hei | |

FOREIGN PATENT DOCUMENTS

| | | |
|---|---|---|
| CA | 2065842 | 12/1999 |
| DE | 27 21 511 | 11/1977 |
| DE | 249 274 A1 | 9/1987 |
| DE | 3819000 | 12/1989 |
| EP | 099 586 A2 | 7/1983 |
| EP | 230 247 | 7/1987 |
| EP | 0 366 946 | 5/1990 |
| EP | 0 776 668 A2 | 10/1996 |
| JP | 62-283198 | 12/1987 |
| JP | 03-229610 | 10/1991 |
| WO | WO 83/00023 | 1/1983 |
| WO | WO 91/03933 | 4/1991 |
| WO | WO 94/11556 | 5/1994 |
| WO | WO 94/27433 | 12/1994 |
| WO | WO 95/00631 | 1/1995 |
| WO | WO 95/18665 | 7/1995 |
| WO | WO 96/39818 | 12/1996 |
| WO | WO 96/40857 | 12/1996 |
| WO | WO 97/18844 | 5/1997 |
| WO | WO 97/37536 | 10/1997 |
| WO | WO 98/30327 | 7/1998 |
| WO | WO 99/34914 | 7/1999 |
| WO | WO 99/34915 | 7/1999 |
| WO | WO 99/37340 | 7/1999 |

OTHER PUBLICATIONS

510(k) Notification submitted to the U.S. Food & Drug Administration, Asahi Medical Co., Ltd., Tokyo, Japan (Dec. 5, 1988).

Andrade, J.D., et al., "Coated adsorbents for direct blood perfusion: Hema/activated carbon", vol. XVII Trans. Amer. Soc. Artf. Int. Organs pp. 222-228 (1971).

Artuc et al. "Reversible binding of 5- and 8-methoxypsoralen to human serum proteins (albumin) and to epidermis in vitro" Brit. J. Derm. 101:669-677 (1979).

Bertolini, F. et al., "Platelet concentrates stored in synthetic medium after filtration," Vox Sang 67:82-86 (1992).

Bock, M., et al., "White cell depletion of single-donor platelet preparations by a new adsorption filter," Transfusion 31:333-334 (1991).

Bogusz M. et al. "Isolation of drugs from blood and tissues with XAD-2 bags" Forensic Sci. Int'l. 12:73-82 (1978).

Boomgaard, M.N. et al., "In vitro evaluation of platelet concentrates, prepared from pooled buffy coats, stored for 8 days after filtration", Transfusion 34:311-316 (1994).

Brettel T.A., and Saferstein, R., "Forensic science" Anal. Chem., 59:162-174 (1987).

Carmen R. "The selection of plastic materials for blood bags" Trnas. Med. Rev. 7:1 1-10 (1993).

Chandy, T., and Sharma, C.P., "Polylysine-immoblilized chitosan beads as adsorbents for bilitubin," Artificial Organs 16:568-576 (1992).

Chaplin, H. et al. "Frozen storage of 11 units of sickle cell red cells for autologous transfusion of a single patient" Transfusion vol. 26:4 pp. 341-345 (1986).

Coli L. et al. "Phosphate removal by resin hemoperfusion efficacy and biocompatibility of a new exchange" Biomat. Art Cells & Immob. Biotech., 20:1153-1163 (1992).

Courtney, J.M., et al., "Monitoring of the blood response in blood purification," Artificial Organs 17:260-266 (1993).

Cruse, J.M. and Lewis, R.E. *Illustrated Dictionary of Immunology*, CRC Press (1995) p. 37.

Davankov, V.A., and Tsyurupa, M.P., "Structure and properties of hypercrosslinked polystyrene-the first representative of a new class of polymer networks," *Reactive Polymers* 13 Elsevier Science Pub. B.V., Amsterdam pp. 27-42 (1990).

Denti, E. et al. (Jul.-Aug. 1977) "Evaluation of novel sorbent systems for joint hemodialysis and hemoperfusion" Med. Instrument. 11(4):212-214.

Dodd et al. (1991) "Inactivation of Viruses in Platelet Suspensions that Retain Their In Vitro Characteristics: Comparison of Psoralen-ultraviolet A and Merocyanine 540 Visible Light Methods," Transfusion 31:483-490.

Dunlop, E.H. and Williams, R., "Physico-chemical aspects of the removal of protein-bound substances by charcoal and other adsorbents of potential value in systems of artificial liver support: Part 2- Kinetics of removal," Med. & Biol. Eng. & Comput., 16:350-362 (1978).

Dunlop, E.H., and Williams, R., "Physico-chemical aspects of the removal of protein-bound substances by charcoal and other adsorbents of potential value in systems of artificial liver support: Part I—Equilibrium properties," Med. & Biol. Eng. & Comput., 16:343-49(1978).

Dvilansky et al. "Evaluation of a new polyacrolein microsphere (acrobead) protein A column: An in vitro study using the blood of patients with immune thrombocytopenia of malignancies" Transfusion 32:210-214 (1992).

Faenza et al. "Hemoperfusion with a new anion exchange resin corrects the metabolic alkalosis in pyloric stenosis: An experimental demonstration" Int'l. J. Art. Organs 15:677-680 (1992).

Fini M. et al. "In vitro evaluation of heparin adsorption during haemoperfusion with Dowex 1×2 anion exchange resin" Art. Cells. Blood Subs. And Immob Biotech 23:1 101-108 (1995).

Goodrich R.P. et al. "Selective inactivation of viruses in the presence of human platelets: UV sensitization with psoralen derivatives" Proc. Nat'l. Acad. Sci. USA 91:5552-5556 (1994).

Hanson (1992) "Photochemical Inactivation of Viruses with Psoralens: An Overview," Blood Cells: 18:7-25.

Hei, D.J., et al., "Removal of cytokines from HSA-containing solutions by adsorption onto silica," Biotech. Bioeng., 44:1023-1030 (1994).

Heinmets et al. "Inactivation of viruses in plasma by photosensitized oxidation" Joint report with the Naval Medical Res. Institute, Walter Reed Army Institute of Research 53-55 pp. 1-16 (1955).

Horowitz, B., et al., "Inactivation of viruses in labile blood derivatives," Transfusion 25:516-522 (1985).

Hughes, R., et al. Albumin-coated amberlite XAD-7 resin for hemoperfusion in acute liver failure Part II: In vivo evaluation. . Artifical Organs (1979):3(1):23-26.

Ibrahim, G., et al., "Application of Amerlite XAD-2 resin for general toxicological analysis," J. Chrom., 108:107-116 (1975).

Ishihara, K., et al., "Selective adhesion of platelets on a polyion complex composed of phospholipid polymers containing sulfonate groups and quartenary ammonium groups," J.Biomed. Mat. Res., 28:1347-1355 (1994).

Joustra-Dijkhuis, A.M., Effect of filtration on subsequently stored platelet concentrates,: Vox Sang 67:22-27 (1994).

Kambic, H. et al. (1983) "Historical perspective therapeutic applications and new frontiers" In *Plasmaphereis* 2nd 3d., Intern. Center for Artific. Organs and Transplantation: Cleveland OH, pp. 75-78.

Kao, K.J., et al., "White cell reduction in platelet concentrates and packed red cells by filtration: a multicenter clinical trial," Transfusion 35:13-19 (1995).

Kiremitci & Piskin "Properties of new sorbents containing activated carbon-PHEMA-PEG" Int'l J. of Art. Org. 8:4 201-208 (1985).

Klein H.G., ed. *Standards for Blood Banks and Transufions Services*, 185h ed., Bethesdada, MD: Amer. Assoc. of Bld Bnk (1997) 14-17.

Kril and Fung, "Influence of hydrophobicity on the Ion exchange selectivity coefficients for aromatic amines" J. Pharm Sci., 79:440-443 (1990).

Lee, C.J., and Hsu, S.T., "Preparation of spherical encapsulation of activated carbons and their adsorption capacity of typical uremic toxins," J. Biomed. Mat. Res., 24:243-258 (1990).

Lin, et al., "Use of 8-Methoxypsoralen and Long-Wavelength Ultraviolet Radiation for Decontamination of Platelet Concentrates," Blood 74:517-525 (1989).

Lunn, G., et al., "Removal of biological stains from aqueous solution using a flow-through decontamination procedure", Biotech. & Histochem vol. 69 No. 1 pp. 45-54 (1994).

Malchesky P. et al. (1977) "Membranes containing sorbents for blood detoxification" Trans. Am. Soc. Artif. Intern. Organs. 659-664.

Malchesky P. et al. (1978) "Sorbent membranes: Device designs, evaluations and potential applications" *Artifical Organs* 2 (4):367-371.

Margolis-Nunno, H., et al., "Elimination of potential mutagenicity in platelet concentrates that are virally inactivated with psoralens and ultraviolet A light", Transfusion 35:855-62 (1995).

Matsuda, K., et al., "Experimental study on the adsorption of excess heparin with anion exchange resin fiber," Artificial Organs 13:504-507 (1989).

Miletic and Popovic "Complement activation in stored platelet concentrates" Transfusion (1993) 33:150-154.

Morel, et al., "Photochemical Inactivation of Viruses and Bacteriophage in Plasma and Plasma Fractions," Blood Cells 18:27-42 (1992).

Moroff et al. (1992) "Factors influencing virus inactivation and retention of platelet properties following treatment with aminomethyltrimethylpsoralen and ultraviolet A light" 18: 43-56.

Murphy, S., et al., "In vitro assessment of the quality of stored platelet concentrates", Transfusion Med. Rev. VIII (1):29-36 (1994).

Murugavel, S., "In vitro studies of the efficacy of reversed phase silica gel as a sorbent for hemo- and plasmaperfusion" Clin. Tox. 30:69 (1992).

Nathan et al. "A novel agarose acrobeads protein A column for selective immunoadsorbance of whole blood: Performance, specifiticity and safety" Biomat. Art. Cells & Immob. Biotech 20:23-30 (1992).

Nolan. A.P., et al., "Endotoxin binding by charged and uncharged resins (38895)," Proc. Soc. Exp. Biol. & Med., 149:766-770 (1979).

Pardue, K.J., and Merrill, D.J., Literature applications for Amberlite®/Duolite® Anion exchange resins, literature survey, 1987-1991, p. 1-b 48, Supelco, Inc. (1992).

Pegues et al. "The removal of 13C labeled endotoxin by activated charcoal" Intl. J. Art. Organs 2:153-158 (1979).

Purolite Technical Bulletin entitled "Hypersol-Macronet™ Sorbent Resins," The Purolyte Co. (PA), pp. 1-11 (1995).

Rodriguez, F., *Principles of Polymer Systems*, Hemisphere Publishing Corp., pp. 449-453 (3rd ed. 1989).

Rosenbaum, J., et al. Resin hemoperfusion for acute drug intoxication. Arch Intern Med 1976; 136:263-266.

Schmidt et al. "Ion-exchange preconcentration and group separation of ionic and neutral organic compounds" *J. Chromatog.* (1993) 640:145-149.

Sergeyev, V.P., et al., "Comparative evaluation of the structure and properties of certain granulated and fibrous activated carboniferous sorbents," Biomart., Art, Cells, Art. Org., 17:353-361 (1989).

Shimazaki K. "Changes of pore and adorption capacity of polyacrylonitrile-based activated carbon fiber (PAN-ACF) in activation" Nippon Kagaku Kaishi 1:54-61 (1993).

Shimizu, T. et al., "Filtration through a polyester white cell-reduction filter of plasma-poor platelet concentrates prepared with an acetate-containing additive solution," Transfusion 33:730-734 (1993).

Shimizu, T., et al., "Adsorption of anaphylatoxins and platelet-specific proteins by filtration of platelet concentrates with a polyester leukocyte reduction filter," Vox Sang 66: 161-165 (1994).

Sintov, A., et al. "Cross-linked chondroitin sulphate: characterization for drug delivery purposes", Biomaterials vol. 16 No. 6 pp. 473-478 (1995).

Snezhkova et al. "DNA-coated adsorbents experimental assessment and results of severe psoriasis treatment" Biomat. Art Cells & Immob. Biotech 20:1201-1221 (1992).

Sun and Fritz "Chemically modified polymeric resins for high-performance liquid chromatography" J. Chrom. 522: 95-105 (1990).

Sweeney, J.D., et al., "White cell-reduced platelet concentrates prepared by in-line filtration of platelet-rich plasma," Transfusion 35:131-136 (1995).

Tang et al. "Free and glycosidically bound volatile compounds in fresh celery (Apium graveolens L.)" J. Agr. Food Chem. 38:1937-1940 (1990).

Tijssen, J.et al. (1979) "A hemoperfusion column based on activated carbon granules coated with an ultrathin membrane of cellulose acetate" *Artificial Organs* 3(1):11-14.

Tishler & Winston "Sorbent therapy of the porphyrias III. Comparative efficacy of experimental plasma perfusion with several commercial hemoperfusion cartridges" Meth. & Find Exptl. Clin. Pharmacol 6:7 389-393 (1984).

Ton et al. "Albumin-coated amberlite XAD-7 resin for hemoperfusion in acute liver failure—Part I: Adsorption studies" Artificial Organs 3:20-22 (1979).

Tsyurupa, M.P. et al., "Sorption of organic compounds from aqueous media by hypercrosslinked polystyrene sorbents 'Styrosorb'", Reactive Polymers 25:69-78 (1995).

Valeri Capt. C.R. et al. "Freeze-preserved baboon red blood cells: effects of biochemical modification and perfusion in vitro", Am J Vet Res, 42:1590-1594 (1981).

Valerio, F., et al. "Adsorption properties of U.I.C.C. Rhodesian chrysotile and crocidolite in aqueous solution—effects of cation depletion", AIHA Journal (40) pp. 781-788 (1979).

van Marwijk, M. et al., "Filtration: A method to prepare white cell-poor platelet concentrates with optimal preservation of platelet viability," Transfusion 30:34-38 (1990).

Verhoeven, M., et al., "A first screening for hemocapatibility of a universal support for selective and specific hemoperfusion," Intl. J. Artificial Organs 12:63-67 (1989).

Wadenvik, H., et al., "Leukocyte removal filtration of platelet concentrates. A study of platelet loss using in-labeled platelets and dynamic gamma camera scintigraphy," Eur. J. Haematol., 47:192-96 (1991).

Webb, D., "Charcoal haemoperfusion in drug intoxication," British J. of Hosp. Med. 49(7)493-496.

Yoshioka, T. and Shimamura, M. "Studies of polystyrene-based Ion exchange fiber. I The preparation and fundamental characteristics of polystyrene-based Ion exchange fiber", The Chem. Soc. of Japan vol. 56, No. 12 pp. 3726-3729 (1983).

Heddle, N.M. (1995). "Febrile Nonhemolytic Transfusion Reactions to Platelets," Curr. Opin. Hematology 2:478-483.

* cited by examiner

5-[(β-carboxyethyl) amino] acridine

Acridine

Acridine Orange

9-Amino Acridine

ABSORBING PATHOGEN-INACTIVATING COMPOUNDS WITH POROUS PARTICLES IMMOBILIZED IN A MATRIX

CROSS-REFERENCE TO RELATED APPLICATIONS

This application is a continuation application of application Ser. No. 09/112,068, filed Jul. 8, 1998, now abandoned, which is a continuation-in-part application of application Ser. No. 09/003,113, filed Jan. 6, 1998, now abandoned, which is a continuation of application Ser. No. 08/779,885 and of Ser. No. 08/779,830, each of which was filed on Jan. 6, 1997, each of which is now abandoned. Application Ser. No. 09/112,068 and 09/003,113 are each incorporated by reference in their entirety.

TECHNICAL FIELD

The present invention relates to methods and devices for the reduction of compounds from biological compositions. The compounds have a molecular weight ranging from about 100 g/mol to about 30,000 g/mol.

BACKGROUND ART

An extensive body of research exists regarding the removal of substances from blood products. The bulk of this research is directed at white cell reduction. See, e.g., M. N. Boomgaard et al., *Transfusion* 34:311 (1994); F. Bertolini et al., *Vox Sang* 62:82 (1992); and A. M. Joustra-Dijkhuis et al., *Vox Sang* 67:22 (1994). Filtration of platelets is the most common method used in white cell reduction of platelet concentrates. See, e.g., M. Böck et al., *Transfusion* 31:333 (1991) (Sepacell PL-5A, Asahi, Tokyo, Japan); J. D. Sweeney et al., *Transfusion* 35:131 (1995) (Leukotrap PL, Miles Inc., Covina, Calif.); and M. van Marwijk et al., *Transfusion* 30:34 (1990) (Cellselect, NPBI, Emmer-Compascuum, The Netherlands; Immugard Ig-500, Terumo, Tokyo, Japan). These current filtration mechanisms, however are not amenable for the removal of relatively low molecular weight compounds including for example psoralens, psoralen photoproducts and other compounds commonly used in treating biological fluids.

The process of adsorption has been used to isolate selective blood components onto phospholipid polymers. For example, several copolymers with various electrical charges have been evaluated for their interactions with blood components, including platelet adhesion and protein adsorption. K. Ishihara et al.,*J. Biomed. Mat. Res.* 28:1347 (1994). Such polymers, however, are not designed for the adsorption of low molecular weight compounds.

Various dialysis means are able to remove low molecular weight compounds from plasma and whole blood. For example, dialysis can successfully remove low molecular weight toxins and pharmaceutical compounds. Thus, dialysis might be used to remove, for example, psoralens and psoralen photoproducts from blood products. Unfortunately, current dialysis procedures involve very complicated and expensive devices. As such, the use of dialysis machines would not be practical for the decontamination of a large volume of blood products.

The use of polystyrene divinylbenzene, silica gel, and acrylester polymers for the adsorption of methylene blue has previously been described. For example, PCT Publication No. WO 91/03933 describes batch studies with free adsorbent resin (e.g., Amberlites (Rohm and Haas (Frankfurt, Germany) and Bio Beads (Bio-Rad Laboratories (Munich, Germany)). Without very careful removal of the adsorbent resins after exposure to the blood product, however, these methods create the risk of transfusion of the resin particles.

In addition, devices and processes for the removal of leukocytes and viral inactivation agents (e.g., psoralens, hypericin, and dyes such as methylene blue, toluidine blue, and crystal violet) have also been disclosed. Specifically, PCT Publication No. WO 95/18665 describes a filter comprising a laid textile web which includes a mechanically stable polymeric substrate. The web itself comprises interlocked textile fibers forming a matrix with spaces and fibrillated particles disposed within the spaces. However, this device causes a significant decrease in the Factor XI activity.

Simpler, safer and more economical means for reducing the concentration of low molecular weight compounds in a biological composition while substantially maintaining the biological activity of the treated composition are therefore needed.

DISCLOSURE OF THE INVENTION

Devices are provided for reduction of concentration of compounds from biological compositions. The compounds have molecular weights ranging from about 100 g/mol to about 30,000 g/mol. The device is a flow device. An example of a flow device is shown in FIG. 12. Flow devices are known in the literature and are described, for example, in PCT publication WO 96/40857, incorporated by reference herein. Flow devices permit reduction of concentration of low molecular weight compounds from materials such as blood products by perfusing the blood product through the flow device.

Exemplary compounds include pathogen inactivating compounds, dyes, thiols, plasticizers and activated complement. Devices are provided that comprise a three dimensional network of adsorbent particles immobilized by an inert matrix. This immobilization reduces the risk of leakage of loose adsorbent particles into the blood product. Furthermore, immobilization of the adsorbent particles by an inert matrix simplifies manufacturing by reducing problems associated with handling loose adsorbent particles.

The present invention provides a device for substantially reducing the concentration of a low molecular weight compound in a biological composition. In one embodiment, the device comprises an inert matrix containing a highly adsorbent material, wherein the highly adsorbent material ranges from about 1 $\mu$m to about 200 $\mu$m in diameter. The biological composition treated with the device maintains suitable biological activity. The device is for use in a flow process.

In another embodiment, the adsorbent material has a length less than three times the width.

In another embodiment, the particulate adsorbent material is synthetic and polymeric, and the adsorbent particles possess superior wetting properties.

In another embodiment, the adsorbent particles comprise a hypercrosslinked polystyrene network.

In another embodiment, the particulate adsorbent is carbonaceous.

In another embodiment, the carbonaceous particulate adsorbent is activated carbon.

In another embodiment, the activated carbon particulate adsorbent has a surface area greater than about 950 $m^2/g$.

In another embodiment, the activated carbon particulate adsorbent has a surface area greater than about 1200 $m^2/g$.

In another embodiment, the carbonaceous particulate adsorbent is formed by steam activation.

In another embodiment, the carbonaceous particulate adsorbent is formed from coconut shells.

In another embodiment, the particle containing matrix is at least 3 mm thick.

In another embodiment, the particle containing matrix is composed of a plurality of layers.

In another embodiment, the device, or a component of the device, has been treated to enhance functionality, and the enhanced functionality is biocompatibility, hemocompatibility or wettability.

In another embodiment, a component of the device has been treated to enhance functionality, and the component is the adsorption media.

In another embodiment, a component of the device has been treated to enhance functionality, and the component is the adsorbent material.

In another embodiment, a component of the device has been treated to enhance functionality, and the component is the inert matrix.

In another embodiment, the treatment to enhance functionality is a surface treatment.

In another embodiment, the low molecular weight compound is an acridine derivative, a psoralen derivative or a dye.

In another embodiment, the acridine derivative is N-(9-acridinyl)-β-alanine.

In another embodiment, the low molecular weight compound is a psoralen derivative, and wherein the psoralen derivative is 4'(4-amino-2-oxa)butyl-4,5',8-trimethyl psoralen.

In another embodiment, the low molecular weight compound is a biological response modifier.

In another embodiment, the biological response modifier is activated complement.

In another embodiment, the low molecular weight compound is a quencher.

In another embodiment, the low molecular weight compound is glutathione.

In another embodiment, the low molecular weight compound is methylene blue.

In another embodiment, the treated biological composition is suitable for infusion into a human.

In another embodiment, the biological composition is plasma.

In another embodiment, the inert matrix is a fiber network.

In another embodiment, the fiber network is composed of cellulose.

In another embodiment, the adsorbent comprises activated carbon, and wherein the particle containing matrix is at least 3 mm thick.

In another embodiment, the fiber network is composed of cellulose. The adsorbent comprises activated carbon formed by steam activation of coconut shells. The adsorption media is at least 3 mm thick. Examples of low molecular weight compounds reduced by the device include, without limitation, acridine derivatives, psoralen derivatives, dyes and biological response modifiers such as activated complement. Where the low molecular weight compound is a biological response modifier, for example, the treated biological composition is suitable for infusion into a human.

In another embodiment, the biological composition is plasma.

In another embodiment, the inert matrix is a particulate network.

In another embodiment, the adsorbent material comprises particulate hypercrosslinked polystyrene networks, and the particle containing matrix is at least 3 mm thick.

In another embodiment, the inert matrix is a particulate network. The adsorbent material comprises particulate hypercrosslinked polystyrene networks formed by sintering together particles of ultra-high molecular weight polyethylene with particulate hypercrosslinked polystyrene networks. The particle containing matrix is at least 3 mm thick. Examples of low molecular weight compounds reduced by the device include, without limitation, acridine derivatives, psoralen derivatives, dyes and biological response modifiers such as activated complement. Where the low molecular weight compound is a biological response modifier, for example, the treated biological composition is suitable for infusion into a human. A nonlimiting example of the biological composition is plasma.

The present invention also provides methods of reducing the concentration of a low molecular weight compound in a biological composition, wherein the biological composition treated with the device substantially maintains suitable biological activity. The method comprises treating the biological composition with a device.

In one embodiment, the device comprises an inert matrix containing a highly adsorbent material, wherein the highly adsorbent material ranges from about 1 $\mu$m to about 200 $\mu$m in diameter. The biological composition treated with the device maintains suitable biological activity. The device is useful in a flow process.

In another embodiment, the device comprises an inert matrix containing a highly adsorbent material, wherein the highly adsorbent material ranges from about 1 $\mu$m to about 200 $\mu$m in diameter. The biological composition treated with the device maintains suitable biological activity. The device is useful in a flow process. The inert matrix is a fiber network. The fiber network is composed of cellulose. The adsorbent comprises activated carbon formed by steam activation of coconut shells. The particle containing matrix is at least 3 mm thick.

In another embodiment, the device comprises an inert matrix containing a highly adsorbent material, wherein the highly adsorbent material ranges from about 1 $\mu$m to about 200 $\mu$m in diameter. The biological composition treated with the device maintains suitable biological activity. The device is useful in a flow process. The inert matrix is a particulate network. The adsorbent material comprises particulate hypercrosslinked polystyrene networks formed by sintering together particles of ultra-high molecular weight polyethylene with particulate hypercrosslinked polystyrene networks. The particle containing matrix is at least 3 mm thick.

In another embodiment, the biological composition is plasma.

In another embodiment, the biological composition treated with the device is suitable for infusion into a human.

In another embodiment, the biological composition flows through the device as a result of a pressure differential.

In another embodiment, the pressure differential arises due to a hydrostatic head.

In another embodiment, the pressure differential arises due to the use of a pump.

In another embodiment, the biological composition flows through the device at a flux between about 0.1 mL/cm2/min and about 10 mL/cm$^2$/min.

In another embodiment, the biological composition flows through the device at a flux between about 0.2 mL/cm2/min and about 5 mL/cm$^2$/min.

The present invention also provides a biological composition, wherein the biological composition is suitable for infusion. The biological composition is produced by treating a biological composition with a device.

In one embodiment, the device comprises an inert matrix containing a highly adsorbent material, wherein the highly adsorbent material ranges from about 1 μm to about 200 μm in diameter. The biological composition treated with the device maintains suitable biological activity. The device is useful in a flow process.

In another embodiment, the device comprises an inert matrix containing a highly adsorbent material, wherein the highly adsorbent material ranges from about 1 μm to about 200 μm in diameter. The biological composition treated with the device maintains suitable biological activity. The device is useful in a flow process. The inert matrix is a fiber network. The fiber network is composed of cellulose. The adsorbent comprises activated carbon formed by steam activation of coconut shells. The adsorption media is at least 3 mm thick.

In another embodiment, the device comprises an inert matrix containing a highly adsorbent material, wherein the highly adsorbent material ranges from about 1 μm to about 200 μm in diameter. The biological composition treated with the device maintains suitable biological activity. The device is useful in a flow process. The inert matrix is a particulate network. The adsorbent material comprises particulate hypercrosslinked polystyrene networks formed by sintering together particles of ultra-high molecular weight polyethylene with particulate hypercrosslinked polystyrene networks. The particle containing matrix is at least 3 mm thick.

In another embodiment, the biological composition comprises plasma.

In another embodiment, a nucleic acid targeting compound was added to the biological composition prior to treatment with the device.

In another embodiment, a psoralen derivative was added to the biological composition prior to treatment with the device.

In another embodiment, an acridine derivative was added to the biological composition prior to treatment with the device.

In another embodiment, methylene blue was added to the biological composition prior to treatment with the device.

The present invention also provides a device for reducing the concentration of small organic compounds in a blood product while substantially maintaining a desired biological activity of the blood product.

In one embodiment, the device comprises highly porous adsorbent particles that are immobilized by an inert matrix.

BEST MODE FOR CARRYING OUT THE INVENTION

Figure 12:
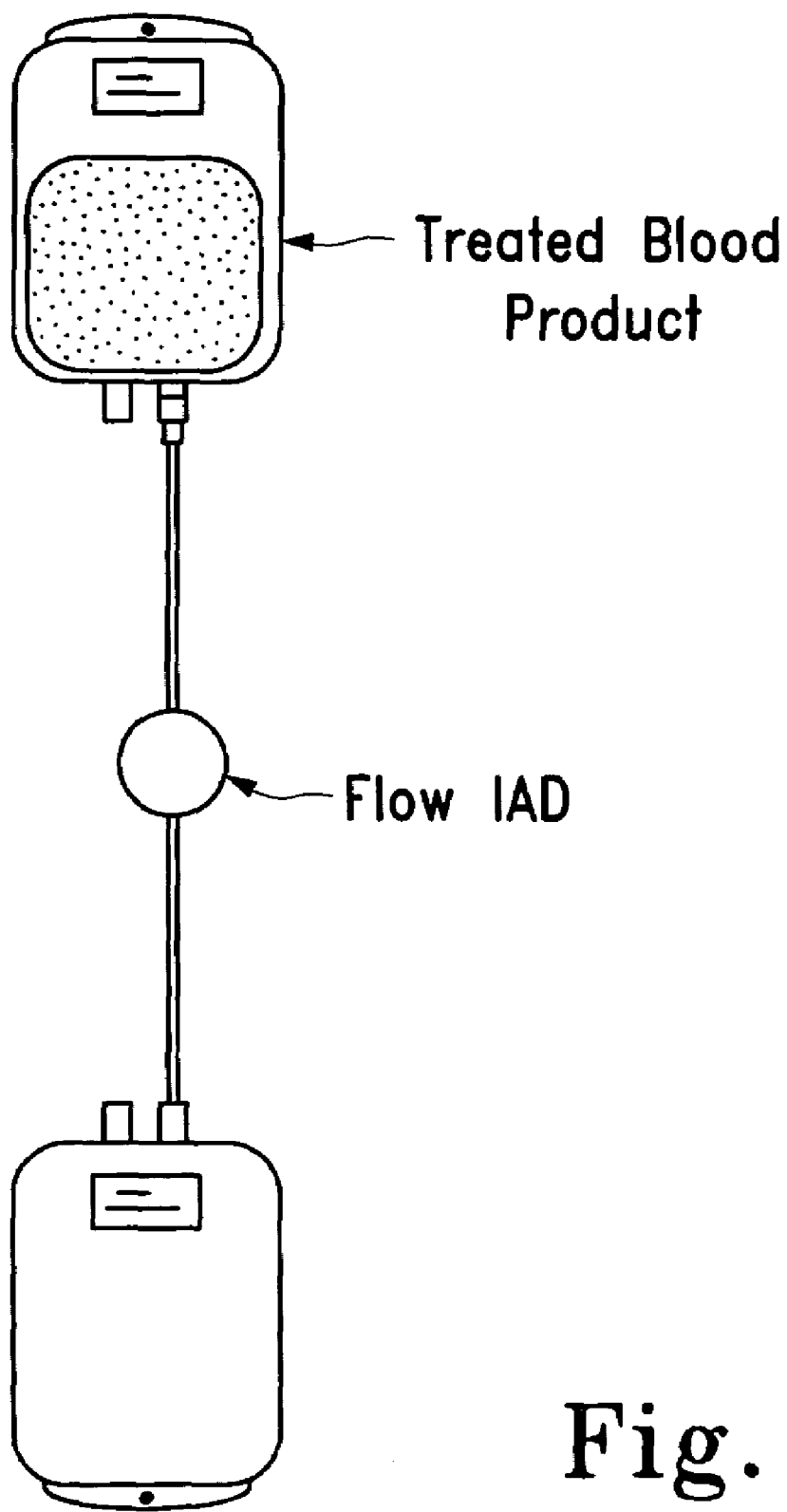
FIG. 12 is an illustration of a flow configuration for the immobilized adsorption device (IAD).

Devices are provided for reduction of concentration of compounds from biological compositions. The compounds have molecular weights ranging from about 100 g/mol to about 30,000 g/mol. The device is a flow device. An example of a flow device is shown in FIG. 12. Flow devices are known in the literature and are described, for example, in PCT publication WO 96/40857, incorporated by reference herein. Flow devices permit reduction of concentration of low molecular weight compounds from materials such as blood products by perfusing the blood product through the flow device.

Exemplary compounds include pathogen inactivating compounds, dyes, thiols, plasticizers and activated complement. Devices are provided that comprise a three dimensional network of adsorbent particles immobilized by an inert matrix. This immobilization reduces the risk of leakage of loose adsorbent particles into the blood product. Furthermore, immobilization of the adsorbent particles by an inert matrix simplifies manufacturing by reducing problems associated with handling loose adsorbent particles.

Definitions

Figure 11:
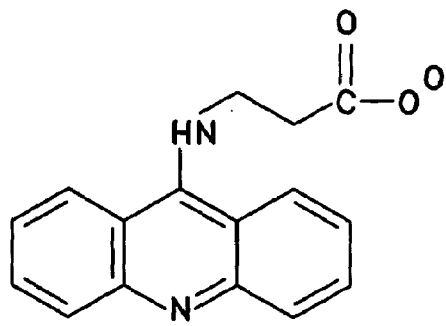
FIG. 11 depicts the chemical structures of acridine, acridine orange, 9-amino acridine, and 5-[(β-carboxyethyl)amino]acridine.
Figure 11:
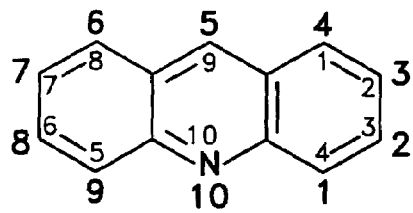
Figure 11:
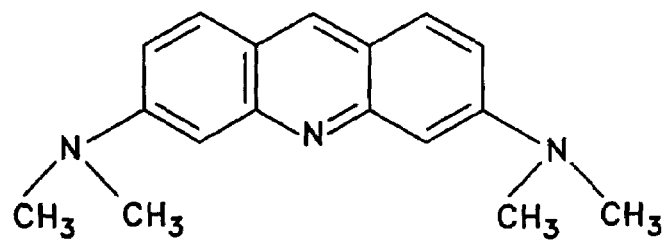
Figure 11:
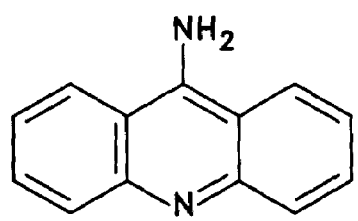

The term "acridine derivatives" refer to a chemical compound containing the tricyclic structure of acridine (dibenzo[b,e]pyridine; 10-azanthracene). The compounds have an affinity for (and can bind) to nucleic acids non-covalently through intercalation. The term "aminoacridine" refers to those acridine compounds with one or more nitrogen-containing functional groups. Examples of aminoacridines include 9-amino acridine and acridine orange (depicted in FIG. 11).

The term "adsorbent particle" broadly refers to any natural or synthetic material which is capable of interacting with molecules in a liquid thus allowing the molecule to be removed from the liquid. Examples of naturally occurring adsorbents include but are not limited to activated carbon, silica, diatomaceous earth, and cellulose. Examples of synthetic adsorbents include but are not limited to polystyrene, polyacrylics, and carbonaceous adsorbents. Adsorbent particles are often porous, often possess high surface areas, and may be modified with a variety of functional groups (e.g. ionic, hydrophobic, acidic, basic) which can effect how the adsorbent interacts with molecules.

The term "aromatic," "aromatic compounds," and the like refer broadly to compounds with rings of atoms having delocalized electrons. The monocyclic compound benzene ($C_6H_6$) is a common aromatic compound. However, electron delocalization can occur over more than one adjacent ring (e.g., naphthalene (two rings) and anthracene (three rings)). Different classes of aromatic compounds include, but are not limited to, aromatic halides (aryl halides), aromatic heterocyclic compounds, aromatic hydrocarbons (arenes), and aromatic nitro compounds (aryl nitro compounds).

The term "biocompatible coating" refers broadly to the covering of a surface (e.g., the surface of a polystyrene bead) with a hydrophilic polymer that when in contact with a blood product does not result in an injurious, toxic, or immunological response and renders the surface more biocompatible by decreasing cell adhesion, protein adsorption or improves cell function. Suitable coatings are biocompatible if they have minimal, if any, effect on the biological material to be exposed to them. By "minimal" effect it is meant that no significant biological difference is seen compared to the control. In preferred embodiments, biocompatible coatings improve the surface hemocompatibility of polymeric structures. For example, poly(2-hydroxyethyl methacrylate) (pHEMA) is frequently used for the coating of materials used in medical devices (e.g., blood filters).

The term "biocompatible housing" refers broadly to filter housings, containers, bags, vessels, receptacles, and the like that are suitable for containing a biological material, such as plasma. Suitable containers are biocompatible if they have minimal, if any, effect on the biological material to be contained therein. By "minimal" effect it is meant that no significant biological difference is seen in blood product function compared to the control as described herein, for example, for plasma. Thus, biological compositions may be stored in biocompatible housings prior to transfusion to a recipient.

The term "biological fluids" include human or non-human whole blood, plasma, platelets, red blood cells, leukocytes, serum, lymph, saliva, milk, urine, or products derived from or containing any of the above, alone or in mixture, with or without a chemical additive solution. Preferably, the fluid is blood or a blood product with or without a chemical additive solution, most preferably plasma.

The term "blood bag" refers to a blood product container.

The term "blood product" refers to the fluid and/or associated cellular elements and the like (such as erythrocytes, leukocytes, platelets, etc.) that pass through the body's circulatory system; blood products include, but are not limited to, blood cells, platelet mixtures, serum, and plasma. The term "platelet mixture" refers to one type of blood product wherein the cellular element is primarily or only platelets. A platelet concentrate (PC) is one type of platelet mixture where the platelets are associated with a smaller than normal portion of plasma. In blood products synthetic media may make up that volume normally occupied by plasma; for example, a platelet concentrate may entail platelets suspended in 35% plasma/65% synthetic media. Frequently, the synthetic media comprises phosphate.

The term "blood separation means" refers broadly to a device, machine, or the like that is able to separate blood into blood products (e.g., platelets and plasma). An apheresis system is one type of blood separation means. Apheresis systems generally comprise a blood separation device, an intricate network of tubing and filters, collection bags, an anticoagulant, and a computerized means of controlling all of the components.

The term "crosslinked" refers broadly to linear molecules that are attached to each other to form a two- or three-dimensional network. For example, divinylbenzene (DVB) serves as the crosslinking agent in the formation of styrene-divinylbenzene copolymers. The term also encompasses "hypercrosslinking" in which hypercrosslinked networks are produced by crosslinking linear polystyrene chains either in solution or in a swollen state with bifunctional agents. A variety of bifunctional agents can be used for cross-linking (for example, see Davankov and Tsyurupa, Reactive Polymers 13:24–42 (1990); Tsyurupa et al., Reactive Polymers 25:69–78 (1995).

The term "cyclic compounds" refers to compounds having one (i.e., a monocyclic compounds) or more than one (i.e., polycyclic compounds) ring of atoms. The term is not limited to compounds with rings containing a particular number of atoms. While most cyclic compounds contain rings with five or six atoms, rings with other numbers of atoms (e.g., three or four atoms) are also contemplated by the present invention. The identity of the atoms in the rings is not limited, though the atoms are usually predominantly carbon atoms. Generally speaking, the rings of polycyclic compounds are adjacent to one another; however, the term "polycyclic" compound includes those compounds containing multiple rings that are not adjacent to each other.

The term "dye" refers broadly to compounds that impart color. Dyes generally comprise chromophore and auxochrome groups attached to one or more cyclic compounds. The color is due to the chromophore, while the dying affinities are due to the auxochrome. Dyes have been grouped into many categories, including the azin dyes (e.g., neutral red, safranin, and azocarmine B); the azo dyes; the azocarmine dyes; the dephenymethane dyes; the fluorescein dyes; the ketonimine dyes; the rosanilin dyes; the triphenylmethane dyes; the phthalocyanines; and, hypericin. It is contemplated that the methods and devices of the present invention may be practiced in conjunction with any dye that is a cyclic compound.

The term "fiberized resin" generally refers to immobilization of adsorbent material, including for example, resins, in, on or entrapped to a fiber network. In one embodiment, the fiber network is comprised of polymer fibers. In another embodiment, the fibers consist of a polymer core (e.g., polyethylene terephthalates [PET]) with a high melting point surrounded by a polymer sheath (e.g., nylon or modified PET) with a relatively low melting temperature. Fiberized resin may be produced by heating the fiber network, under conditions that do not adversely affect the adsorbent capacity of the resin to a significant degree. Where the resin comprises beads, heating is performed such that the adsorbent beads become attached to the outer polymer sheath to create "fiberized beads". By producing fiberized resin containing a known amount of adsorbent beads per defined area, samples of fiberized resin for use in the removal of cyclic compounds (e.g., psoralens, and, in particular, aminopsoralens) and other products can be obtained by cutting a defined area of the fiberized resin, rather than weighing the adsorbent beads.

The term "filter" refers broadly to devices, materials, and the like that are able to allow certain components of a mixture to pass through while retaining other components. For example, a filter may comprise a mesh with pores sized to allow a blood product (e.g., plasma) to pass through, while retaining other components such as resin particles. The term "filter" is not limited to the means by which certain components are retained.

The term "flow adapter" refers to a device that is capable of controlling the flow of a particular substance like a blood product. The flow adapter may perform additional functions, such as preventing the passage of pieces of adsorbent resin material.

The term "heterocyclic compounds" refers broadly to cyclic compounds wherein one or more of the rings contains more than one type of atom. In general, carbon represents the predominant atom, while the other atoms include, for example, nitrogen, sulfur, and oxygen. Examples of heterocyclic compounds include furan, pyrrole, thiophene, and pyridine.

The phrase "high temperature activation process" refers to a high temperature process that typically results in changes in surface area, porosity and surface chemistry of the treated material due to pyrolysis and/or oxidation of the starting material.

The term "immobilized adsorption device (IAD)" refers to immobilized adsorbent material in, on or entrapped to an inert matrix. Where the inert matrix is a fiber network the term IAD can be used interchangeably with the term fiberized resin.

The term "inert matrix" refers to any synthetic or naturally occurring fiber or fibrous material which can be used to immobilize adsorbent particles without substantially effecting the desired biological activity of the blood product. The matrix may contribute to the reduction in concentration of small organic compounds although typically it does not contribute substantially to the adsorption or removal process. In addition, the inert matrix may interact with cellular or protein components resulting in cell removal (e.g. leukodepletion) or removal of protein or other molecules. The matrix may undergo a surface treatment or coating to enhance functionality. For example, the matrix may get a hydrophobic coating or glow discharge treatment to increase biocompatibility, increase wettability, and/or facilitate priming.

The term "in-line column" refers to a container, usually cylindrically shaped, having an input end and an output end and containing a substance disposed therein to reduce the concentration of small organic compounds from a blood product.

The term "isolating" refers to separating a substance out of a mixture containing more than one component. For example, platelets may be separated from whole blood. The product that is isolated does not necessarily refer to the complete separation of that product from other components.

The term "macropores" generally means that the diameter of the pores is greater than about 500 Å. The term micropores refers to pores with diameters less than about 20 Å. The term mesopores refers to pores with diameters greater than about 20 Å and less than about 500 Å.

The term "macroporous" is used to describe a porous structure having a substantial number of pores with diameters greater than about 500 Å.

The term "macroreticular" is a relative term that means that the structure has a high physical porosity (i.e., a large number of pores are present) a porous adsorbent structure possessing both macropores and micropores.

The term "mesh enclosure," "mesh pouch" and the like refer to an enclosure, pouch, bag or the like manufactured to contain multiple openings. For example, the present invention contemplates a pouch, containing the immobilized adsorbent particle, with pores of a size that allow a blood product to contact the immobilized adsorbent particle, but retain the immobilized adsorbent particle within the pouch.

The term "photoproduct" refers to products that result from the photochemical reaction that a psoralen or other dye (e.g., methylene blue, phthalocyanines) undergoes upon exposure to ultraviolet radiation.

The term "polyaromatic compounds" refers to polymeric compounds containing aromatic groups in the backbone, such as polyethylene terphalate, or as pendant groups, such as polystyrene, or both.

The term "polystyrene network" refers broadly to polymers containing styrene ($C_6H_5CH=CH_2$) monomers; the polymers may be linear, consisting of a single covalent alkane chain with phenyl substituents, or cross-linked, generally with m- or p-phenylene residues or other bifunctional or hypercrosslinked structure, to form a two-dimensional polymer backbone.

The term "psoralen removal means" refers to a substance or device that is able to remove greater than about 80% of the psoralen from, e.g., a blood product; preferably, greater than about 90%; most preferably greater than about 99%. A psoralen removal means may also remove other components of the blood product, such as psoralen photoproducts.

The phrase "reducing the concentration" refers to the removal of some portion of low molecular weight compounds from a biological composition. While reduction in concentration is preferably on the order of greater than about 70%, more preferably on the order of about 90%, and most preferably on the order of about 99%.

The phrase "removing substantially all of said portion of a compound (e.g. a psoralen, psoralen derivative, isopsoralen, acridine, acridine derivative, or dye) free in solution" refers preferably to the removal of more than about 80% of the compound free in solution, more preferably to the removal of more than about 85%, even more preferably of more than about 90%, and most preferably to the removal of more than about 99%.

The term "resin" refers to a solid support (such as particles or beads etc.) capable of interacting and attaching to various small organic compounds, including psoralens, in a solution or fluid (e.g., a blood product), thereby decreasing the concentration of those elements in solution. The removal process is not limited to any particular mechanism. For example, a psoralen may be removed by hydrophobic or ionic interaction (i.e., affinity interaction). The term "adsorbent resin" refers broadly to both natural organic substances and synthetic substances and to mixtures thereof.

The term "sintered medium" refers to a structure which is formed by applying heat and pressure to a powder or mixture of powders, thereby partially fusing the powder or powder mixture, such that a path for a flowing fluid exists through the structure. The porous structure can be prepared by mixing powders of relatively low melting polymers and heating them so the plastic particles partially fuse but still allow a path for fluids to penetrate the porous mass. Sintered adsorbent media can be prepared similarly by incorporating carbon or other high or non-melting adsorbent particle with that of the low melting powder and heating. Methods of producing porous plastic materials are described in U.S. Pat. Nos. 3,975,481, 4,110,391, 4,460,530, 4,880,843 and 4,925,880, incorporated by reference herein. The process causes fusing of the powder particles resulting in the formation of a porous solid structure. The sintered medium can be formed into a variety of shapes by placing the polymeric powder in a forming tool during the sintering process. Adsorbent particles can be introduced into the sintered medium by mixing adsorbent particles with the powdered thermoplastic polymer before subjecting to the sintering process.

The term "stabilizing agent" refers to a compound or composition capable of optimizing the adsorption capacity of certain resins. Generally speaking, acceptable stabilizing agents should be soluble in water and ethanol (or other wetting agents), nonvolatile relative to water and ethanol, and safe for transfusion in small amounts. Examples of stabilizing agents include, but are not limited to, glycerol and low molecular weight PEGs. A "wetting agent" is distinguishable from a "stabilizing agent" in that the former is believed to reopen adsorbent pores of those resins that are not hypercrosslinked (i.e., non-macronet resins). Wetting agents generally will not prevent pores from collapsing under drying conditions, whereas stabilizing agents will. A general discussion of wetting and wetting agents is set forth in U.S. Pat. No. 5,501,795 to Pall et al., hereby incorporated by reference.

The phrase "substantially maintaining a desired biological activity of the biological composition" refers to substantially maintaining properties of a biological composition which are believed to be indicative of the potential performance of the composition in a therapeutic setting. For example, in the case of plasma, in vivo activity is not destroyed or significantly lowered if the level of clotting factors, such as Factors I, II, V, VII, VIII, IX, X, XI, or the change in PT and PTT time are substantially maintained in plasma when treated by the methods described herein. For example, the change in level of clotting factors, such as Factors I, II, V, VII, VIII, IX, X, XI of the treated plasma can be less than about 20%; preferably less than about 10%. The change in PT and PTT time for the treated plasma can be, for example, less than about 3 seconds and greater than 1 second; preferably 1.5 seconds. It is further contemplated that the phrase substantially maintained for each of the properties associated with a described biological composition may also include values acceptable to those of ordinary skill in the art as described in the literature, including for example in Klein H. G., ed. Standards for Blood Banks and Transfusion Services, $17^{th}$ Ed., Bethesda, Md.: American Association of Blood Banks, 1996, incorporated by reference herein.

The term "equivalent thereto" when used in reference to a device of the present invention refers to a device that functions equivalently with respect to the maintenance of biological activity of a biological composition. For example, an "equivalent" device or matrix containing adsorbent particles is one that similarly maintains a suitable coagulation factor level.

The term "low molecular weight compound" refers to an organic or biological molecule having a molecular weight ranging from about 100 g/mol to about 30,000 g/mol. Low molecular weight compounds include, without limitation, the following compounds: small organic compounds such as psoralens, acridines or dyes; quenchers, such as glutathione; plastic extractables, such as plasticizers; biological modifiers, such as activated complement, that possess a molecular weight between about 100 g/mol and about 30,000 g/mol; and, polyamine derivatives.

The term "biological composition that is suitable for infusion" refers to a biological composition that maintains its essential biological properties (e.g. clotting function in plasma) while having sufficiently low levels of any undesired compounds (e.g. inactivation compounds, response modifiers) such that infusion provides intended function without detrimental side effects.

The term "control," as used in phrases such as "relative to control," refers to an experiment performed to study the relative effects of different conditions.

For example, where a biological composition is treated with a device, "untreated control" would refer to the biological compostion in the absence of treatment with the device. It may also refer to a comparison between two different types of devices.

The term "4'-(4-amino-2-oxa)butyl-4,5',8-trimethyl psoralen" is alternatively referred to as "S-59."

The term "N-(9-acridinyl)-β-alanine" is alternatively referred to as "5-[(β-carboxyethyl)amino] acridine." It is further alternatively referred to as "S-300."

The term "XUS-43493" is alternatively referred to as "Optipore 493."

The term "non-fibrous adsorbent material" refers to an adsorbent material composed substantially of particles that have a length, or longest dimension, less than five times their width, or narrowest dimension.

Adsorbent Particles

Provided are adsorbent particles which are useful in a device for reducing the concentration of compounds in a biological composition while substantially maintaining a desired biological activity of the biological composition. Typically, the compounds that are reduced in the biological composition have molecular weights ranging from about 100 g/mol to about 30,000 g/mol.

The adsorbent particles can be of any regular or irregular shape that lends itself to incorporation into the inert matrix but are preferably roughly spherical. The particles are greater than about 1 μm in diameter; preferably, the particles are greater than about 10 μm in diameter when using a sintered medium as the matrix for the adsorbent, more preferably, the particles are between about 50 μm and about 150 μm in diameter when using a sintered medium as the matrix. Preferably the particles are between about 1 μm and about 200 μm in diameter when using a wet laid fibrous medium as the matrix, more preferably between about 1 μm and about 50 μm when using a wet laid fibrous medium as the matrix for the adsorbent.

In one preferred embodiment the adsorbent particles are activated carbons derived either from natural or synthetic sources. Nonlimiting examples of activated carbons include; Picatiff Medicinal, which is available from PICA USA Inc. (Columbus, Ohio), Norit ROX 0.8, which is available from Norit Americas, Inc. (Atlanta, Ga.), Ambersorb 572, which is available from Rohm & Haas (Philadelphia, Pa.), and G-277, which is available from PICA (Columbus, Ohio).

Preferred activated carbons are those that are specially cleaned and/or meet United States Pharmacopoeia Standards. Moreover, activated carbons with surface areas greater than 950 m2/g are preferred and those with surface areas greater than 1200 m2/g are more preferred, as activated carbons with more surface area available to the low molecular weight compound generally show better adsorption. Activated carbons formed by steam activation tend to have more hydrophobic surfaces, so for more hydrophobic low molecular weight compounds, these steam activated carbons often have better binding capacity and these carbons are preferred. Less macroporosity confers selectivity for low molecular weight compounds over large proteins that mediate biological activity, so activated carbons with less macroporosity, for example activated carbons prepared from coconut shell are also preferred.

In one preferred embodiment the particles are Norit A Supra, which is available from Norit Americas, Inc. (Atlanta, Ga.). Norit A Supra is a USP-grade activated carbon that is formed by steam activation of coconut shell. This activated carbon has a very high total surface area (2000 m$^2$/g) and is very microporous in nature.

In another preferred embodiment, the particles can be hydrophobic resins. Nonlimiting examples of hydrophobic resins include the following polyaromatic adsorbents: Amberlite® adsorbents (e.g., Amberlite® XAD-2, XAD-4, and XAD-16), available from Rohm and Haas (Philadelphia, Pa.); Amberchrom® adsorbents available from Toso Haas (TosoHass, Montgomeryville, Pa.); Diaion®//Sepabeads® Adsorbents (e.g., Diaion® HP20), available from Mitsubishi Chemical America, Inc. (White Plains, N.Y.); Hypersol-Macronet® Sorbent Resins (e.g., Hypersol-Macronet® Sorbent Resins MN-200, MN-150 and MN-400) available from Purolite (Bala Cynwyd, Pa.); and Dowex® Adsorbents (e.g., Dowex® XUS-40323, XUS-43493, and XUS-40285), available from Dow Chemical Company (Midland, Mich.).

Preferred particles are hydrophobic resins which are polyaromatic adsorbents comprising a hypercrosslinked polystyrene network, such as Dowex® XUS-43493 (known commercially as Optipore® L493 or V493) and Purolite MN-200.

Hypercrosslinked polystyrene networks, such as Dowex® XUS-43493 and Purolite MN-200 are non-ionic macroporous and macroreticular resins. The non-ionic macroreticular and macroporous Dowex® XUS-43493 has a high affinity for psoralens, including for example, 4'-(4-amino-2-oxa)butyl-4,5',8-trimethyl psoralen, and it possesses superior wetting properties. The phrase "superior wetting properties" means that dry (i.e. essentially anhydrous) adsorbent does not need to be wet with a wetting agent (e.g., ethanol) prior to being contacted with the blood product in order for the adsorbent to effectively reduce the concentration of small organic compounds from the blood product.

Hypercrosslinked polystyrene networks, such as Dowex® XUS-43493 and Purolite MN-200 are preferably in the form of spherical particles with a diameter range of about 10 μm to about 200 μm. Adsorbent particles, including for example, Dowex® XUS-43493, preferably have extremely high internal surface areas and relatively small pores (e.g. 46 Å). The internal surface area of the particle can be from about 300 to about 1100 m$^2$/g; preferably 1100 m$^2$/g. The pores size of the particle can be greater than 25 Å and less than 800 Å; preferably from about 25 Å to about 150 Å; most preferably from about 25 Å to about 50 Å. While it is not intended that the present invention be limited to the mechanism by which reduction of small organic compounds takes place, hydrophobic interaction is believed to be the primary mechanism of adsorption. Its porous nature confers selectively on the adsorption process by allowing small molecules to access a greater proportion of the surface area relative to large molecules (i.e., proteins) and cells. Purolite® has many similar characteristics to Dowex® XUS-43493, such as high affinity for psoralens and superior wetting properties, and is also a preferred adsorbent particle.

Polystyrene particles can be classified, based on their mechanism of synthesis and physical and functional characteristics, as i) conventional networks and ii) hypercrosslinked networks. Preferred adsorbents have a high surface area, have pores that do not collapse, and do not require wetting. In addition, preferred adsorbents have low levels of extractable residual monomer, crosslinkers and other organic extractables.

The conventional networks are primarily styrene-divinylbenzene copolymers in which divinylbenzene (DVB) serves as the crosslinking agent (i.e., the agent that links linear polystyrene chains together). These polymeric networks include the "gel-type" polymers. The gel-type polymers are homogeneous, non-porous styrene-DVB copolymers obtained by copolymerization of monomers. The macroporous adsorbents represent a second class of conventional networks. They are obtained by copolymerization of monomers in the presence of diluents that precipitate the growing polystyrene chains. The polystyrene network formed by this procedure possess a relatively large internal surface area (up to hundreds of square meters per gram of polymer); Amberlite® XAD-4 is produced by such a procedure.

In contrast to the conventional networks described above, the preferred adsorbents of the present invention (e.g., Dowex® XUS-43493) are hypercrosslinked networks. These networks are produced by crosslinking linear polystyrene chains either in solution or in a swollen state with bifunctional agents; the preferred bifunctional agents produce conformationally-restricted crosslinking bridges, that are believed to prevent the pores from collapsing when the adsorbent is in an essentially anhydrous (i.e., "dry") state.

The hypercrosslinked networks are believed to possess three primary characteristics that distinguish them from the conventional networks. First, there is a low density of polymer chains because of the bridges that hold the polystyrene chains apart. As a result, the adsorbents generally have a relatively large porous surface area and pore diameter. Second, the networks are able to swell; that is, the volume of the polymer phase increases when it contacts organic molecules. Finally, the hypercrosslinked polymers are "strained" when in the dry state; that is, the rigidity of the network in the dry state prevents chain-to-chain attractions. However, the strains relax when the adsorbent is wetted, which increases the network's ability to swell in liquid media. Davankov and Tsyurupa, *Reactive Polymers* 13:27–42 (1990); Tsyurupa et al., *Reactive Polymers* 25:69–78 (1995), hereby incorporated by reference.

Several cross-linking agents have been successfully employed to produce the bridges between polystyrene chains, including p-xylene dichloride (XDC), monochlorodimethyl ether (MCDE), 1,4-bis-chloromethyldiphenyl (CMDP), 4,4'-bis-(chloromethyl)biphenyl (CMB), dimethylformal (DMF), p,p'-bis-chloromethyl- 1,4-diphenylbutane (DPB), and tris-(chloromethyl)-mesitylene (CMM). The bridges are formed between polystyrene chains by reacting one of these cross-linking agents with the styrene phenyl rings by means of a Friedel-Crafts reaction. Thus, the resulting bridges link styrene phenol rings present on two different polystyrene chains. See, e.g., U.S. Pat. No. 3,729,457, hereby incorporated by reference.

The bridges are especially important because they generally eliminate the need for a "wetting" agent. That is, the bridges prevent the pores from collapsing when the adsorbent is in an essentially anhydrous (i.e., "dry") state, and thus they do not have to be "reopened" with a wetting agent prior to the adsorbent being contacted with a blood product.

In order to prevent the pores from collapsing, conformationally-restricted bridges should be formed. Some bifunctional agents like DPB do not result in generally limited conformation; for example, DPB contains four successive methylene units that are susceptible to conformation rearrangements. Thus, DPB is not a preferred bifunctional agent for use with the present invention.

Some of the structurally-related characteristics of the above-described adsorbent particles are summarized in Table A.

TABLE A

| Resin | Chemical Nature | Mean Surface Area (m$^2$/g) | Mean Pore Diam. (Å) | Mesh Size ($\mu$m) |
|---|---|---|---|---|
| Amberlite ® Adsorbents - Rohm and Haas | | | | |
| XAD-2 | polyaromatic | 300 | 90 | 20–60 |
| XAD-4 | polyaromatic | 725 | 40 | 20–60 |
| XAD-7 | polymethacrylate | 450 | 90 | 20–60 |
| XAD-16 | polyaromatic | 800 | 100 | 20–60 |
| XAD-1180 | polyaromatic | 600 | 300 | 20–60 |
| XAD-2000 | polyaromatic | 580 | 42 | 20–60 |
| XAD-2010 | polyaromatic | 660 | 280 | 20–60 |
| Amberchrom ® Adsorbents - Toso Haas | | | | |
| CG-71m | polymethacrylate | 450–550 | 200–300 | 50–100 |
| CG-71c | polymethacrylate | 450–550 | 200–300 | 80–160 |
| CG-161m | polyaromatic | 800–950 | 110–175 | 50–100 |
| CG-161c | polyaromatic | 800–950 | 110–175 | 80–160 |
| Diaion ®//Sepabeads ® Adsorbents - Mitsubishi Chemical | | | | |
| HP20 | polyaromatic | 500 | 300–600 | 20–60 |
| SP206 | brominated styrenic | 550 | 200–800 | 20–60 |
| SP207 | brominated styrenic | 650 | 100–300 | 20–60 |
| SP850 | polyaromatic | 1000 | 50–100 | 20–60 |
| HP2MG | polymethacrylate | 500 | 200–800 | 25–50 |
| HP20SS | polyaromatic | 500 | 300–600 | 75–150 |
| SP20MS | polyaromatic | 500 | 300–600 | 50–100 |
| Dowex ® Adsorbents - Dow Chemical Company | | | | |
| XUS-40285 | functionalized | 800 | 25 | 20–50 |
| XUS-40323 | polyaromatic | 650 | 100 | 16–50 |
| XUS-43493 | polyaromatic | 1100 | 46 | 20–50 |

Processing the Adsorbent Particles

The adsorbent particles may be further processed to remove fine particles, salts, potential extractables, and endotoxin. The removal of these extractable components is typically performed by treatment with either organic solvents, steam, or supercritical fluids. Preferably the particles are sterilized.

Several companies currently sell "cleaned" (i.e., processed) versions of commercially available adsorbent particles. In addition to processing the adsorbent particles (e.g. resins), these companies test the adsorbents, and the final adsorbent is certified sterile (USP XXI), pyrogen-free (LAL), and free of detectable extractables (DVB and total organics).

Thermal processing (e.g., steam) is an effective method for processing adsorbent particles. F. Rodriguez, *Principles Of Polymer Systems*, (Hemisphere Publishing Corp.), pp. 449–53 (3rd. Ed., 1989). Supelco, Inc. (Bellefonte, Pa.) uses a non-solvent, thermal proprietary process to clean the Dowex® XUS-43493 and Amberlite adsorbents. The main advantage of using steam is that it does not add any potential extractables to the adsorbent. One big disadvantage, however, is that this process can strip water from the pores of the resin beads; effective performance of some adsorbents requires that the beads be re-wet prior to contacting the illuminated blood product.

The Use of Wetting Agents and Stabilizing Agents with Adsorbent Resins

Methods may be used for preventing drying and loss of adsorption capacity of particles, such as Amberlite® which lose some of their adsorption capacity under certain conditions (e.g., drying).

In one method, particles, materials or devices may be manufactured in a wet state which is sealed and not capable of drying. This method is associated with several important drawbacks. The shelf-life of the products could be reduced since levels of extractables from the materials could increase over time. Sterilization may be limited to a steam process because y-irradiation of wet polymers is typically not performed. Manufacturing a device that requires that a component be maintained in a wet state is, in general, more difficult than manufacturing a dry device; for example, bioburden and endotoxin may become of concern if there is a long lag time between device assembly and terminal sterilization.

A second method for preventing loss of adsorption capacity involves the use of an adsorbent which is not adversely affected by drying. As previously set forth, macroreticular adsorbents possessing highly crosslinked porous structures (e.g., Dowex® XUS-43493 and Purolite MN-200) generally do not require a wetting agent because the crosslinks prevent the pores from collapsing. Unlike Amberlite® XAD-16, these macroreticular adsorbents retain a very high proportion of their initial activity when they are dried.

In a third method, loss of adsorption capacity upon drying may be prevented by hydrating Amberlite® XAD-16 and related adsorbents (e.g., Amberlite® XAD-4) in the presence of a non-volatile wetting agent. For example, when using Amberlite® XAD-16 as the adsorbent, the adsorbent beads may partially dry prior to use during handling, sterilization, and storage. When the water content of these adsorbents drops below a critical level, a rapid loss in adsorption capacity occurs (probably due to "collapse" of the pores); thus, for optimum effectiveness, the pores have to be "reopened" with a wetting agent prior to use.

Stabilizing agents are effective in maintaining adsorption capacity near its maximum when certain adsorbent resins are subjected to drying conditions. It is believed that the use of stabilizing agents serves to prevent the adsorbent pores from collapsing.

An acceptable stabilizing agent should be soluble in water and ethanol, nonvolatile relative to ethanol and water, and safe for transfusion in small amounts. Glycerol and low molecular weight polyethylene glycol (e.g., PEG-200 and PEG-400) are examples of stabilizing agents possessing these characteristics. Glycerol has a positive hemocompatibility history. It is frequently added to blood as a cryopreservative agent in the frozen storage of red blood cell preparations. See, e.g., Chaplin et al., Transfusion 26:341–45 (1986); Valeri et al., Am. J. Vet. Res. 42(9) 1590–94 (1981). Solutions containing up to 1% glycerol are routinely transfused, and glycerol solutions are commercially available (e.g., Glyerolite 57 Solution, Fenwal Laboratories, Deerfield, Ill.). Adsorbent beads like Amberlite® XAD-16 may be stabilized in ethanol and glycerol.

Low molecular weight polyethylene glycols, commonly used as pharmaceutical bases, may also be used as stabilizing agents. PEGs are liquid and solid polymers of the general chemical formula $H(OCH_2CH_2)_nOH$, where n is greater than or equal to 4. PEG formulations are usually followed by a number that corresponds to its average molecular weight; for example, PEG-200 has a molecular weight of 200 and a molecular weight range of 190–210. PEGs are commercially available in a number of formulations (e.g., Carbowax, Poly-G, and Solbase).

Inert Matrices for Particle Immobilization

The adsorbent particles are immobilized by an inert matrix. The inert matrix can be made of fibrous or particulate, synthetic or natural polymer. The inert matrix can be sintered polymers. The inert matrix, as with the other components of the device, preferably is biocompatible and does not substantially adversely affect the biological activity of a material upon contact.

In an embodiment using synthetic fibers, the synthetic fibers are polyester fibers (Air Quality Filtration (AQF), a division of Hoechst Celanese (Charlotte, N.C.)). Other preferred examples of synthetic fibers are polyethylene or polyamide fibers. Other exemplary synthetic fibers include polyolefin, polyvinyl alcohol and polysulfone fibers.

In a preferred embodiment, the synthetic polymer fiber includes a first polymer core with a high melting point surrounded by a sheath with a lower melting temperature. The polymer core can be a polyester(polyethylene terephthalate). The sheath can be a nylon, or a modified polyester. Fibers are commercially available from Unitika (Osaka, Japan) and Hoechst Trevira GmbH & Co. (Augsberg, Germany).

For a fibrous matrix, the most preferred embodiment uses cellulose fibers. These cellulose fibers can be derived from a variety of sources, such as jute, kozu, kraft and manila hemp. Networks of synthetic or natural polymer fibers have been used to make filters as described in U.S. Pat. Nos. 4,559,145 and 5,639,376, which are herein incorporated by reference.

A sintered matrix is also a preferred embodiment. Synthetic polymers suitable for the construction of such sintered particles are high density polyethylene, ultra high molecular weight polyethylene, polypropylene, polyvinyl fluoride, polytetrafluoroethylene, nylon 6. More preferably the sintered particles are polyolefins, such as polyethylene.

Polymeric fibers such as those described above may be adsorbent resins without the attachment of adsorbent particles. Such fibers may be formed into a fiber network or may be immobilized on a fiber network of a less adsorbent fiber. Such fibers are contemplated by the present invention; such fibers preferably contain a large, porous, adsorptive surface area or other adsorptive means to facilitate reduction in the concentration of low molecular weight compounds.

Immobilization of Particles

In one embodiment, the adsorbent particles are immobilized by an inert matrix to produce an adsorption medium for reducing the concentration of small organic compounds in a material. The inert matrix can be a three dimensional network including a synthetic or natural polymer fiber network with adsorbent particles immobilized therein.

Preferably, the adsorption medium comprises small porous adsorbent particles with highly porous structures and very high internal surface areas, as described above, immobilized by the inert matrix. Preferably, when a biological material is brought into contact with the adsorption medium, the adsorption medium does not substantially adversely affect the biological activity or other properties of the material.

Figure 1:
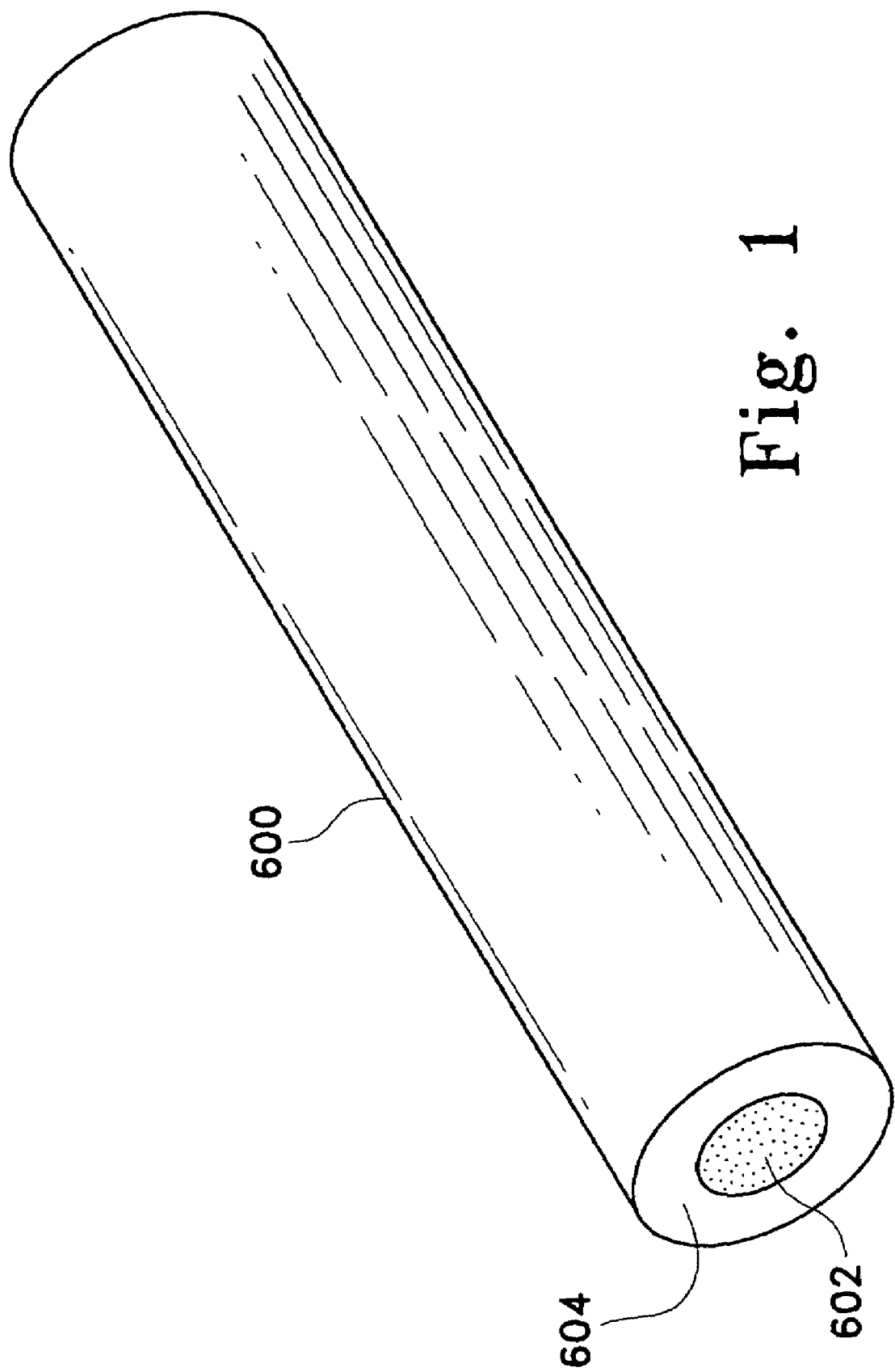
FIG. 1 diagrammatically depicts a perspective view of one embodiment of a fiber, indicating its inner core and outer sheath, that forms the fiber networks of the fiberized resin.
Figure 2:
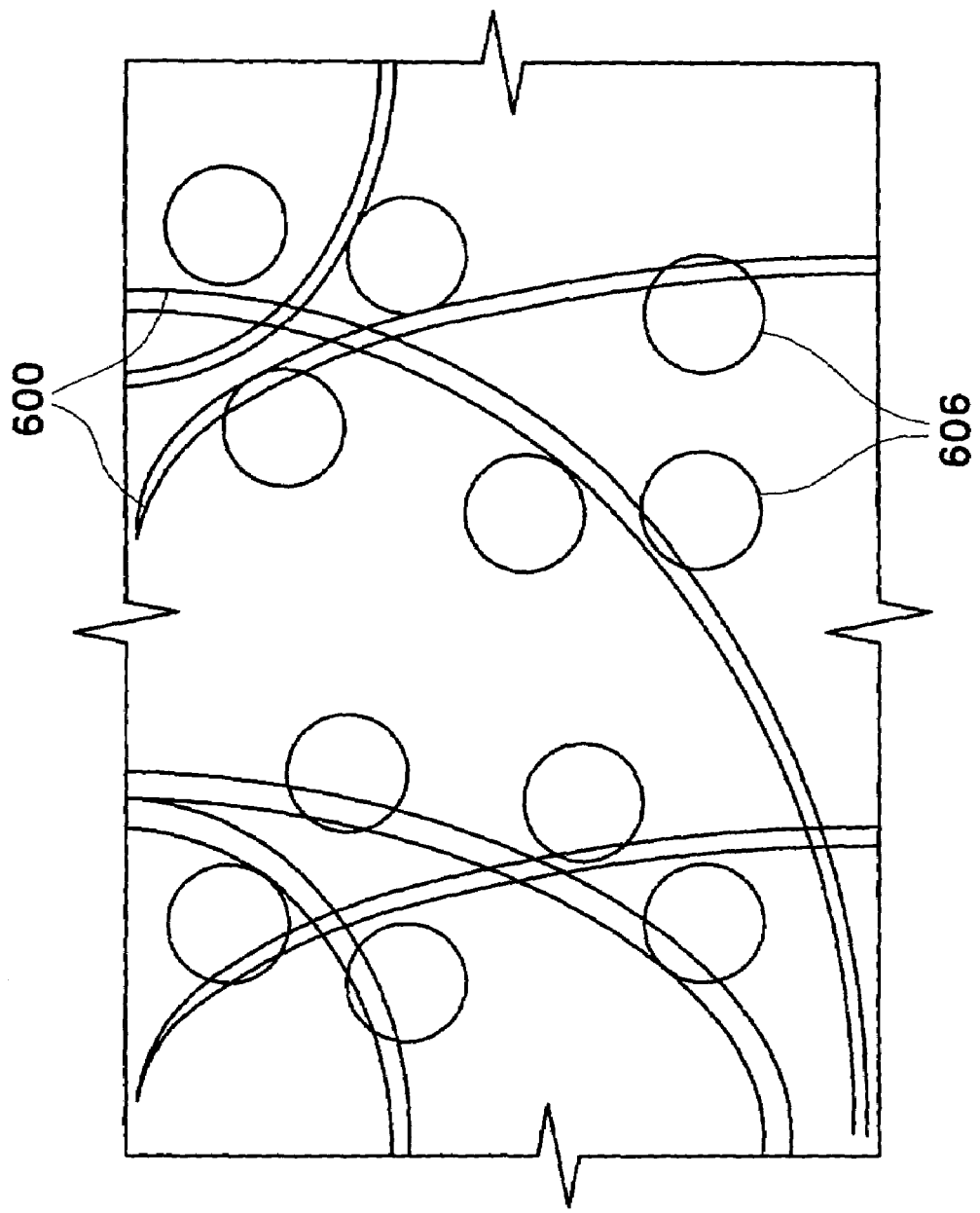
FIG. 2 schematically represents a portion of one embodiment of the fiberized resin of the present invention.
Figure 3:
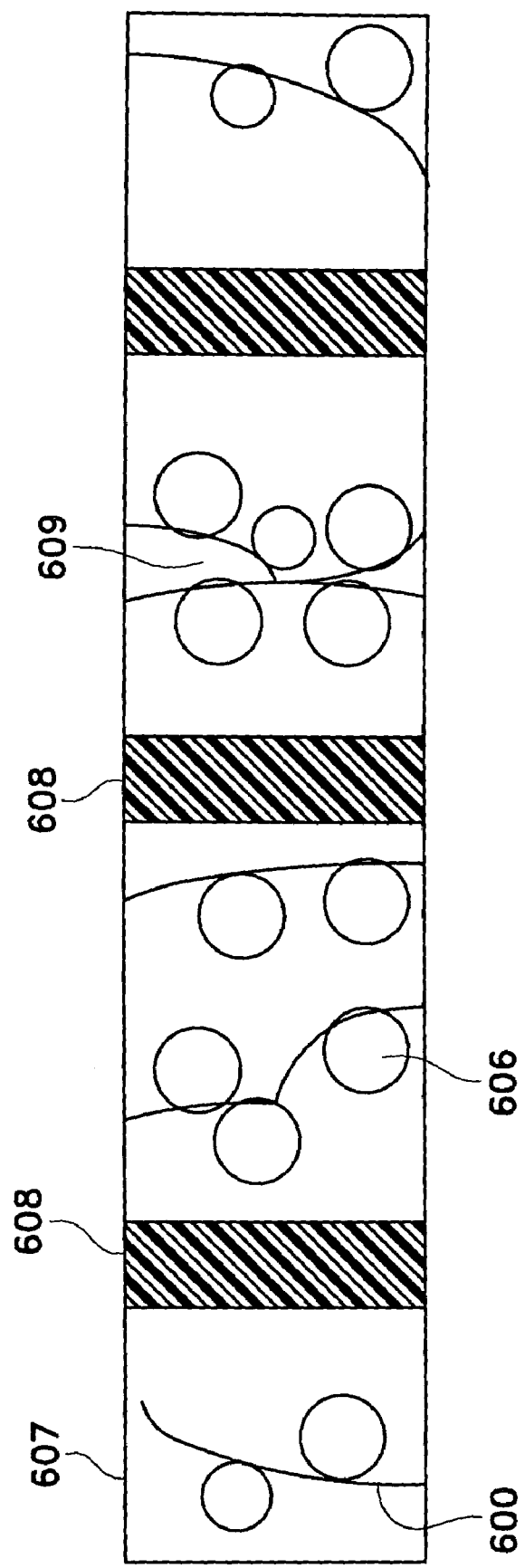
FIG. 3 diagrammatically represents a cross-sectional view of one embodiment of fiberized resin in which the adsorbent beads are secured to fibers that make up the fiberized resin.
Figure 4:
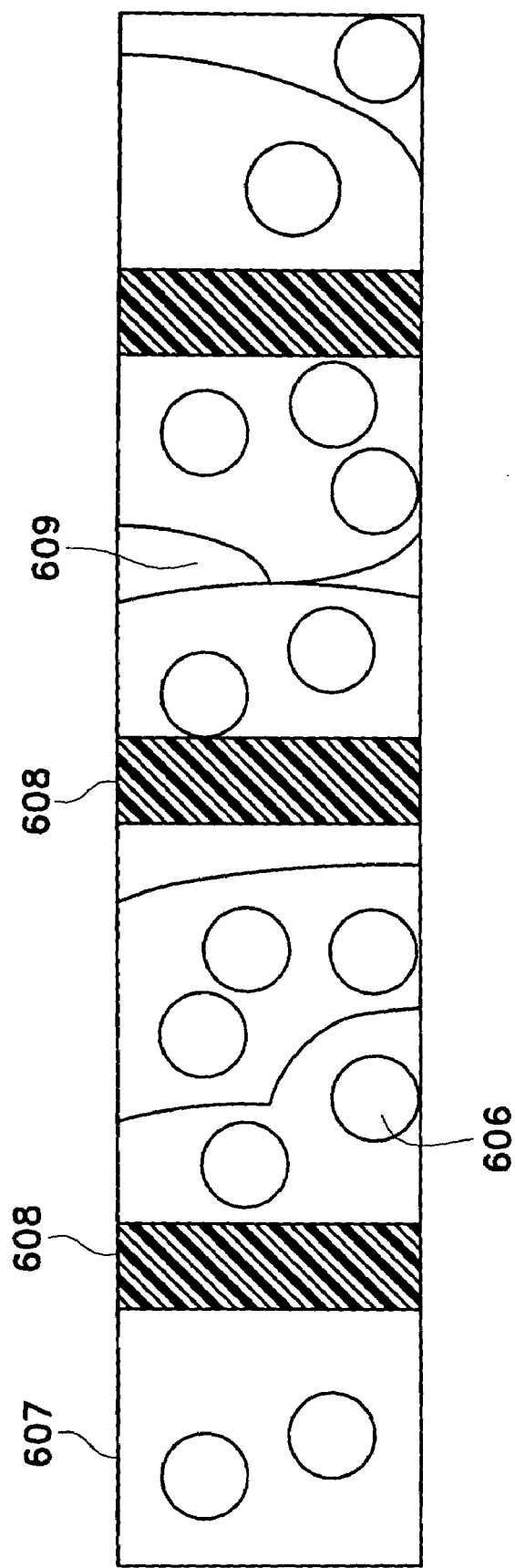
FIG. 4 diagrammatically represents a cross-sectional view of one embodiment of fiberized resin in which the adsorbent beads are immobilized within the fibers of the fiberized resin and the heat seals that encompass samples of fiberized resin.
Figure 5:
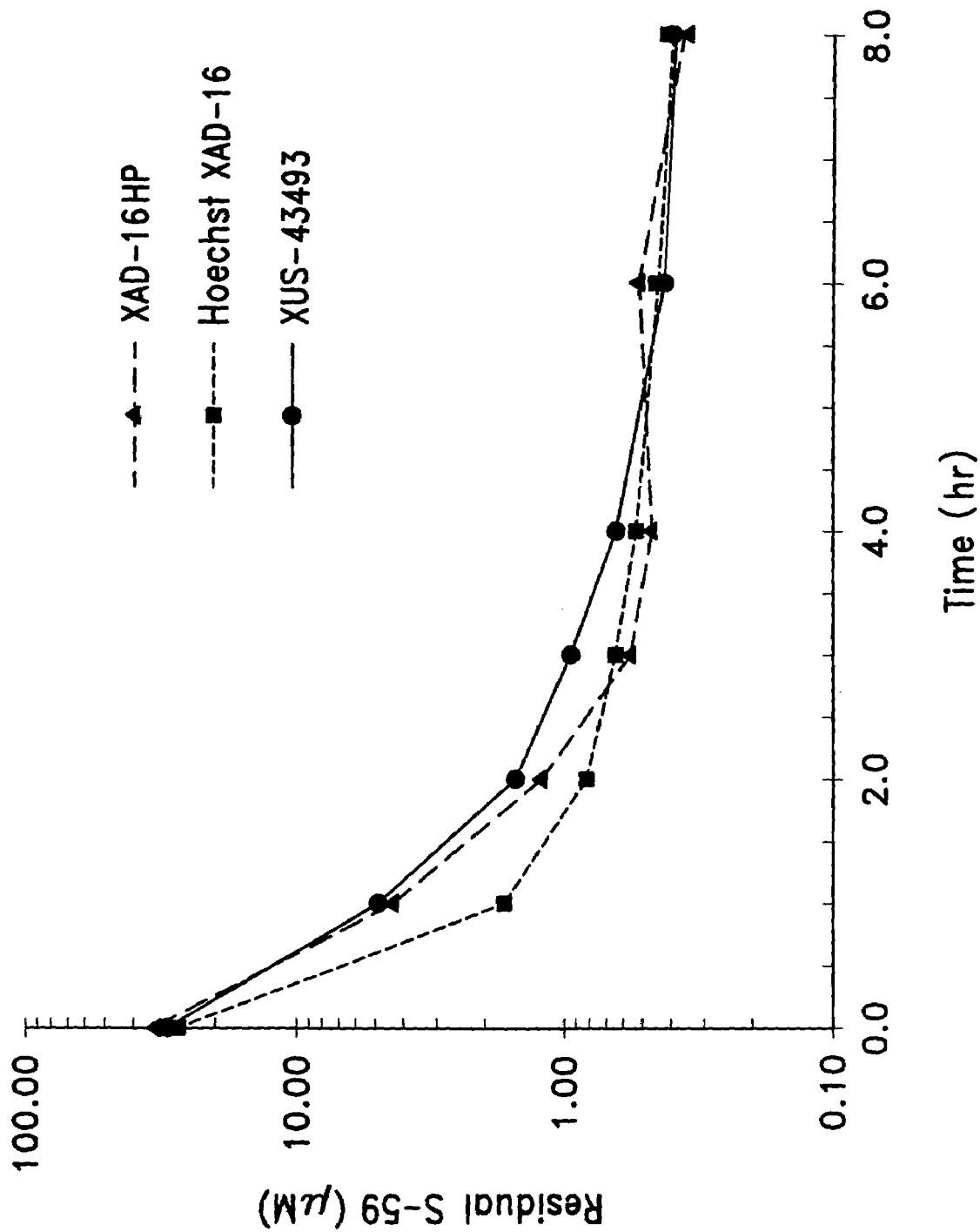
FIG. 5 is a graph showing a comparison of adsorption kinetics for removal of aminopsoralens from platelets with Dowex® XUS-43493 and Amberlite® XAD-16 HP loose adsorbent beads and fiberized resin containing Amberlite® XAD-16.
Figure 6:
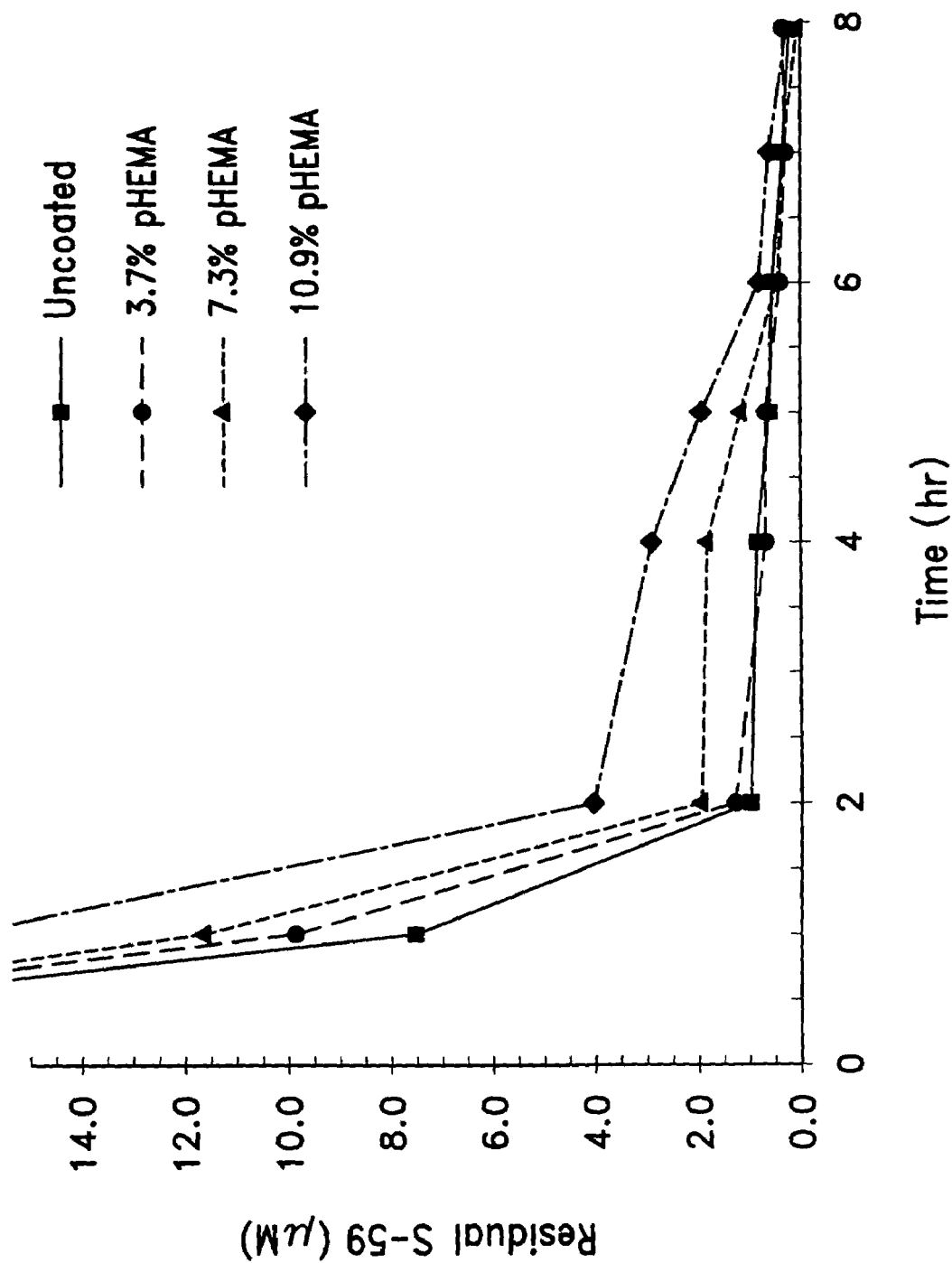
FIG. 6 is a graph showing a comparison of the adsorption kinetics for removal of aminopsoralens from platelets with p(HEMA)-coated and uncoated Dowex® XUS-43493 beads.

Technology for immobilization of adsorbent beads on a fiber network to construct air filters has been described in U.S. Pat. No. 5,486,410 and U.S. Pat. No. 5,605,746, incorporated by reference herein. As depicted in FIG. 1, the polymer fibers 600 of the fiber network consist of a polymer core 602 (e.g., polyethylene terephthalates (PET)) with a high melting point surrounded by a polymer sheath 604 (e.g., nylon) with a relatively low melting temperature. See U.S. Pat. No. 5,190,657 to Heagle et al., hereby incorporated by reference. The fiberized resin is prepared by first evenly distributing the adsorbent beads in the fiber network. Next, the network is rapidly heated (e.g., 180° C.×1 min.) causing the polymer sheath of the fibers 600 to melt and bond to the adsorbent beads 606 and other fibers, forming a cross-linked fiber network, represented in FIG. 2. As depicted in FIG. 3 and FIG. 4 (not to scale), generally speaking, the fiber networks contain three layers; two outer layers 607 that are densely packed with fibers 600 and a less dense inner layer 609 that contains the adsorbent beads 606 and fewer fibers 600. In a preferred embodiment, the edges of the fiberized resin may be sealed with polyurethane or other polymers. Alternatively, as depicted in FIG. 3 and FIG. 4, heat seals 608 may be made in the resulting fiberized resin at predetermined intervals; for example, heat seals can be made in the fiberized resin in a pattern of squares. Thereafter, the fiberized resin can be cut through the heat seals to form samples of resin containing a desired mass (e.g., preferably less than 5.0 g and more preferably less than 3.0 g) of adsorbent beads and of a size suitable for placement within a blood product container. The heat seals serve to prevent the cut fiberized resin from fraying and help to immobilize the adsorbent beads. However, the use of such heat seals is not required in order to practice the present invention. In an alternative embodiment, depicted in FIG. 4, the adsorbent beads 606 are not secured to the fibers themselves, but rather are immobilized between the denser outer layers 607 of fibers and with the heat seals 608; this embodiment may also result in samples of fiberized media containing a defined amount of adsorbent after being cut through the heat seals.

The present invention also contemplates the use of an adhesive (e.g., a bonding agent) to secure the adsorbent resin to the fibers. Moreover, while it is preferable that the adsorbent beads be chemically attached to the fiber network, the beads may also be physically trapped within the fiber network; this might be accomplished, for example, by surrounding the beads with enough fibers so as to hold the beads in position.

Other ways that the adsorbent particles may be immobilized in a fiber network are also contemplated. The particles can be immobilized using a dry-laid process, as described in U.S. Pat. Nos. 5,605,746 and 5,486,410 (AQF patents), which are herein incorporated by reference. The particles can be immobilized using a wet-laid process, as described in U.S. Pat. Nos. 4,559,145 and 4,309,247, which are herein incorporated by reference. The particles can be immobilized using a melt-blown process, as described in U.S. Pat. No. 5,616,254, which is herein incorporated by reference. Where a wet-laid process is used to construct a matrix from natural polymer fibers, the inert matrix preferably includes a binding agent to bond the adsorbent particles to the fibers. Nonlimiting examples of binding agents include melamine, polyamines and polyamides. The matrix typically contains 1% or less of such binding agents.

Where the inert matrix is constructed from particles of synthetic polymers which are sintered with adsorbent particles, it is important that the adsorbent particle have a higher melting temperature than the matrix.

In a preferred embodiment, the adsorbent particles are immobilized in a fiber matrix that is formed by thermal bonding of a biocomponent fiber network. An alternative embodiment involves immobilizing adsorbent particles in non-biocomponent fibers and using a wet strength resin system, adhesives or additional fusible fibers to form bonds between the fibers and adsorbent particles. Nonlimiting examples of useful fibers include polyester, nylon and polyolefin. (Suppliers of fibers for the nonwovens industry have been listed in "A Guide to Fibers for Nonwovens," *Nonwovens Industry*, June 1998, 66–87.) Examples of wet strength resin systems include melamine/formaldehyde, epichlorohydrin-based resins, polyamines and polyamides. The use of heat fusible fibers for immobilizing particles in fiber matrices has been disclosed. See, e.g., U.S. Pat. No. 4,160,059.

Preferably, the resulting adsorption medium comprises known amounts of adsorbent per area. The adsorbent per area is from about 300 g/m$^2$ to about 1100 g/m$^2$, preferably from about 500 g/m$^2$ to about 700 g/m$^2$. Thus, the appropriate amount of adsorbent contemplated for a specific purpose can be measured simply by cutting a predetermined area of the fiberized resin (i.e., there is no weighing of the fiberized resin).

The adsorption medium preferably is biocompatible (i.e., not producing a toxic, injurious, or immunologic response); has a minimal impact on the properties of the material such as biological composition (e.g., plasma); and is not associated with toxic extractables. The immobilized adsorbent particles of the adsorption medium preferably have high mechanical stability (i.e., no fine particle generation). The adsorption medium contains about 20–70% adsorbent by weight, preferably 30–50% by weight. Preferably the adsorption medium contains about 30% by weight of the adsorbent particle where a fibrous matrix is used. Where a sintered particulate matrix is used with a ground polymeric adsorbent particle, the adsorption medium preferably contains about 50% by weight of the adsorbent particle.

Coating the Adsorbent Particles

The surface hemocompatibility of the particles, matrices or adsorption medium can be improved by coating their surfaces with a hydrophilic polymer. Exemplary hydrophilic polymers include poly(2-hydroxyethyl methacrylate) (pHEMA), which may be obtained from, e.g., Scientific Polymer Products, Inc. (Ontario, N.Y.) and cellulose-based polymers, e.g., ethyl cellulose, which may be obtained from Dow Chemical (Midland, Mich.). See, e.g., Andrade et al., *Trans. Amer. Soc. Artif. Int. Organs XVII*: 222–28 (1971). Other examples of coatings include polyethylene glycol and polyethylene oxide, also available from Scientific Polymer Products, Inc. The polymer coating can increase hemocompatibility and reduce the risk of small particle generation due to mechanical breakdown.

The adsorbent surface may also be modified with immobilized heparin. In addition, strong anion exchange polystyrene divinylbenzene adsorbents may be modified via heparin adsorption. Heparin, a polyanion, will adsorb very strongly to the surfaces of adsorbents which have strong anion exchange characteristics. A variety of quaternary amine-modified polystyrene divinyl benzene adsorbents are commercially available.

The coating can be applied in a number of different methods, including radio frequency glow discharge polymerization, as described in U.S. Pat. No. 5,455,040, which is hereby incorporated by reference and the Wurster coating process (performed by International Processing Corp. (Winchester, Ky.).

In one embodiment, the Wurster coating process can be applied by suspending the adsorbent particles (generally via air pressure) in a chamber such that the hydrophilic polymer, such as pHEMA, can be sprayed evenly onto all surfaces of the adsorbent particle. As illustrated in Example 2, Dowex® XUS-43493 sprayed evenly with pHEMA demonstrated an increase in platelet yield as well as a dramatic effect on platelet shape change with increasing amounts of coating. It was found that the Wurster coating process selectively coated the outside surface of the adsorbent surface, leaving the inside porous surface nearly unaffected.

In a preferred embodiment, the coating can be applied by soaking the immobilized adsorption medium in the hydrophilic polymer (see Example 2). This process is simpler and less expensive than spraying the adsorbent particles with the hydrophilic polymer.

The process is not limited to a process that applies the coating of the adsorption medium at any particular time. For example, in one embodiment, the pHEMA coating is applied after production of the adsorption medium, but prior to heat sealing the adsorption medium. In another embodiment, the adsorption medium is first heat sealed, and then the pHEMA coating is applied. In addition to coating the adsorption medium, the rinsing process associated with pHEMA application serves to remove loose particles and fibers.

As the amount of coating is increased, it becomes more difficult for some compounds to cross the coating to reach the particle surface, resulting in a decrease in adsorption kinetics. Thus, as the amount of coating is increased, an increased mass of adsorbent must generally be used to achieve the same removal kinetics as coated adsorbent. In one embodiment, the optimum level of pHEMA coating is the minimum coating at which a protective effect on plasma function is observed.

The coatings may be sensitive to sterilization. For example, gamma sterilization may result in cross-linking and/or scission of the coating. Therefore, the type (E-beam vs. gamma irradiation) and dose of sterilization may influence the properties of the coated adsorbent. Generally, E-beam sterilization is preferred.

Devices

Devices are provided for reduction of concentration of compounds from biological compositions. The compounds have molecular weights ranging from about 100 g/mol to about 30,000 g/mol. The device is a flow device. An example of a flow device is shown in FIG. 12. Flow devices are known in the literature and are described, for example, in PCT publication WO 96/40857, incorporated by reference herein.

Flow devices permit reduction of concentration of low molecular weight compounds from materials such as blood products by perfusing the blood product through the flow device.

The adsorption medium of the flow device is preferably about 3 to 30 mm thick to promote an even flow of biological fluid without a substantial pressure drop. Preferably the medium is about 3 to 15 mm thick. More preferably, the medium is about 5 to 8 mm thick.

Figure 14:
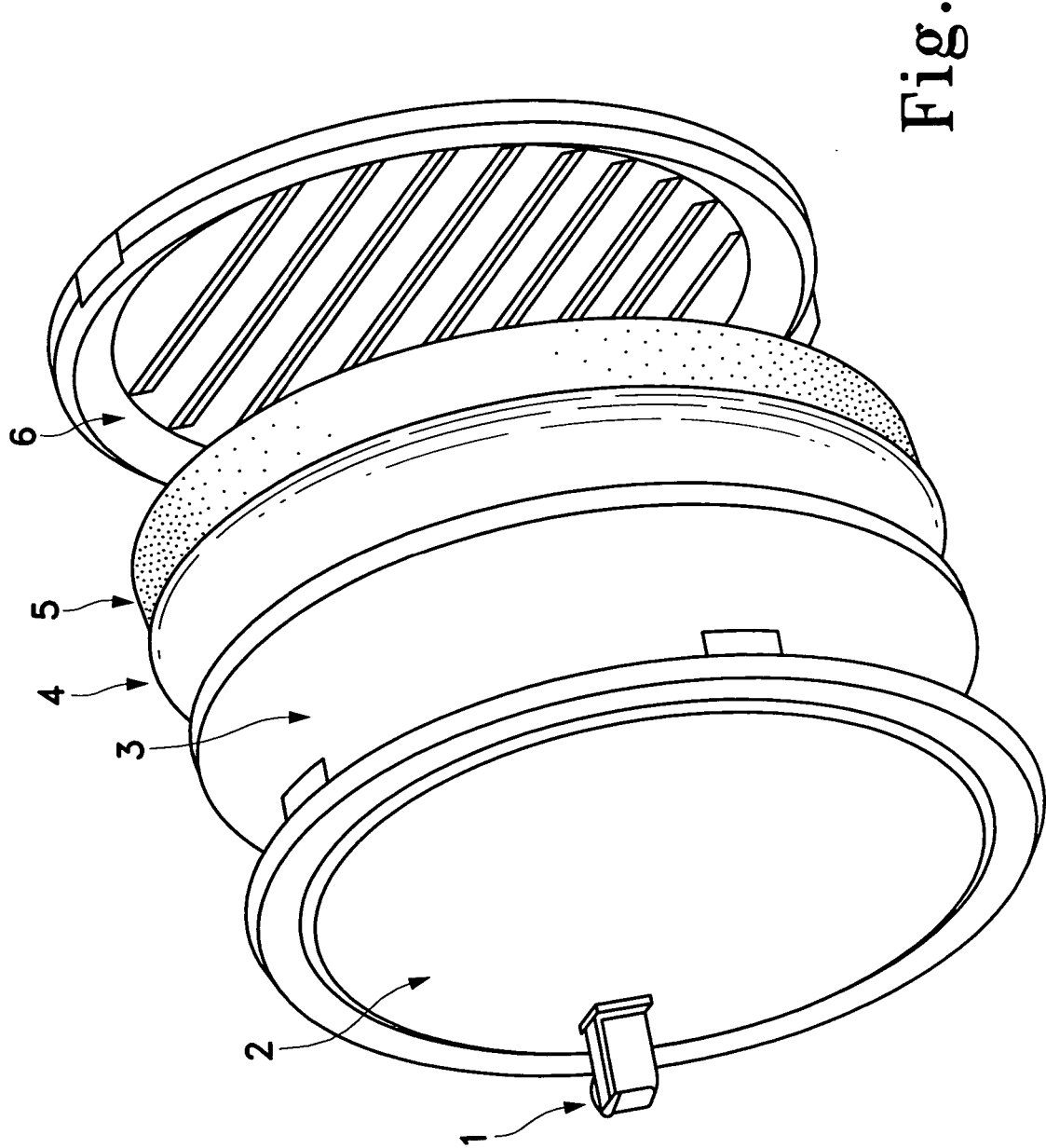
FIG. 14 shows an exploded view of a disk configuration assembly made according to the invention.

In one embodiment, the device is a disk configuration flow device. A disk configuration flow device is shown in reference to FIG. 14, which is an exploded view of the device embodiment. A biological composition to be treated with the device flows through the tubing connector for housing inlet (1). The biological composition then flows through the IAD (Immobilized Adsorption Device) housing inlet (2) and into IAD media (3), which reduces the concentration of a low molecular weight compound in the biological composition. The biological composition then may flow through a pre-filter (4), which is optional. It then flows through a membrane (5) that removes particulate matter from the composition. Finally the treated biological composition exits the device through the IAD housing outlet (6).

Figure 15:
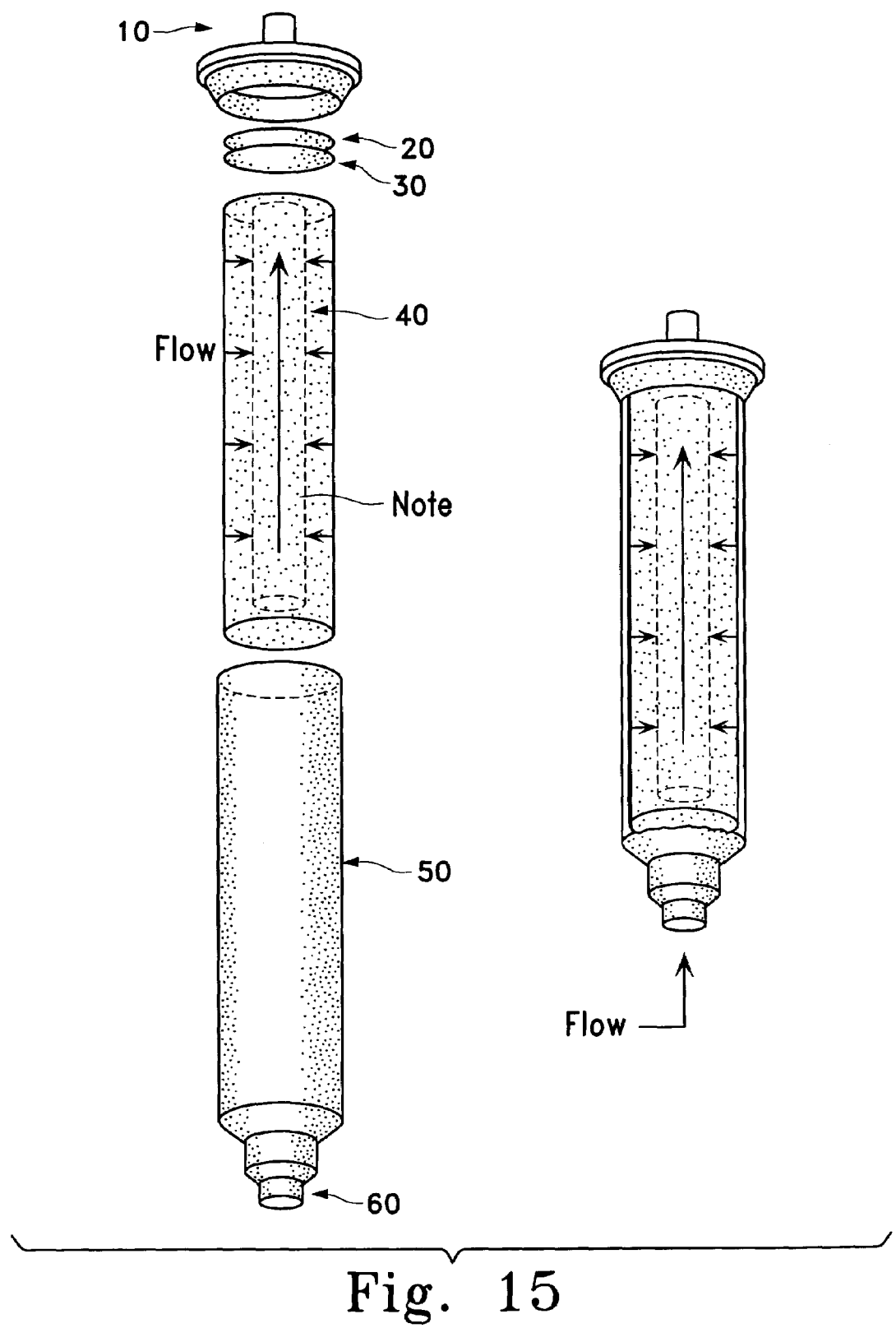
FIG. 15 shows an exploded view of a drip chamber assembly made according to the invention.

In another embodiment, the device is a drip chamber configuration (Porex IAD). A drip chamber configuration flow device is shown in reference to FIG. 15, which is an exploded view. The biological composition to be treated with the device flows through the IAD (Immobilized Adsorption Device) housing inlet (60). The biological composition then flows into the IAD housing (drip chamber) (50) and further into the IAD media (40), which reduces the concentration of a low molecular weight compound in the biological composition. The biological composition then may flow through a pre-filter (30), which is optional. It then flows through a membrane (20) that removes particulate matter from the composition. Finally, the treated biological composition exits the device through the IAD housing outlet (10).

PREFERRED EMBODIMENTS FOR BIOLOGICAL COMPOSITION

In some embodiments, the present invention provides devices for reducing the concentration of compounds in a biological composition. The devices include an adsorption medium and are of a flow configuration. The compounds have a molecular weight ranging from about 100 g/mol to about 30,000 g/mol. The biological activity of the biological composition is substantially maintained after contact with such devices.

Biological response modifiers (e.g., activated complement) like the anaphalatoxin C3a and the terminal membrane attack complex SC5b-9 have been shown to be produced by the processing, (e.g., leukofiltration, pheresis, recovery of shed blood, etc.) and storage of whole blood and its components. These biological response modifiers have been implicated in adverse events in surgery and transfusion.

In some embodiments, the device of the present invention reduces the concentration of activated complement in biological compositions. The concentration of activated complement in the composition is reduced when it is treated with the device, as opposed to a composition that has not been treated with the device. In one embodiment, exposure to the device results in at least about a 30% reduction in C3a complement fragment and SC5b-9 terminal component over control. In another embodiment, exposure to the device results in at least about a 50% reduction in C3a complement fragment and SC5b-9 terminal component over control. In another embodiment, exposure to the device results in at least about a 90% reduction in C3a complement fragment over control.

In one embodiment, the invention provides a device for reducing the concentration of compounds in a biological composition comprising plasma. Treatment of the biological composition comprising plasma with the device substantially maintains the biological activity of the plasma. The adsorption medium comprises adsorbent particles immobilized by an inert matrix. Preferred particles are highly porous and have a surface area greater than about 750 $m^2/g$.

Particularly preferred particles are Norit A Supra, which is available from Norit Americas, Inc. (Atlanta, Ga.). Norit A Supra is a USP-grade activated carbon that is formed by steam activation of coconut shells. This activated carbon has a very high total surface area (2000 $m^2/g$) and is very microporous in nature.

Additionally, the particles may be selected from any of the following particles wherein the particles preferably possess a size range of about 1 $\mu$m to about 200 $\mu$m in diameter, either by grinding direct synthesis, or some other means, and are activated carbons, such as Picactif Medicinal (Pica USA, Columbus, Ohio), synthetic carbonaceous adsorbents, such as Ambersorb 572 (Rohm and Haas, Philadelphia, Pa.), hydrophobic resins, such as Amberlite adsorbents (e.g., Amberlite® XAD-2, XAD-4, and XAD-16), available from Rohm and Haas (Philadelphia, Pa.); Amberchrom® adsorbents available from Toso Haas (TosoHaas, Montgomeryville, Pa.); Diaion®//Sepabeads® Adsorbents (e.g., Diaion® HP20), available from Mitsubishi Chemical America, Inc. (White Plains, N.Y.); Hypersol-Macrone® Sorbent Resins (e.g., Hypersol-Macrone® Sorbent Resins MN-150 and MN-400) available from Purolite (Bala Cynwyd, Pa.) and Dowex® Adsorbents (e.g., Dowex® XUS-40323, XUS-43493, and XUS-40285), available from Dow Chemical Company (Midland, Mich.).

The inert matrix may be composed of synthetic or natural polymeric fibers or particles. In preferred embodiments the matrix is fibrous cellulose or sintered particles of ultra high molecular weight polyethylene.

Exemplary compounds that are reduced or controlled by the devices, materials and methods of the present invention are psoralens, psoralen derivatives, isopsoralens, psoralen photoproducts, methylene blue, phenothiazine, acridine, plastic extractables, biological response modifiers, quenchers and polyamine derivatives.

Where the device is used for compositions comprising plasma, the device maintains adequate levels of clotting activity. Measures of clotting activity include prothrombin time (PT), activated partial thromboplastin time (aPTT), and functional measures of clotting factors I, II, V, VII, VIII, IX, X, XI, and XII. An adequate functional measure of clotting factor activity is greater than about 80% of the level prior to passing through the device, or in the case of clotting times, one that remains in the normal range established for each laboratory that does this type of testing. Preferred measures of clotting activity include PT and aPTT, as they are measures of the overall ability of the plasma to clot, and factors I, II, V, VII, X, XI, and XII, as these factors are not commonly replaced by recombinant proteins. It is preferred to retain more than about 90% of the clotting activity of these factors relative to the level prior to passing through the device and have changes in PT and aPTT of less than about 1.5 seconds.

In one embodiment the device may comprise an adsorption medium and a housing. The housing should promote even flow of the plasma to promote good media utilization and as it primes, allow the plasma to push air ahead of it, thereby eliminating bubbles that would reduce the contact area between the plasma and the adsorption media, thereby reducing the media's utilization. The housing can be flat or have substantial depth to accommodate adsorption media or particle retention media that is not flat, for example cylindrically shaped adsorption media. In a preferred embodiment, the housing is flat. The housing can have inlets and outlets in various orientations, for example inlet top/outlet top or inlet bottom/outlet bottom. In a preferred embodiment, the outlet is at the bottom to promote good drainage and the inlet is at the top to promote media utilization.

In another embodiment, the device comprising an adsorption medium and a housing may also include a particle retention medium. In a preferred embodiment the device includes a particle retention medium downstream of the adsorption medium to retain particles that are shed from the adsorption medium while maintaining a high fluid flow rate and high recovery of proteins. The particle retention medium can be a membrane, a dry or wet laid matrix of fibers, a sintered polymer matrix, a woven material, a nonwoven material (polyester nonwoven), or a combination thereof.

The device housing holds the particle retention medium in an approximately parallel orientation downstream of the adsorption medium. (U.S. Pat. No. 5,660,731, which is herein incorporated by reference, discloses examples of filter housings.) The housing can be constructed from any suitably rigid, impervious, material that does not substantially adversely affect the biological activity of a fluid. Preferably the housing is constructed from a synthetic polymer. Nonlimiting examples of such polymers include polyacrylic, polyethylene, polypropylene, polystyrene and polycarbonate plastics.

The adsorption medium of the device containing particles immobilized by an inert matrix should be between 3 and 30 mm thick to promote an even flow of biological fluid without a substantial pressure drop. Preferably the medium should be between 3 and 15 mm thick. More preferably, the medium should be between 5 and 8 mm thick.

For the device, gravity flow is preferred. More preferably, the device is a gravity flow device that is constructed to permit flow rates of 0.1–10 mL/cm$^2$/min with differential pressures of 12–72 inches water. More preferably the device permits flowrates of 0.2–5 mL/cm$^2$/min with differential pressures of 24–48 inches of water.

Applications

The present invention contemplates reducing the concentration of low molecular weight compounds in biological compositions. The compounds have a molecular weight ranging from about 100 g/mol to about 30,000 g/mol. Such compounds include, for example, pathogen-inactivating agents such as photoactivation products, aminoacridines, organic dyes and phenothiazines. Exemplary pathogen inactivating agents include furocoumarins, such as psoralens and acridines. Following treatment of a blood product with a pathogen inactivating compound as described for example in U.S. Pat. Nos. 5,459,030 and 5,559,250, incorporated by reference herein, the concentration of pathogen inactivating compounds in the blood product can be reduced by contacting the treated blood product with a device of the invention.

In one embodiment the present invention contemplates a method of inactivating pathogens in solution, wherein the method comprises: a) providing, in any order: i) a cyclic compound, ii) a solution suspected of being contaminated with said pathogens, and iii) fiberized resin; b) treating said solution with said cyclic compound so as to create a treated solution product wherein said pathogens are inactivated; and c) contacting said treated solution product with said fiberized resin, and further comprising a device for reducing the concentration of small organic compounds in a blood product while substantially maintaining a desired biological activity of the blood product, the device comprising highly porous adsorbent particles, wherein the adsorbent particles are immobilized by an inert matrix.

In addition to the pathogen inactivating compound, reactive degradation products thereof can be reduced from the material such as a blood product, for example prior to transfusion.

The materials and devices disclosed herein can be used in apheresis methods. Whole blood can be separated into two or more specific components (e.g., red blood cells, plasma and platelets). The term "apheresis" refers broadly to procedures in which blood is removed from a donor and separated into various components, the component(s) of interest being collected and retained and the other components being returned to the donor. The donor receives replacement fluids during the reinfusion process to help compensate for the volume and pressure loss caused by component removal. Apherersis systems are described in PCT publication WO96/40857, hereby incorporated by reference.

Low Molecular Weight Compounds

A device of the present invention reduces the concentration of low molecular weight compounds in a biological composition. The term "low molecular weight compound" refers to an organic or biological molecule having a molecular weight ranging from about 100 g/mol to about 30,000 g/mol. Low molecular weight compounds include, without limitation, the following compounds: small organic compounds such as psoralens, acridines or dyes; quenchers, such as glutathione; plastic extractables, such as plasticizers; biological modifiers, such as activated complement, that possess a molecular weight between about 100 g/mol and about 30,000 g/mol; and, polyamine derivatives.

Small Organic Compounds

A diverse set of small organic compounds can be adsorbed by the device of the present invention. The molecules can be cyclic or acyclic. In one embodiment the compounds are preferably, cyclic compounds such as psoralens, acridines or dyes. In another embodiment the compounds are thiols.

Nonlimiting examples of cyclic compounds include actinomycins, anthracyclinones, mitomyacin, anthramycin, and organic dyes and photoreactive compounds such as benzodipyrones, fluorenes, fluorenones, furocoumarins, porphyrins, protoporphyrins, purpurins, phthalocyanines, hypericin, Monostral Fast Blue, Norphillin A, phenanthridines, phenazathionium salts, phenazines, phenothiazines, phenylazides, quinolines and thiaxanthenones. Preferably the compounds are furocoumarins or organic dyes. More preferably the compounds are furocoumarins.

Nonlimiting examples of furocoumarins, include psoralens and psoralen derivatives. Specifically contemplated are 4'-aminomethyl-4,5',8-trimethylpsoralen, 8-methoxypsoralen, halogenated psoralens, isopsoralens and psoralens linked to quaternary amines, sugars, or other nucleic acid binding groups. Also contemplated are the following psoralens: 5'-bromomethyl-4,4',8-trimethylpsoralen, 4'-bromomethyl-4,5',8-trimethylpsoralen, 4'-(4-amino-2-aza)butyl-4,5',8-trimethylpsoralen, 4'-(4-amino-2-oxa)butyl-4,5',8-trimethylpsoralen, 4'-(2-aminoethyl)-4,5',8-trimethylpsoralen, 4'-(5-amino-2-oxa)pentyl- 4,5',8-trimethylpsoralen, 4'-(5-amino-2-aza)pentyl-4,5',8-trimethylpsoralen, 4'-(6-amino-2-aza)hexyl-4,5',8-trimethylpsoralen, 4'-(7-amino- 2,5-oxa)heptyl-4,5',8-trimethylpsoralen, 4'-(12-amino-8-aza-2,5-dioxa) dodecyl-4,5',8-trimethylpsoralen, 4'-(13-amino-2-aza-6,11-dioxa) tridecyl- 4,5',8-trimethylpsoralen, 4'-(7-amino-2-aza)heptyl-4,5',8-trimethylpsoralen, 4'-( 7-amino-2-aza-5-oxa)heptyl-4, 5',8-trimethylpsoralen, 4'-(9-amino-2,6-diaza)nonyl-4,5',8-trimethylpsoralen, 4'-(8-amino-5-aza-2-oxa)octyl-4,5',8-trimethylpsoralen, 4'-(9-amino-5-aza-2-oxa)nonyl-4,5',8-trimethylpsoralen, 4'-( 14-amino-2,6, 11-triaza)tetradecyl-4, 5',8-trimethylpsoralen, 5'-(4-amino-2-aza)butyl-4,4',8-trimethylpsoralen, 5'-(6-amino-2-aza)hexyl-4,4',8-trimethylpsoralen and 5'-(4-amino-2-oxa)butyl-4,4',8-trimethylpsoralen. Preferably, the psoralen is 4'-(4-amino-2-oxa)butyl-4,5',8-trimethylpsoralen.

Acridines

Nonlimiting examples of acridines include acridine orange, acriflavine, quinacrine, N1, N1-bis (2-hydroxyethyl)-N-4-(6-chloro-2-methoxy-9-acridinyl)-1,4-pentanediamine S-(9-acridinyl)-glutathione. In a preferred embodiment the acridine is N-(9-acridinyl)-β-alanine, alternatively, named 5-[(β-carboxyethyl)amino]acridine.

Dyes

Nonlimiting examples of dyes include phenothiazines such as methylene blue, neutral red, toluidine blue, crystal violet and azure A, phenothiazones such as methylene violet Bernthsen, phthalocyanines such as aluminum 1,8,15,22-tetraphenoxy-29H,31H-phthalocyanine chloride and silica analogues, and hypericin. Preferably, the dye is methylene blue or toluidine blue. More preferably, the dye is methylene blue.

The term "thiazine dyes" includes dyes that contain a sulfur atom in one or more rings. The most common thiazine dye is methylene blue [3,7-Bis(dimethylamino)-phenothiazin-5-ium chloride). Other thiazine dyes include, but are not limited to, azure A, azure C and thionine, as described e.g. in U.S. Pat. No. 5,571,666 to Schinazi.

The term "xanthene dyes" refers to dyes that are derivatives of the compound xanthene. The xanthene dyes may be placed into one of three major categories: i) fluorenes or amino xanthenes, ii) the rhodols or aminohydroxyxanthenes, and iii) the fluorones or hydroxyxantheses. Examples of xanthene dyes contemplated for use with the present invention include rose bengal and eosin Y; these dyes may be commercially obtained from a number of sources (e.g., Sigma Chemical Co., St. Louis, Mich.), and as described e.g. in U.S. Pat. No. 5,571,666 to Schinazi, hereby incorporated by reference.

Quenchers

The concentration of a variety of compounds may be reduced. Other exemplary compounds include quenching compounds. Methods for quenching undesired side reactions of pathogen inactivating compounds that include a functional group which is, or which is capable of forming, an electrophilic group, are described in the co-filed U.S. patent application, "Methods for Quenching Pathogen Inactivators in Biological Systems", U.S. Ser. No. 60/070,597, filed Jan. 6, 1998, the disclosure of which is incorporated herein. In this method, a material, such a's a blood product, is treated with the pathogen inactivating compound and a quencher, wherein the quencher comprises a nucleophilic functional group that is capable of covalently reacting with the electrophilic group. In one embodiment, the pathogen inactivating compound includes a nucleic acid binding ligand and a functional group, such as a mustard group, which is capable of reacting in situ to form the electrophilic group. Examples of quenchers include, but are not limited to, compounds including nucleophilic groups. Exemplary nucleophilic groups include thiol, thioacid, dithoic acid, thiocarbamate, dithiocarbamate, amine, phosphate, and thiophosphate groups. The quencher may be, or contain, a nitrogen heterocycle such as pyridine. The quencher can be a phosphate containing compound such as glucose-6-phosphate. The quencher also can be a thiol containing compound, including, but not limited to, glutathione, cysteine, N-acetylcysteine, mercaptoethanol, dimercaprol, mercaptan, mercaptoethanesulfonic acid and salts thereof, e.g., MESNA, homocysteine, aminoethane thiol, dimethylaminoethane thiol, dithiothreitol, and other thiol containing compounds. Exemplary aromatic thiol compounds include 2-mercaptobenzimidazolesulfonic acid, 2-mercapto-nicotinic acid, napthalenethiol, quinoline thiol, 4-nitro-thiophenol, and thiophenol. Other quenchers include nitrobenzylpyridine and inorganic nucleophiles such as selenide salts or organoselenides, thiosulfate, sulfite, sulfide, thiophosphate, pyrophosphate, hydrosulfide, and dithionitrite. The quencher can be a peptide compound containing a nucleophilic group. For example, the quencher may be a cysteine containing compound, for example, a dipeptide, such as GlyCys, or a tripeptide, such as glutathione.

Compounds that may be removed by the device of the present invention may include thiols such as methyl thioglycolate, thiolactic acid, thiophenol, 2-mercaptopyridine, 3-mercapto-2-butanol, 2-mercaptobenzothiazole, thiosalicylic acid and thioctic acid.

Plastic Extractables

The concentration of a group of low molecular weight compounds that are extractables from plastic storage containers and tubing used to handle biological compositions may also be reduced in a biological composition using a device of the present invention. Examples of extractables include, but are not limited to, plasticizers, residual monomer, low molecular weight oligomers, antioxidants and lubricants. See, e.g., R. Carmen, *Transfusion Medicine Reviews* 7(1):1–10 (1993). The sterilization of plastic components by steam, gamma irradiation or electron beam can produce oxidative reactions and/or polymer scission, resulting in the formation of additional extractable species.

Plasticizers are commonly used to enhance properties of plastics such as processability and gas permeability. The most common plasticizer found in blood storage containers is di(2-ethylhexyl) phthalate (DEHP), which is used in PVC formulations. DEHP has been identified as a potential carcinogen. Alternative plasticizers have been developed, including, without limitation, the following compounds: tri (2-ethylhexyl) trimellitate (TEHTM), acetyl-tri-n-hexyl citrate (ATHC), butyryl-tri-n-hexyl-citrate (BTHC), and di-n-decyl phthalate.

A device of the present invention may be used to reduce or control the concentration of plastic extractables in a biological composition in a variety of settings. Such settings include, but are not limited to, the following: blood treatment; blood storage; and, extracorporeal applications such as hemodialysis and extracorporeal membrane oxygenation.

Biological Response Modifiers (BRMs)

The concentration of a group of low molecular weight compounds broadly referred to as biological response modifiers (BRMs) may also be reduced in a biological composition using a device of the present invention. BRMs are defined as "a wide spectrum of molecules that alter the immune response." *Illustrated Dictionary of Immunology*, J. M. Cruse and R. E. Lewis. General groups of BRMs include, without limitation, the following types of compounds: small molecules such as histamine and serotonin; lipids such as thromboxanes, prostaglandins, leukotrienes and arachidonic acid; small peptides such as bradykinin; larger polypeptides that contain further groups, including activated complement fragments (C3a, C5a); cytokines such as IL-1, IL-6 and IL-8; and chemokines such as RANTES and MIP.

The accumulation of BRMs in a blood product during storage can adversely affect the desired biological activity of a biological composition. Complement activation, for example, has been demonstrated to occur during storage of platelets under standard blood bank conditions. Complement activation has been associated with a loss of platelet function and viability termed "platelet storage lesion." See, e.g., V. D. Mietic and 0. Popovic, *Transfusion* 33(2):150–154 (1993). The accumulation of BRMs in a stored blood products can also, for example, adversely affect a patient that receives the blood product: the accumulation of BRMs in platelet concentrates during storage has been associated with non-hemolytic febrile transfusion reactions in patients receiving platelets. See, e.g., N. M. Heddle, *Current Opinions in Hematology* 2(6):478–483 (1995).

Polyamine Derivatives

The concentration of a group of low molecular weight compounds known as polyamine derivatives may also, for example, be reduced in a biological composition using a device of the present invention. Polyamine derivatives are compounds that contain multiple nitrogen atoms in a carbon backbone.

Polyethylene Glycols

Other exemplary compounds include activated polyethylene glycols (aPEG), which may be used for the modification of the surface of cells or materials in order to provide immunomasking properties or pacification toward protein binding, respectively. The device may be used for the reduction of either the excess activated polyethylene glycol or the unreactive derivative of the PEG resulting from the reaction of the activated PEG with water or small nucleophiles such as phosphate, phosphate esters or thiols, such as glutathione. Other compounds that may be removed include impurities in the activated PEG preparation, which may affect the function of the blood products or make them unsuitable for transfusion (eg. toxic compounds). Finally, small molecules (leaving groups) such as N-Hydroxy succinimide which are released during the reaction of the aPEG with cell surface nucleophiles may also be reduced.

Examples of compounds that may be removed by the device of the present invention include linear or branched polyethylene glycols attached to activating moeities which may include cyanuryl chloride, succinimidyl esters, oxycarbonyl imidazole derivatives, nitrophenyl carbonate derivatives, glycidyl ether derivatives, and aldehydes.

EXAMPLES

The following examples serve to illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); μL (microliters); cm (centimeters); mm (millimeters); μm (micrometers); nm (nanometers); min. (minutes); s and sec. (seconds); J (Joules, also watt second); ° C. (degrees Centigrade); TLC (Thin Layer Chromatography); HPLC (high pressure liquid chromatography); pHEMA and p(HEMA) (poly[2-hydroxyethyl methacrylate]); PC(s) (platelet concentrate(s)); PT (prothrombin time); aPTT (activated partial thromboplastin time); TT (thrombin time); HSR (hypotonic shock response); FDA (United States Food and Drug Administration); GMP (good manufacturing practices); DMF (Drug Masterfiles); SPE (Solid Phase Extraction); Aldrich (Milwaukee, Wis.); Asahi (Asahi Medical Co., Ltd., Tokyo, Japan); Baker (J.T. Baker, Inc., Phillipsburg, N.J.); Barnstead (Barnstead/Thermolyne Corp., Dubuque, Iowa); Becton Dickinson (Becton Dickinson Microbiology Systems; Cockeysville, Md.); Bio-Rad (Bio-Rad Laboratories, Hercules, Calif.); Cerus (Cerus Corporation; Concord, Calif.); Chrono-Log (Chrono-Log Corp.; Havertown, Pa.); Ciba-Corning (Ciba-Corning Diagnostics Corp.; Oberlin, Ohio); Consolidated Plastics (Consolidated Plastics Co., Twinsburg, Ohio); Dow (Dow Chemical Co.; Midland, Mich.); Eppendorf (Eppendorf North America Inc., Madison, Wis.); Gelman (Gelman Sciences, Ann Arbor, Mich.); Grace Davison (W.R. Grace & Co., Baltimore, Md.); Helmer (Helmer Labs, Noblesville, Ind.); Hoechst Celanese (Hoechst Celanese Corp., Charlotte, N.C.); International Processing Corp. (Winchester, Ky.); Millipore (Milford, Mass.); NIS (Nicolet, a Thermo Spectra Co., San Diego, Calif.); Poretics (Livermore, Calif.); Purolite (Bala Cynwyd, Pa.); Quidel (San Diego, Calif.); Rohm and Haas (Chauny, France); Saati (Stamford, Conn.); Scientific Polymer Products (Ontario, N.Y.); Sigma (Sigma Chemical Company, St. Louis, Mo.); Spectrum (Spectrum Chemical Mfg. Corp., Gardenia, Calif.); Sterigenics (Corona, Calif.); Tetko, Inc. (Depew, N.Y.); TosoHaas (TosoHass, Montgomeryville, Pa.); Wallac (Wallac Inc., Gaithersburg, Md.); West Vaco (Luke, W.Va.); YMC (YMC Inc., Wilmington, N.C.); DVB (divinyl benzene); LAL (Limulus Amoebocyte Lystate); USP (United States Pharmacopeia); EAA (ethyl-acetoacetate); EtOH (ethanol); HOAc (acetic acid); W (watts); mW (milliwatts); NMR (Nuclear Magnetic Resonance; spectra obtained at room temperature on a Varian Gemini 200 MHz Fourier Transform Spectrometer); $ft^3$/min (cubic feet per minute); m.p. (melting point); g/min and gpm (gallons per minute); UV (ultraviolet light); THF (tetrahydrofuran); DMEM (Dulbecco's Modified Eagles Medium); FBS (fetal bovine serum); LB (Luria Broth); EDTA (ethelene diamine tetracidic acid); Phorbol Myristate Acetate (PMA); phosphate buffered saline (PBS); AAMI (Association for the Advancement of Medical Instruments); ISO (International Standards Organization); EU (endotoxin units); LVI (large volume injectables); GC (gas chromatography); M (mega-); kGy (1000 Gray=0.1 MRad); MΩ (Mohm); PAS III (platelet additive solution III); $dH_2O$ (distilled water); IAD (immobilization adsorption device); SCD (sterile connection [connect] device).

One of the examples below refers to HEPES buffer. This buffer contains 8.0 g of 137 mM NaCl, 0.2 g of 2.7 mM KCl, 0.203 g of 1 mM $MgCl_2(6H_2O)$, 1.0 g of 5.6 mM glucose, 1.0 g of 1 mg/ml Bovine Serum Albumin (BSA) (available from Sigma, St. Louis, Mo.), and 4.8 g of 20 mM HEPES (available from Sigma, St. Louis, Mo.).

Example 1

Preparation of Fiberized Resin

Preparation of Fiberized Resin and Adsorbent Beads

Immobilized adsorbent media containing Amberlite® XAD-16 in a cleaned and hydrated state (Rohm and Haas) was obtained from AQF. The fibers of Hoechst Celanese's fiber network consisted of a polyethylene terephthalate core and a nylon sheath, the sheath having a lower melting temperature than the core. The fiberized resin was prepared by first evenly distributing the adsorbent beads in the fiber network. Next, the fiber network was rapidly heated causing the polymer sheath of the fibers to melt and bond to the adsorbent beads and other fibers, forming a cross-linked fiber network. The fiberized resin formed contained the Amberlite® XAD-16 at a loading of 130 $\mu m^2$ (i.e., each square meter of fiber contained 130 g of adsorbent beads).

The fiberized resin was cut into squares (14 cm×14 cm), and the resulting sections contained approximately 2.5 g of dry Amberlite® XAD-16. The Amberlite® XAD-16 beads were then pre-wet by soaking the fiberized resin in 30% ethanol for approximately 10 minutes. The residual ethanol was then removed by rinsing twice in saline for 10 minutes. Alternative methods of wetting the Amberlite® XAD-16 and other adsorbents are also effective and are contemplated by the present invention. It should be noted that fiberized resin containing other types of beads (e.g., bridged or hypercrosslinked resins like Dowex® XUS-43493) do not require a wetting step for effective psoralen removal.

Amberlite® XAD-16 HP (High Purity) beads were also obtained directly from Rohm and Haas in a cleaned and hydrated state. No pre-wetting was required for the loose (i.e., not immobilized) Amberlite® XAD-16 HP beads prior to incorporation into a mesh pouch; however, the mass of adsorbent was corrected to account for the water content of the beads (2.5 g dry=6.8 g with 62.8% moisture). The Dowex® XUS-43493 beads were obtained from Dow, and the dry beads did not require wetting nor did the mass of the beads require correction for water. Polyester mesh pouches (7 cm×7 cm square; 30 μm openings) were then filled with 2.5 g (dry weight) of either the loose Amberlite® XAD-16 HP or Dowex® XUS-43493 beads.

The fiberized resin and adsorbent-containing pouches were sterilized by autoclaving on "wet" cycle for 45 minutes at 121° C. Thereafter, the fiberized resin and the adsorbent-containing pouches were inserted into separate, sterile, 1-liter PL 2410 Plastic containers (Baxter). Following insertion, the PL 2410 Plastic containers were heat sealed in a laminar flow hood, using sterile scissors, hemostats, and an impulse sealer.

Example 2

Preparation of pHEMA-Coated Adsorbent Beads and Fiberized Resin

Dowex® XUS-43493 (commercially known as Optipore® L493) containing approximately 50% water by weight was obtained from Dow, and polymerized HEMA with a viscosity average molecular weight of 300 kD was obtained from Scientific Polymer Products. Prior to coating, the adsorbent beads were dried to a water content of <5%. A stock solution of pHEMA was prepared by dissolving the polymer in 95% denatured ethanol/5% water to achieve a pHEMA concentration of 50 mg/ml.

The coating process was performed by International Processing Corp. in a 9-inch Wurster fluidized bed coater with a charge of approximately 4 kg (dry) of adsorbent. The coating process involved a pHEMA flow rate of 60–70 g/min, an inlet temperature of 50° C., and an air flow rate of approximately 200 ft$^3$/min. Samples (50 g) of coated adsorbent were removed during the coating process so that coating levels ranging from 3–18% (w/w) pHEMA were obtained; adsorbent beads coated with 3.7%, 7.3%, and 10.9% pHEMA (w/w) were used in the studies described below.

A device containing non-immobilized dry (uncoated) Dowex® XUS-43493 (2.5 g) and pHEMA-coated Dowex® XUS-43493 (3.0 g or 5.0 g) were prepared by placing the desired mass of adsorbent into a square 30 μm polyester mesh pouch (7 cm×7 cm). The adsorbent-filled pouches were inserted into separate sterile, 1-liter PL 2410 Plastic containers (Baxter) and heat sealed with an impulse sealer. Thereafter, the adsorbent-filled pouches containing PL-2410 Plastic containers were sterilized by either E-beam (NIS) or gamma irradiation (SteriGenics) to 2.5 MRad; as previously alluded to, E-beam sterilization is generally preferred.

Hoechst Celanese prepared fiberized resin containing Amberlite® XAD-16 according to the method described in Example 1. The fiberized resin was cut into squares (14 cm×14 cm); the resulting sections contained approximately 2.5 g of dry Amberlite® XAD-16. The Amberlite® XAD-16 of the fiberized resin was simultaneously wet and coated with pHEMA by soaking in a solution containing 50 mg/mL pHEMA in 95% ethanol/5% distilled water. Residual ethanol was removed by rinsing twice in saline for 10 minutes. This procedure resulted in a coating of approximately 6% (w/w) pHEMA. The fiberized resin was then sterilized by autoclaving on "wet" cycle for 45 minutes at 121° C. Thereafter, the fiberized resin was inserted into separate sterile, 1-liter PL 2410 Plastic containers (Baxter) and heat sealed in a laminar flow hood, using sterile scissors, hemostats, and an impulse sealer.

Example 3

Effect of Glycerol and Polyethylene Glycol on Adsorbent Capacity

This example examines the effect of glycerol and polyethylene glycol as stabilizing agents on adsorbent capacity and kinetics of removal of aminopsoralens from plasma. Free (i.e., not fiberized) Amberlite® XAD-16 and Dowex® XUS-43493 adsorbent beads were used in the experiments of this example.

Methodology

Amberlite® XAD-16 HP (Rohm & Haas (Philadelphia, Pa.)) and Dowex® XUS-43493 (Supelco, Bellefonte, Pa.) were dried to <5% water in a 80° C. oven. Known masses of adsorbent were soaked in ethanol solutions containing 0–50% glycerol, 50% PEG-200 or 50% PEG-400 (glycerol, PEG-200, and PEG-400 from Sigma). Following a 15 minute incubation period at room temperature, the excess solvent was removed and the samples were dried overnight in a 80° C. oven; drying the adsorbent at temperatures>120° C. was avoided since changes in adsorbent properties (e.g., pore melting) were previously observed at higher temperatures. After drying, adsorbent samples were weighed to determine the mass of stabilizing agent per mass of adsorbent.

Several individual studies were performed. Control samples of "non-wet" adsorbent and "optimally wet" adsorbent were included in the studies as described below. The non-wet samples of adsorbent were dried adsorbent which was not subjected to any pre-treatment, while the optimally wet samples of adsorbent were prepared by wetting the adsorbent with 30% ethanol/70% dH$_2$O. The optimally-wet adsorbent was rinsed with dH$_2$O to remove residual ethanol. The adsorbent was prepared just prior to the adsorption study to assure that drying did not occur.

Each of the adsorption studies was performed using 100% human plasma containing 150 μM 4'-(4-amino-2-oxa)butyl-4,5',8-trimethyl psoralen spiked with $^3$H-4'-(4-amino-2-oxa)butyl-4,5',8-trimethyl psoralen. Plasma (6.0 mL) was added to vials containing adsorbent treated with different stabilizing agents. Masses of adsorbent were corrected for glycerol or PEG content to give 0.2 g of adsorbent. The vials were placed on a rotator and agitated at room temperature. Plasma samples were removed at various times and levels of residual $^3$H-4'-(4-amino-2-oxa)butyl-4,5',8-trimethyl psoralen were determined. Samples (200 μL) were diluted in 5.0 mL of Optiphase HiSafe Liquid Scintillation Cocktail (Wallac) and were counted on a Wallac 1409 Liquid Scintillation Counter (Wallac).

Figure 7:
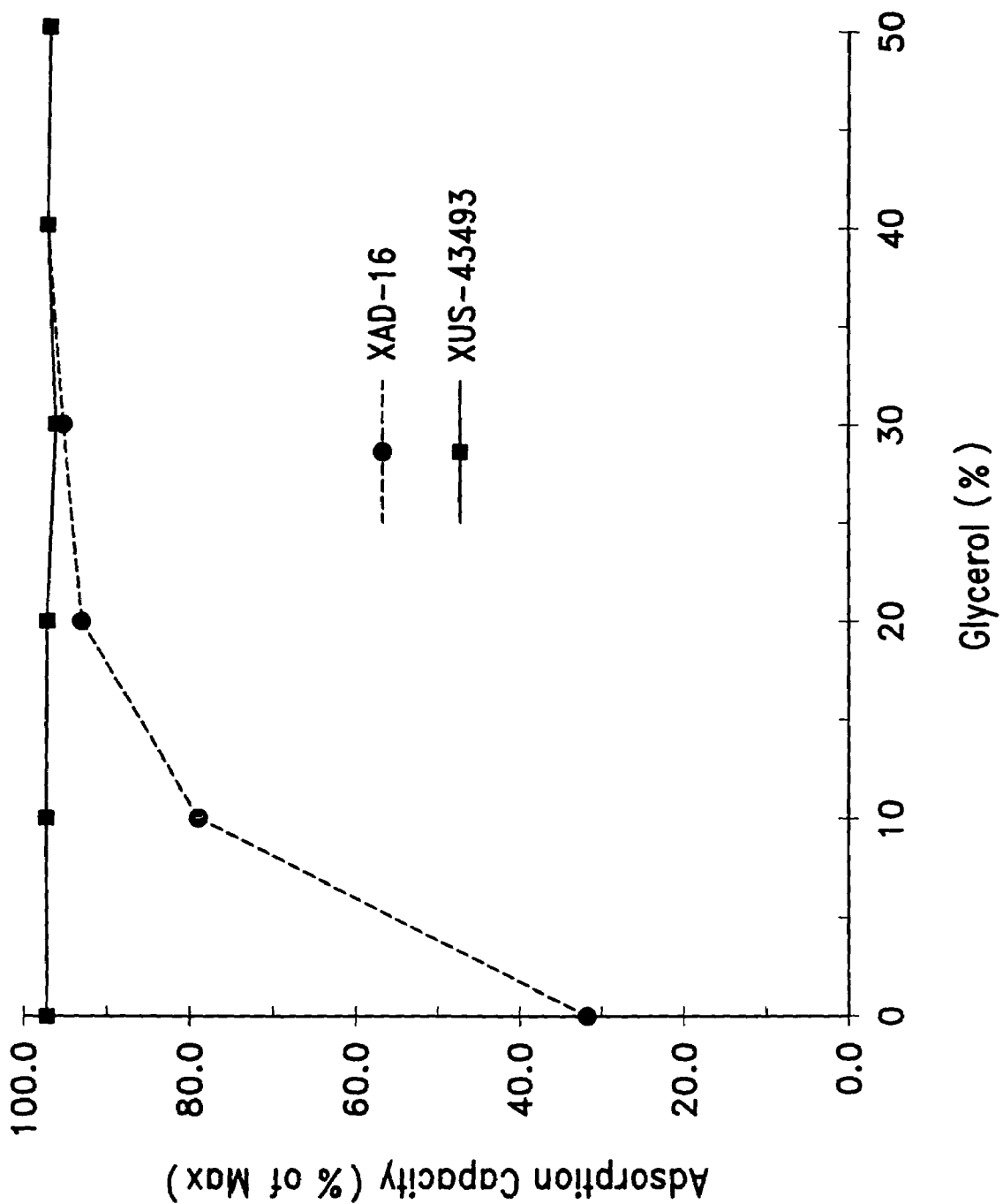
FIG. 7 is a graph showing a comparison of the effect of pre-treatment solution glycerol content on relative aminopsoralens adsorption capacity for Amberlite® XAD-16 and Dowex® XUS-43493.

Adsorption Capacities of Amberlite® XAD-16 and Dowex® XUS-43493 Treated with Glycerol FIG. 7 compares the effect of pre-treatment with ethanol solutions containing various levels of glycerol on relative 4'-(4-amino-2-oxa)butyl-4,5',8-trimethyl psoralen adsorption capacity in 100% plasma for Amberlite® XAD-16 and Dowex® XUS-43493. Adsorbent samples were wet in the ethanol/glycerol solutions for 15 minutes prior to drying for 48 hours at 80° C. Single measurements of adsorption capacity were made after 4 hours of contact. Referring to FIG. 7, glycerol content shown on the x-axis is weight/volume percent of glycerol in ethanol. Adsorption capacities shown on the y-axis are percentages relative to the adsorption capacity of the optimally wet adsorbent sample. The adsorption capacity of XUS-43493 is represented by the squares, while that of XAD-16 is represented by the circles.

As the data in FIG. 7 indicate, the capacity of XAD-16 increased from about 30% in the dry sample to over 90% in the sample wet in a 20% glycerol solution. These results indicate that very low levels of glycerol are required for maintaining high adsorbent capacity after drying. Control samples that were wet in 50% ethanol/50% dH$_2$O (no glycerol) prior to drying demonstrated adsorption capacities which were similar to untreated samples that were dried. In contrast, the XUS-43493 samples did not show any effect of glycerol on adsorption capacity; adsorption capacity approached 100% at all levels of glycerol. While not critical to the practice of the present invention, this observation supports the hypothesis that glycerol acts to prevent the adsorbent pores from collapsing during drying; because XUS-43493 has a highly crosslinked structure, it is not subject to pore collapse upon drying.

Samples that were treated with glycerol appeared to be very stable to drying. No changes were observed in adsorption capacity for samples that were stored for 7 days in a laminar flow hood (data not shown).

Figure 8:
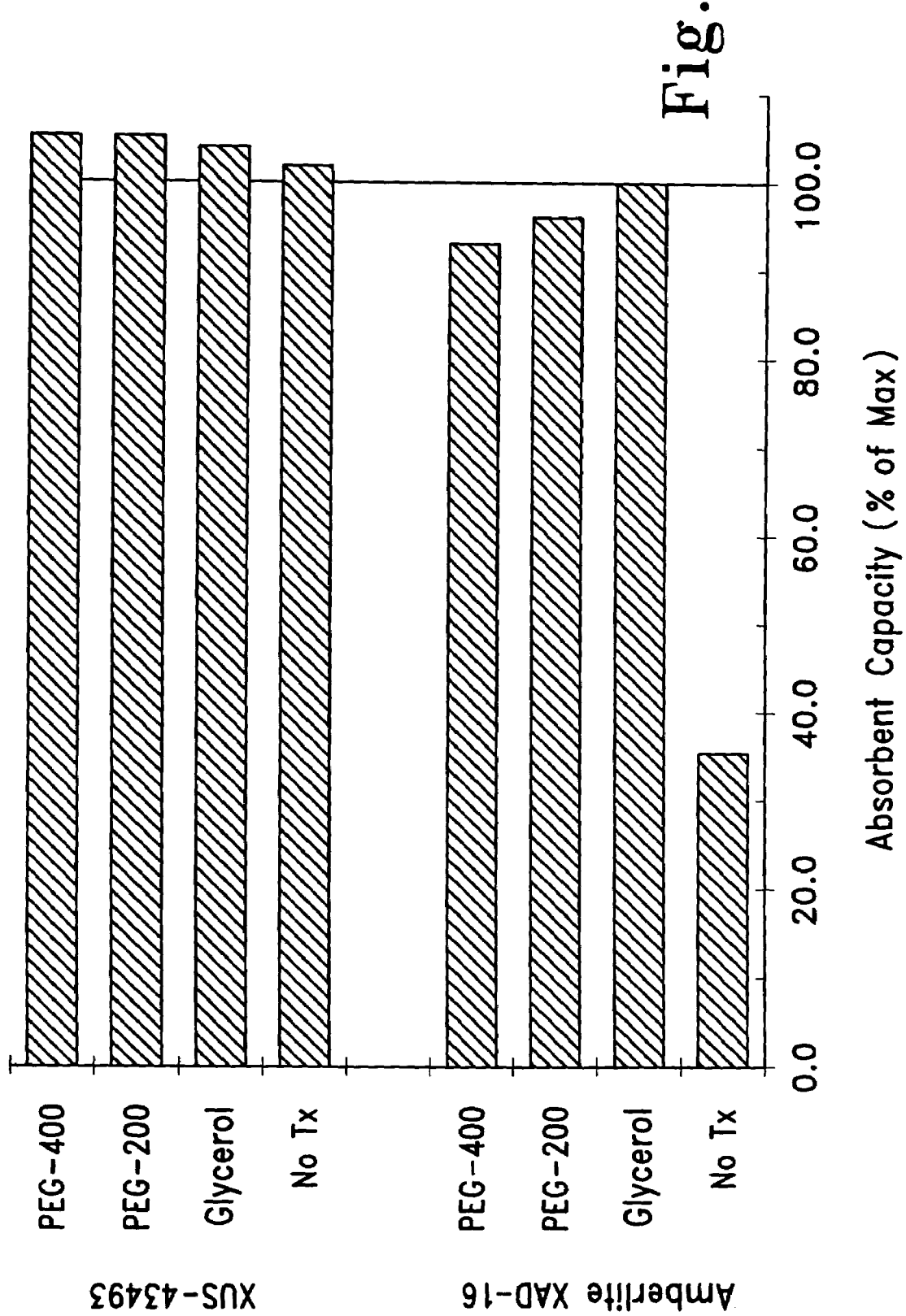
FIG. 8 is a graph showing a comparison of the effect of wetting solution on 4'-(4-amino-2-oxa)butyl-4,5',8-trimethyl psoralen adsorption capacities for dried adsorbent in 100% plasma for Amberlite® XAD-16 (bottom) and Dowex® XUS-43493 (top); the samples that were not wet in an ethanol solution are labeled "No Tx". Adsorbent capacities are reported as percentages relative to the capacity of optimally wet adsorbent.

Adsorption Capacities of Amberlite® XAD-16 and Dowex® XUS-43493 Treated with Glycerol or PEG Additional studies were performed with the low molecular weight polyethylene glycols PEG-200 and PEG-400, low-toxicity agents that are nonvolatile and are soluble in ethanol and water. Samples of adsorbent were treated for 15 minutes in 50% solutions of PEG-400, PEG-200 or glycerol in ethanol. FIG. 8 compares the effect of the stabilizing agents on 4'-(4-amino-2-oxa)butyl-4,5',8-trimethyl psoralen adsorption capacities with dried adsorbent in 100% plasma for Amberlite® XAD-16 (bottom) and Dowex® XUS-43493 (top); the samples that were not wet are labeled "No Tx". Adsorbent capacities are reported as percentages relative to the capacity of optimally wet adsorbent.

As indicated by the data in FIG. 8 and predictable based on the its "macronet" structure, the capacity of Dowex® XUS-43493 was not affected by drying ("No Tx" sample). Conversely, the Amberlite® XAD-16 had approximately 35% of the maximum capacity when dried. Treating XAD-16 with glycerol, PEG-200, and PEG-400 all improved the capacity of the dried adsorbent; the adsorbent capacities with each were all greater than 90%, with glycerol>PEG-200>PEG-400. Though an understanding of the precise mechanism of action is not required to practice the present invention, differences in capacity between the glycerol and the two PEG solutions may be caused by decreasing penetration of the stabilizing agent with increasing molecular weight. That is, during the 15 minute application procedure, the glycerol (MW=92.1) may be able to penetrate the adsorbent pores more completely than either PEG-200 (MW=190–210) or PEG-400 (MW=380–420), which diffuse more slowly because of their larger size.

Adsorption Kinetics of Amberlite® XAD-16 Treated with Glycerol or PEG

Figure 9:
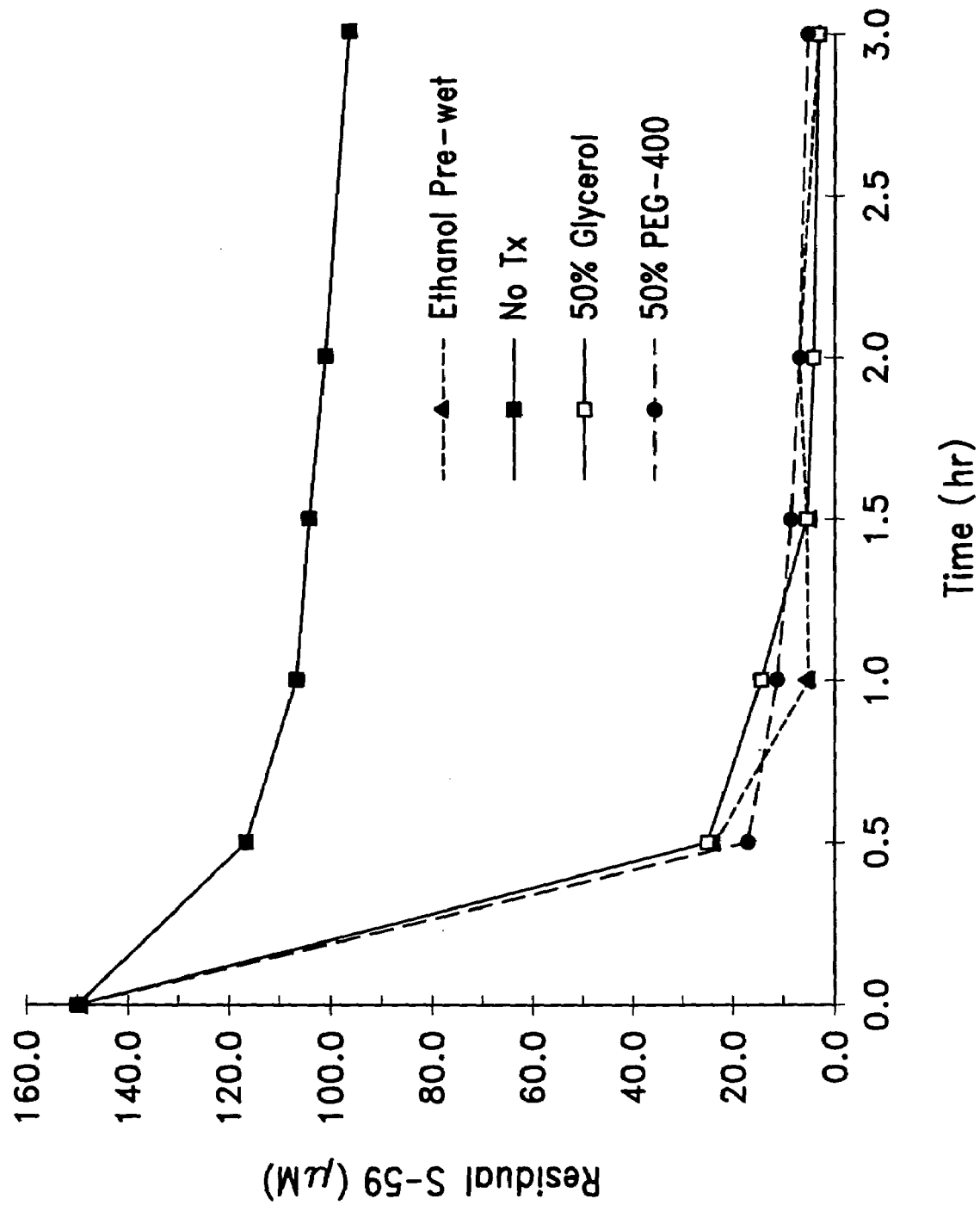
FIG. 9 is a graph showing a comparison of adsorption of aminopsoralens over a 3-hour period from plasma using Amberlite® XAD-16 wet in several different solutions.

A study was also performed to determine whether filling the pores of the adsorbent with glycerol or PEG results in reduced adsorption kinetics. FIG. 9 compares adsorption of 4'-(4-amino-2-oxa)butyl-4,5',8-trimethyl psoralen over a 3-hour period from 100% plasma using Amberlite® XAD-16 wet in several different solutions. Specifically, the data in FIG. 9 represents XAD-16 i) wet prior to drying with a 50% solution of glycerol (open squares connected by solid lines), ii) wet prior to drying with a 50% solution of PEG-400 (shaded circles connected with dashed lines), iii) pre-wet, i.e., just prior to initiating the study, with 50% ethanol/50% dH$_2$O (shaded triangles connected by dashes), and iv) not subjected to any treatment (shaded squares connected by solid lines; "No Tx"). The data in FIG. 9 demonstrate that Amberlite® XAD-16 samples that were wet in 50% glycerol/50% ethanol or 50% PEG-400/50% ethanol solutions had adsorption kinetics which were very close to the sample that was optimally wet in ethanol (i.e., the sample pre-wet with ethanol). The XAD-16 sample that was dried but not treated (No Tx) achieved only about 30% removal by 3 hours.

The data presented in this example indicate that treating Amberlite® XAD-16 with stabilizing agents in the form of solutions containing 50% ethanol and 50% glycerol, PEG-200, or PEG-400 can prevent loss of adsorption capacity associated with drying. The results obtained with these stabilizing agents suggest that low molecular weight wetting agents represent viable methods for enhancing adsorbent function.

Example 4

Removal of Methylene Blue from FFP

This example is directed at the ability of a variety of different polymeric adsorbent materials to remove methylene blue from fresh frozen plasma.

The experiments of this example evaluated "free" adsorbent resin (i.e., not incorporated into device containing non-immobilized adsorbents) and fiberized resin. The free adsorbent resins tested were Amberlite® XAD-16 HP (Rohm and Haas), MN-200 (Purolite), and Dowex® XUS-43493 (Dow Chemical Co.). The XAD-16 HP came in a hydrated state so that no pre-treatment (i.e., no wetting) was necessary, and the MN-200 was also supplied in a fully hydrated state; the XUS-43493 was dry.

Fiberized resin containing XAD-16 was prepared as generally described in Example 1. Briefly, a 2 cm×7 cm (i.e., 14 cm$^2$) strip of fiberized resin containing 130 g/m$^2$ XAD-16 was first wet in 70% ethanol and then rinsed exhaustively in distilled water.

A stock solution of methylene blue (10 mM) was prepared by dissolving U.S.P. methylene blue (Spectrum) in distilled water. The stock solution of methylene blue was added to a sample of 100% plasma to give a final concentration of 10 $\mu$M. Samples of the "free" adsorbent resin (i.e., XAD-16 HP, MN-200, and XUS-43493) were weighed into 50 mL polypropylene tubes for adsorption studies. The water content of each adsorbent was determined by measuring mass loss upon drying. The mass of each adsorbent was corrected for water content so that the equivalent of 0.25 g dry adsorbent was used for each.

A 30 mL sample of the 100% plasma containing 10 μM methylene blue was added to each vial. The vials were placed on a rotator at room temperature. Samples (200 μL) were removed from each vial at 15 minute intervals and assayed for residual methylene blue by HPLC. Each sample of plasma was diluted 5-fold with sample diluent (final concentration=35% methanol, 25 mM $KH_2PO_4$, pH=3.5). Proteins and other macromolecules were precipitated by incubating the samples at 4° C. for 30 minutes. Samples were centrifuged and the supernatant was filtered (0.2 μm) and analyzed on a C-18 reversed phase column (YMC ODS-AM, 4.6 mm×250 mm) by running a linear gradient from 65% solvent A (25 mM $KH_2PO_4$, pH=3.5), 35% B (Methanol) to 80% B in 20 minutes. The limit of detection for the HPLC assay was approximately 0.5 μM methylene blue.

Figure 10:
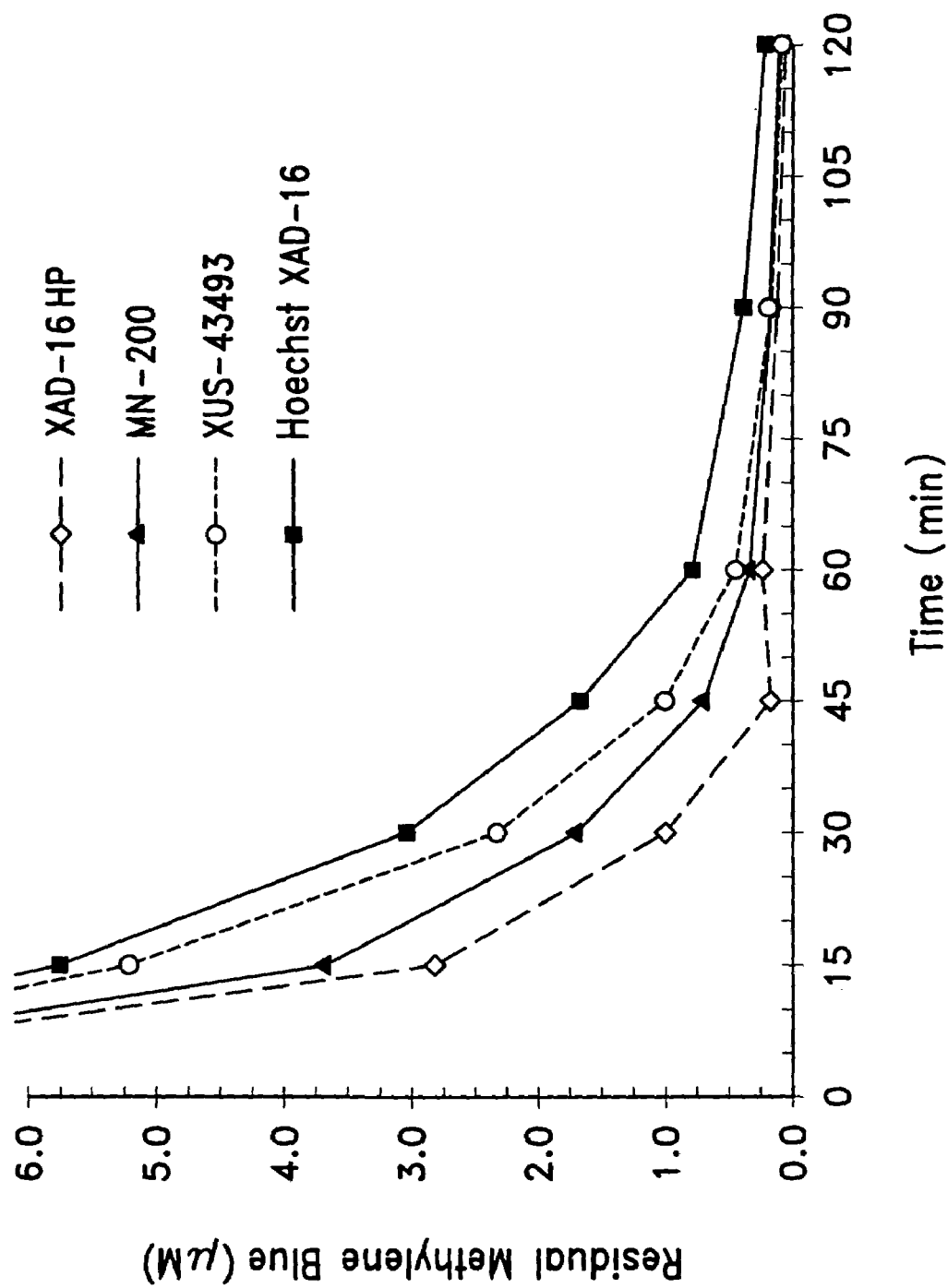
FIG. 10 is a graph showing a comparison of the kinetics of adsorption of methylene blue over a 2-hour period from plasma.

FIG. 10 compares the kinetics of adsorption of methylene blue over a 2-hour period from 100% plasma. Referring to FIG. 10, XAD-16 HP data is represented by open diamonds connected by dashed lines, the MN-200 data is represented by shaded triangles connected by solid lines, the XUS-43493 data is represented by open circles connected by dashed lines, and the fiberized resin containing XAD-16 is represented by shaded squares connected by solid lines. As the data indicate, the XAD-16 HP and MN-200 gave the fastest adsorption kinetics, followed by XUS-43493. The slightly slower kinetics of the XUS-43493 may be a result of slower wetting, as it was used in the dry state. Finally, the fiberized resin containing XAD-16 had the slowest adsorption kinetics. This may have resulted from poor contacting between the fiberized resin and plasma during the incubation, as a portion of the 14 cm² strip of fiberized resin was not completely submersed in the plasma throughout the adsorption study, thereby reducing the effective contact area between the adsorbent and plasma.

The data indicate that non-psoralen pathogen-inactivating compounds like the phenothiazine dyes can be removed from blood products using the resins and fiberized resin contemplated for use with the present invention.

Example 5

This example compares the use of different types of powdered carbon as the active component in the media and demonstrates how careful choice of the active constituent is necessary to reduce the concentration of a small organic compound and preserve the fluid's biological function. The five activated carbons illustrated in Example 5 reduce the concentration of the psoralen, 4'-(4-amino-2-oxa)butyl-4,5',8-trimethyl psoralen, in plasma by approximately the same amount. Where "A Supra" is used as the adsorbent particle, however, there is substantially better retention of clotting factors relative to the other adsorbents.

4'-(4-amino-2-oxa)butyl-4,5',8-trimethyl psoralen was added to plasma at a concentration of 150 μM, and the plasma was illuminated in 325 mL batches with 3.0 J/cm2 UVA to inactivate pathogens. The residual 4'-(4-amino-2-oxa)butyl- 4,5',8-trimethyl psoralen concentration was approximately 90 μM in the resulting plasma pool. 325 mL of illuminated plasma was pumped at 20 mL/min through 5 different types of 90 mm Cuno ZetaPlus carbon pads. Plasma clotting factor levels, clotting times, and 4'-(4-amino-2-oxa)butyl-4,5',8-trimethyl psoralen concentration were assayed before and after flow through the carbon pads.

| | Activated Carbon Specifications | | | | |
|---|---|---|---|---|---|
| Cuno Grade | 4'-(4-amino-2-oxa)butyl-4,5',8-trimethyl psoralen % Removed | aPTT Increase (s) | I % Yield | VIII % Yield | IX % Yield |
| R11S | 99.3 | 4.8 | 91 | 89 | 80 |
| R12S | 99.4 | 4.9 | 93 | 89 | 48 |
| R13S | 99.4 | 6.4 | 88 | 90 | 42 |
| R14S | 99.3 | 3.4 | 96 | 85 | 50 |
| A Supra | 99.4 | 1.6 | 96 | 81 | 82 |

| Activated Carbon | Activated Carbon | Ash Content | Activation | Special Treatment |
|---|---|---|---|---|
| R11S | Mineral | 14% | Steam | No |
| R12S | Lignite | not determined | Steam | No |
| R13S | Peat | 8% | Steam | Acid washed |
| R14S | Peat | 8% | Acid ($H_2SO_4$) | No |
| A Supra | Coconut Shells | 3% | Steam | No |

The water flow rate for R10S media is 2 gallons water/min/square foot with a differential pressure of 1.5 p.s.i.

This example shows that the choice of activated carbon used can have a strong effect on the IAD's impact on biological activity.

Notes: The A Supra grade was prepared to the same specifications as the R1xS series; only the carbon was changed. An increase in aPTT indicates removal of clotting factors. I, VIII, and IX refer to particular clotting factors. All values are relative to post-photochemical treatment. 4'-(4-amino-2-oxa)butyl-4,5',8-trimethyl psoralen was assayed by HPLC and clotting factors and times were assayed by an automated coagulation analyzer.

Example 6

Effect of Particle Size on Low Molecular Weight Compound Removal and Biological Activity. This example demonstrates that the size of the adsorbent particles used in the IAD can have an important effect on the degree of low molecular weight compound removal and measures of biological activity.

Photochemically treated plasma was similarly prepared as in Example 5. Dowex Optipore L493 was ground with a Estro Model 480 grinder and sieved with approximately 100 μm and 50 μm sieves to generate two classes of particles, those between 50 μm and 100 μm and those less than 50 μm. ZetaPlus-like filters were prepared containing either of these two classes of particles according to Cuno R1xS specifications. Photochemically treated plasma (325 mL) was pumped through each pad at 20 L/mmin. 4'-(4-amino-2-oxa)butyl-4,5',8-trimethylpsoralen and clotting factors were analyzed as in Example 5.

| Particle Size ($\mu$m) | 4'-(4-amino-2-oxa)butyl-4,5',8-trimethyl psoralen % Removed | PTT Increase (s) | I % Yield | VIII % Yield | IX % Yield |
|---|---|---|---|---|---|
| 100 >> 50 | 96.1 | 0.9 | 97 | 94 | 86 |
| <50 | 99.2 | 2.2 | 83 | 91 | 76 |

With this particular adsorbent, the smaller particle size resulted in substantially better removal but had a larger impact or biological activity, as measured by clotting activity. This illustrates the trade-off that is often seen with selecting a particle size for the adsorbent particle.

Example 7

Effect of Adsorbent Loading on Low Molecular Weight Compound Removal and Biological Activity. This example compares the effect of changing the mass fraction of the active component on reducing the concentration of a small organic compound and the tradeoff with the fluid's biological function.

Photochemically treated plasma was similarly prepared as in Example 5. A Supra pads were prepared with the standard R1xS loading of approximately 60% Carbon and a lower loading level of 30%. Approximately 230 mL plasma was pumped through each 90 mm disc. 4'-(4-amino-2-oxa)butyl-4,5',8-trimethyl psoralen and clotting factors were analyzed as in Example 5.

| A Supra Loading (%) | 4'-(4-amino-2-oxa)butyl-4,5',8-trimethyl psoralen % Removed | PTT Increase (s) | I % Yield | VIII % Yield | IX % Yield |
|---|---|---|---|---|---|
| 61.5 | 99.4 | 1.3 | 93 | 93 | 77 |
| 30.8 | 99.4 | 0.9 | 99 | 90 | 91 |

This demonstrates the unexpected result that by reducing the loading of adsorbent particles, it is sometimes possible to reduce the IAD's effect on biological activity, while still substantially reducing the concentration of the low molecular weight compound. Overall capacity of the IAD will be reduced, but as long as the IAD is operated at significantly less than the theoretical capacity for the low molecular weight compound, this does not matter.

Example 8

Effect of Using a Hemocompatible Coating. This example demonstrates that in some cases, treating the media with a hydrophilic polymer can have benefits to biological function.

Photochemically treated plasma was similarly prepared as in Example 5. One 90 mm R14S pad was flushed overnight with a 50 mg/mL solution of polyhydroxyethymethacrylate (pHEMA) in 95% ethanol dried in a 70° C. oven until there was no additional weight change. The second pad was similarly flushed with 95% ethanol without pHEMA and dried. Approximately 325 mL plasma was pumped through the discs at 5 mL/min. 4'-(4-amino-2-oxa)butyl-4,5',8-trimethyl psoralen and clotting factors were analyzed as in Example 5.

| Coating | 4'-(4-amino-2-oxa)butyl-4,5',8-trimethyl psoralen % Removed | PTT Increase (s) | I % Yield |
|---|---|---|---|
| None | 99.6 | 4.1 | 98 |
| pHEMA | 99.1 | 2.5 | 103 |

Though the coating showed benefits to the biological activity of the biological composition, in this case, the clotting activity of plasma, coating had an adverse effect on the ability of the IAD to reduce the concentration of the low molecular weight compound used in this example, 4'-(4-amino-2-oxa)butyl-4,5',8-trimethylpsoralen. This illustrates the trade-offs that are often seen when selecting a coating or surface treatment.

Example 9

Effect of Flow Rate on Low Molecular Weight Compound Removal and Biological Activity. This example demonstrates that flowrate can have an effect on the reduction in concentration of the small organic compound.

Photochemically treated plasma was similarly prepared as in Example 5. A Supra pads were prepared with the standard RlxS loading of approximately 60% carbon and 325 mL of the treated plasma was pumped through each of the 47 mm diameter discs at three different flowrates. 4'-(4-amino-2-oxa)butyl-4,5',8-trimethyl psoralen and clotting factors were analyzed as in Example 5.

| Flowrate (mL/min) | 4'-(4-amino-2-oxa)butyl-4,5',8-trimethyl psoralen % Removed | PTT Increase (s) | I % Yield | VIII % Yield | IX % Yield |
|---|---|---|---|---|---|
| 10 | 99.0 | 1.3 | 98 | 83 | 80 |
| 15 | 98.8 | 1.5 | 99 | 85 | 86 |
| 20 | 98.7 | 1.4 | 97 | 89 | 86 |

Though increasing the flow rate showed a slight decrease in the degree of removal of low molecular weight compound, it had a more substantial benefit to the biological activity, as seen by the higher yield of factor VIII and factor IX clotting activity. This shows that adjusting the flux of the biological composition through the IAD can confer selectivity for low molecular weight compound reduction over effects on biological activity.

Example 10

Effect of Fluid Volume on Low Molecular Weight Compound Removal and Biological Activity. This example demonstrates that fluid volume can also have an important effect on conferring selectivity for low molecular weight compounds over mediators of biological activit.

Photochemically treated plasma was similarly prepared as in Example 5. ZetaPlus-like filters were prepared with ground Dowex Optipore L493 with particles less than 50 μm instead of powdered activated carbon according to the Cuno RlxS specifications. Plasma was pumped through the filter at 20 mL/min and samples were taken at 180 mL and 325 mL. 4'-(4-amino-2-oxa)butyl-4,5',8-trimethyl psoralen and clotting factors were analyzed as in Example 5.

| Plasma Volume (mL) | 4'-(4-amino-2-oxa)butyl-4,5',8-trimethyl psoralen % Removed | PTT Increase (s) | I % Yield | VIII % Yield | IX % Yield |
|---|---|---|---|---|---|
| 180 | 99.3 | 4.1 | 74 | 89 | 66 |
| 325 | 99.2 | 2.2 | 83 | 91 | 76 |

Thus, by increasing the fluid volume treated, additional selectivity can be conferred on low molecular compound removal over reduction in biological activity. There is a limit to this of course, as the capacity of the IAD for of the low molecular weight compound is approached, selectivity will again decrease.

Example 11

Use of Sintered Media. Ninety millimeter diameter by ¼" thick discs were fabricated by Porex. The discs contained various weight fractions of finely ground Dowex Optipore L493 with particle sizes between 20 μm and 100 μm, and small particles of ultra high molecular weight polyethylene (grade UF220), which were then sintered together. Photochemically treated plasma was similarly prepared as in Example 5 and 200 mL of plasma was pumped through each disc at 16–18 mL/min. 4'-(4-amino-2-oxa)butyl-4,5',8-trimethyl psoralen and clotting factors were analyzed as in Example 5.

| Weight Percent Adsorbent | 4'-(4-amino-2-oxa)butyl-4,5',8-trimethyl psoralen % Removed | PTT Increase (s) | I % Yield | VIII % Yield | IX % Yield |
|---|---|---|---|---|---|
| 25 | 97.8 | 0.5 | 93 | 95 | 78 |
| 35 | 99.0 | 1.2 | 90 | 94 | 74 |
| 50 | 99.3 | 1.2 | 91 | 80 | 76 |

As was seen using a fibrous matrix with activated carbon in example 7, changing the fraction of adsorbent in the IAD also has an effect both on low molecular weight compound removal and biological activity when using a sintered matrix. In this case, the 25% formulation does not give as good removal of 4'-(4-amino-2-oxa)butyl-4,5',8-trimethylpsoralen, as the 35% and 50% formulations. The 50% formulation has a greater loss in factor VIII activity than the other formulations. Of the three medias, the 35% formulation confers the highest selectivity of removal of low molecular weigh compound over reduction in biological activity.

Example 12

This example describes the effect of increasing the mass of adsorbent by increasing the diameter of the filter at constant thickness.

Photochemically treated plasma was similarly prepared as in Example 5. Approximately 325 mL of treated plasma was pumped through 90 and 47 mm diameter R03S grade discs at 5 mL/minute. 4'-(4-amino-2-oxa)butyl-4,5',8-trimethyl psoralen and clotting factors were analyzed as in Example 5.

| Disc Diameter (mm) | 4'-(4-amino-2-oxa)butyl-4,5',8-trimethyl psoralen % Removed | PTT Increase (s) | I % Retained |
|---|---|---|---|
| 47 | 99.4 | 2.1 | 96 |
| 90 | 99.6 | 3.5 | 77 |

Increasing the diameter of the adsorbent material while keeping the same thickness and flow rate has the equivalent effect of reducing the flux and reducing the volume treated per unit cross sectional area of filter. Although both of these effects tend to increase adsorption of low molecular weight compounds, they often increase the adsorption of mediators of biological activity, even more. In this example we see that slightly more S-59 was adsorbed with the larger diameter adsorbent material, but substantially more factor I activity was lost.

Example 13

Flow Studies Using Several Forms of Activated Carbon Media.

Experiments were carried out to investigate removal of 5-[(β-carboxyethyl)-amino] acridine and GSH from PRBCs using a flow device. PRBCs (Erythrosol, glucose, 63% HCT) were dosed with 300 μM of a degradable 5-[(β-carboxyethyl)amino] acridine derivative and 3 mM GSH, and held at room temperature without agitation for 20 hours prior to flow through devices. The flow compound adsorption device media consisted of various forms of activated carbon, as either a composite carbon/cellulose disk, or a carbon fiber felt. The media were sealed into a 90 mm diameter polycarbonate housing (Cuno, Meridien, Conn.). The dosed PRBCs were pumped (Gilson Minipuls, Middleton, Wis.) through the media at a flow rate of 5 mL/min, and collected in a PL 146 plastic container (Baxter Healthcare). The results of this study are shown in Table 1.

TABLE 1

Flow study results using various activated carbon media.

| Media | Description | Residual Acridine* (μM) | Residual GSH* (mM) | % Hemolysis |
|---|---|---|---|---|
| CUNO | A Supra/Cellulose disk (30% loading) | 26.04 | 0.94 | 4.83 |
| CUNO 95-1 | A Supra/Cellulose disk (70% loading) | 25.08 | 0.68 | 7.56 |
| CUNO 95-2 | A Supra/Cellulose disk (70% loading) | 19.22 | 0.11 | 5.15 |
| Cellulo | A Supra/Cellulose disk (60% loading) | 23.62 | 0.79 | 5.19 |
| FPI | A Supra/Cellulose disk (70% loading) | 20.78 | 0.20 | 5.27 |
| Ertel | A Supra/Cellulose disk (60% loading) | 25.13 | 0.14 | 7.17 |
| Actitex | Activated C felt-1 layer-162 g/m² | 51.36 | 6.14 | 1.27 |
| Lantor | Activated Carbon felt | 30.90 | 4.27 | 1.78 |
| Ultrasorb | Activated Carbon felt (200 g/m²) | 77.79 | 5.13 | 1.06 |

TABLE 1-continued

Flow study results using various activated carbon media.

| Media | Description | Residual Acridine* (µM) | Residual GSH* (mM) | % Hemolysis |
|---|---|---|---|---|
| Actitex | Activated Carbon felt-3 layers (162 g/m²) | 28.75 | 5.58 | 1.37 |
| Lydall | Activated Carbon felt | 39.69 | 5.04 | 1.18 |
| MN-200 | MN-200/Cellulose disk (70% loading) | 87.87 | 6.44 | 1.11 |

Example 14

Flow Compound Adsorption Devices (CUNO media) vs. Batch Compound Adsorption Devices (AQF media). Studies were performed which compared 5-[ (β-carboxyethyl) amino]acridine and GSH removal in flow versus batch compound adsorption devices. The flow device consisted of a cellulose/Norit A Supra (Norit Americas, Inc. (Atlanta, Ga.)) carbon disk enclosed in a 90 mm housing. There were two separate batch devices: one consisted of fiberized Pica G277 activated carbon (AQF 500 g/m²); the other consisted of fiberized Purolite MN-200 (AQF 312 g/m²). Following dosing with 300 µM of a degradable 5-[(β-carboxyethyl)-amino] acridine derivative and 3 mM GSH, PRBCs were pumped through the cellulose/carbon media at a flow rate of 2 mL/Min, after which 5-[(β-carboxyethyl)-amino] acridine and GSH levels dropped 75 and 88%, respectively, to 24 µM and 0.71 mM in the PRBC supernatant. The flow device exposed PRBCs were then transferred to the 6 g MN-200 batch device, which decreased 5-[ (β-carboxyethyl)-amino] acridine and GSH levels by an additional 5 and 1%, reaching 20 µm and 0.67 mM over 24 hours. Exposure of PRBCs to a 7 g Pica G277 batch device alone resulted in a drop in 5-[(P-carboxyethyl)-amino]acridine and GSH levels by 92 and 54% to concentrations of 8 µM and 3 mM. Therefore, one pass through the flow device was more effective in removing GSH than exposure to the carbon batch device for 24 hours. The batch device alone, however, was more effective in removing 5-[(P-carboxyethyl)-amino]acridine than the flow and MN-200 devices combined. Flow through the device did not seem to have an adverse effect on PRBC ATP concentration. K+ levels in PRBCs were lower after exposure to the flow device as compared to a 24 hour carbon batch device exposure.

Example 15

This example describes the typical performance of an immobilized adsorbent device in a flow mode on plasma using adsorbent media composed of 30% Norit A Supra carbon (Norit Americas, Atlanta, Ga.) and manufactured by Cuno (Meriden, Conn.) previously described in an earlier example.

IADs were assembled using 90 mm Cuno 30% Norit A Supra impregnated R10SP media in series with 90 mm diameter Memtec hydroxypropylcellulose coated polysulfone membrane with 5 µm pores.

To complete disposable manufacture, a 1 LPL2410 bag was docked to ⅛" OD tubing and the tubing was then attached to the outlet of the IAD such that the distance from the midline of the IAD to the bag was 40 cm. The same sized tubing was attached to the inlet of the SRD such that when the illumination bag is docked to it, the distance from the midline to the bag would be 30 cm.

4'-(4-amino-2-oxa)butyl-4,5',8-trimethyl psoralen was added to 500 mL of plasma to a final concentration of approximately 150 µM, and the plasma was illuminated to 6.3 J/cm2 UVA to inactivate pathogens. The post-illumination 4'-( 4-amino-2-oxa)butyl-4,5',8-trimethyl psoralen concentration was approximately 82M.

Table 2 shows measures of clotting factor activity and 4'-(4-amino-2-oxa)butyl-4,5',8-trimethyl psoralen levels after having been treated by the IAD relative to values beforebeing passed through the IAD. The experiment was repeated three times. Means and standard deviations are reported. Treatment time averaged 14 minutes. It is apparent that there is virtually no change in factors I, II, V, VII, X or measures of aggregate clotting activity, the prothrombin time (PT) and activated partial thromboplastin time (aPTT) and very small changes in factors XI and XII. Factors VIII and IX show somewhat larger changes but these are acceptable, especially in light of the prescription of recombinant proteins for their deficiency. The very selective nature of the device should be noted in that it retains virtually all the clotting activity while allowing only 0.9% of the 4'-(4-amino-2-oxa)butyl-4,5',8-trimethyl psoralen to pass through.

TABLE 2

| | |
|---|---|
| PT (s) | 0.0 ± 0.1 |
| aPTT (s) | 0.7 ± 0.1 |
| I (%) | 98 ± 2 |
| II (%) | 99 ± 1 |
| V (%) | 101 ± 2 |
| VII (%) | 99 ± 2 |
| VIII (%) | 86 ± 1 |
| IX (%) | 82 ± 3 |
| X (%) | 103 ± 4 |
| XI (%) | 94 ± 4 |
| XII (%) | 95 ± 5 |
| S-59 (%) | 0.9 ± 0.1 |

Example 16

Reduction of Activated Complement by Adsorbent Medias. This study demonstrates the removal of biological response modifiers by cellulose media impregnated with activated carbon and porous plastic media impregnated with ground polystyrene/divinylbenzene adsorbent.

Zymosan (Sigma Chemical Company; St. Louis, Mo.), a potent activator of the complement cascade, was added to plasma at a concentration of 10 mg/mL. The plasma was incubated with mild shaking at 37° C. for 1 hour. The plasma was then centrifuged and the supernatant saved to get rid of the solid zymosan. Approximately 20 mL of this supernatant was added to each of two 600 mL units of plasma and a sample from each unit was taken for C3a and SC5b-9 analysis. One of these units was pumped at 40 mL/min through a 90 mm disc of carbon impregnated cellulose media (Cat. #2640ASP, Cellulo, Inc.; Fresno, Calif.). The other unit was pumped at the same rate through sintered media prepared as in Example 11 (Porex Technologies; Fairburn, Ga.). The filtrate from each unit was sampled for C3a and SC5b-9 analysis.

Complement assays were performed using Quidel assay kits.

|  | [C3a] (ng/mL) | [SC5b-9] (ng/mL) |
|---|---|---|
| Pre-filtration | 1597 | 5210 |
| Filtration with carbon/cellulose media | 521 | 1747 |
| Filtration with sintered media | 68 | 1592 |

Biological response modifiers can also be removed from biological compositions, as the previous table indicates.

Example 17

Comparison of Carbon Fiber Medias with Carbon Impregnated Cellulose. This example compares the use of carbon fiber medias disclosed in U.S. Pat. No. 5,660,731 with medias disclosed herein.

Photochemically treated plasma was similarly prepared as in Example 5. Approximately 175 mL of the treated plasma was pumped through each of the medias at about 11 mL/min. S-59 and clotting factors were analyzed as in Example 5.

| Media | Total Thickness (in.) | Number of Layers | S-59 Reduction (%) |
|---|---|---|---|
| Kynol CAN-211-20 | 0.203 | 5 | 74.9 |
| Kuractive FT300-20 Felt | 0.234 | 7 | 37.2 |
| Actitex FC1201 | 0.328 | 7 | 44.7 |
| Cuno A Supra | 0.250 | 1 | 99.1 |

Sources of medias: Kynol (American Kynol, Inc.; Pleasantville, N.Y.); Kuractive (Kuraray Chemical Co.; Bizen City, Japan); Actitex (Pica USA; Columbus, Ohio); Cuno A Supra (Cuno, Inc.; Meridien, Conn.).

As the above table shows, using carbon fiber medias to remove low molecular weight compounds from biological compositions as disclosed in U.S. Pat. No. 5,660,731 often does not adequately reduce the concentration of low molecular weight compounds in biological compositions compared to adsorbent medias disclosed herein.

Example 18

Effect of Adsorbent Pore Size Distribution on Biological Activity. This example demonstrates that the pore size distribution of the adsorbent contained in the IAD can have an important effect on the IAD's ability to maintain biological activity.

Ninety millimeter diameter by ¼" thick porous plastic discs were fabricated by Porex Technologies (Fairburn, Ga.). The discs were a sintered mixture of approximately 50% by weight of about 25 µm diameter particles of ultra high molecular weight polyethylene and 50% of one of Purolite's (Bala Cynwyd, Pa.) non-functionalized Hypersol-Macronet adsorbents that were ground by Porex such that more than 90% of the particles (by weight) were between 60 µm and 160 µm in diameter. Photochemically treated plasma were prepared by adding a solution of S-59 to each of three approximately 600 mL units of plasma for an S-59 concentration of about 150 µM, and illuminating each unit with 6.3 J/cm2 UVA as previously described. The treated units were pooled and approximately 600 mL of the pool was pumped through each of the discs at about 40 mL/min. S-59 and clotting factors were analyzed as in Example 5. Surface area was analyzed by equilibrated-step mercury intrusion porosimetry (Micromeritics, Norcross, Ga.).

| Adsorbent | Cumulative Surface Area Associated with Pores > 3 nm in diameter (m²/g) | Cumulative Surface Area Associated with Pores > 20 nm in diameter (m²/g) | Cumulative Surface Area Associated with Pores > 40 nm in diameter (m²/g) |
|---|---|---|---|
| MN-200 | 188 | 55 | 42 |
| MN-250 | 172 | 28 | 7 |
| MN-270 | 165 | 14 | 3 |

| Adsorbent | S-59 Removed (%) | aPTT increase (s) | Factor IX activity (% retained) | Factor XI activity (% retained) |
|---|---|---|---|---|
| MN-200 | 99.5 | 5.8 | 85 | 55 |
| MN-250 | 99.5 | 2.0 | 82 | 77 |
| MN-270 | 99.4 | 0.5 | 100 | 91 |

The choice among these three particular adsorbents used in the IADs had a strong effect on biological activity, as measured by aPTT, Factor IX activity, and Factor XI activity, but did not have a strong effect on the degree of reduction of the low molecular weight compound used in this example, S-59.

Since the three adsorbents used in the IADs in this example, MN200, MN250, and MN270, differ chiefly in the pore size at which each begins to have appreciable surface area and not substantially in their surface chemistry, a conclusion consistent with the above results is that the surface area accessible by the low molecular weight compound is similar among the three adsorbents, resulting in a similar degree of S-59 reduction for each IAD. In addition, it is likely that the better biological activity shown by the IADs containing adsorbents with less surface area associated with larger pores is due to the larger pores allowing certain mediators of the measured biological activity that have a tendency to adsorb to the adsorbents' surfaces, namely factor IX and factor XI in this example, to adsorb or inactivate on the larger pores' surfaces, while smaller pores exclude those mediators from their surfaces.

Example 19

This example demonstrates the utility of using IADs for removing low molecular weight compounds such as viral inactivating agents (psoralen) or biological response modifiers (activated complement-C3a) from whole blood. Whole blood was pre-treated with cellulose acetate membrane to cause complement activation as may be observed in hemodialysis when using cellulose acetate membranes. Hemoperfusion to remove activated complement and added psoralen was simulated by returning the effluent from the hemoperfusion device to a mixed pool of whole blood (see FIG. 13).

Two units of ABO-matched whole blood were obtained from the Sacramento Blood Center (Sacramento, Calif.). The units were maintained at room temperature following donation. The two units were transferred to two PL2410 plastic storage containers (Baxter Healthcare, Deerfield, Ill.) containing 4 pieces of Millipore RA type membrane (47 mm, Millipore, Marlborough, Mass.). The whole blood was incubated for 24 hours at room temperature with the cellulose acetate membranes (Millipore RA) to induce complement activation. Psoralen (150 μM S-59 (4'-(4-amino-2-oxa) butyl-4,5',8-trimethyl psoralen)) was added to each whole blood unit immediately before hemoperfusion was initiated.

The IAD media (300 g/m² MN-200, AQF) was cut into circular disks with a diameter of 47 mm. Disks were sealed in a 47 mm diameter polycarbonate housing with a stainless steel support screen (Cuno Inc., Meridien, Conn.). Tubing (3 mm ID PharMed tubing) was attached to the housing. The tubing was loaded in a peristaltic pump (Masterflex) and the system was calibrated to deliver a flow rate of 75 mL/min. The tubing inlet and outlet were attached to a 600 mL beaker (Nalgene) which was placed on a stir plate (see FIG. 13). The whole blood which was contained in the 500 mL beaker was gently agitated with a Teflon-coated stir bar throughout the study to simulate the mixing that would occur in the subject's body.

Figure 13:
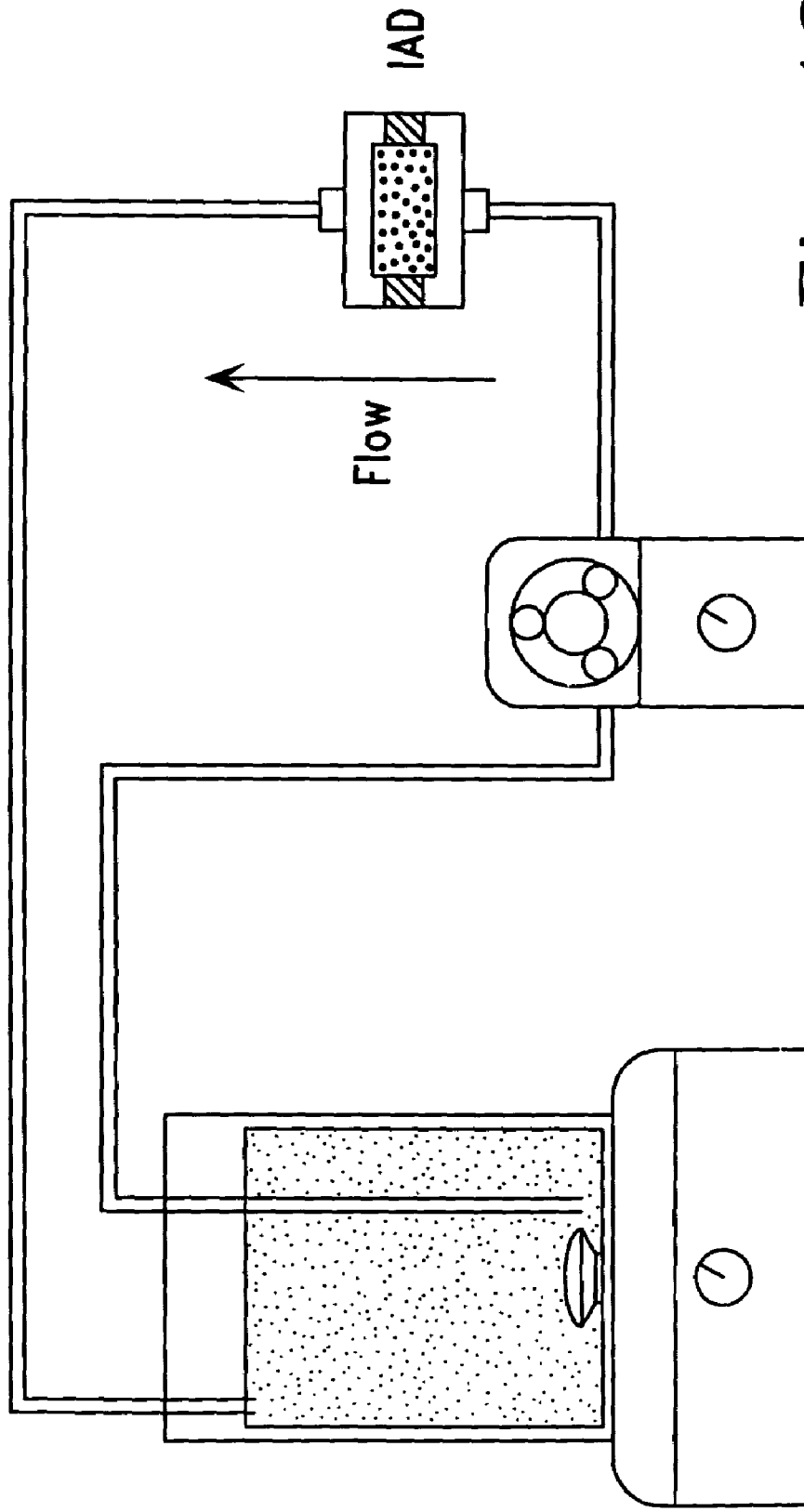
FIG. 13 is an illustration of an experimental set-up for a whole blood perfusion study.

The entire assembly was rinsed with a solution containing 174 USP units heparin (sodium salt, grade 1-A, 174 USP units/mg, Sigma Chemical Co.) per mL of saline. The saline was purged from the IAD assembly before introducing the whole blood. The unit of whole blood (500 mL) was added to the beaker. Agitation was slowly increased until mixing of the blood was apparent. The flow of whole blood was initiated. Whole blood was flowed from the bottom of the IAD up as indicated in FIG. 13. Samples of whold blood were taken from the beaker at 15 minute intervals. Cell counts were performed immediately using a Baker cell counter (manufacturer). Samples were centrifuged in a microcentrifuge (10,000 rpm, 5 min) and the supernatant was removed and immediately frozen for later analysis.

Samples of supernatant were thawed and were analyzed for residual levels of psoralen using reversed-phase HPLC. In addition, levels of activated complement fragment C3a were determined by using an ELISA (Quidel, San Diego, Calif.). Finally, levels of hemolysis were determined as described previously.

The results from the cell counts, hemolysis measurement, psoralen measurement, and C3a measurement are summarized in Table 3. In general, removal of both psoralen and C3a were demonstrated. In addition, whit blood cell (WBC) and red blood cell (RBC) counts remained essentially constant throughout the study. Platelets counts did show a downward trend during study and there was a slight increase in hemolysis. Further studies with fresh whole blood will be required to demonstrate whether losses in platelets could be attributed to the initial room temperature incubation that the whole blood was subjected to.

The advantages of using immobilized adsorbents in hemoperfusion devices include: 1) the ability to independently control adsorbent particle size and pressure drop-especially important at high flow rates or for small particle adsorbents; 2) the ability to control particle attrition by immobilizing the adsorbent particles thereby minimizing physical interactions; 3) the ability to minimize small particle contamination and shedding from the device by immobilizing adsorbent particles; 4) the ability to maintain a uniform and stable adsorbent bed.

TABLE 3

Results from Whole Blood Hemoperfusion Study.

| Time (min) | WBC Count ($\times 10^3$/μL) | RBC Count ($\times 10^6$/μL) | Platelet Count ($\times 10^3$/μL) | Hemolysis (%) | Residual Psoralen (μM) | Residual C3a (ng/mL) |
|---|---|---|---|---|---|---|
| 0 | 4.5 | 3.72 | 228 | 0.22 | 150.0 | 959 |
| 18 | 4.3 | 3.63 | 224 | 0.29 | 105.8 | 707 |
| 30 | 4.4 | 3.79 | 217 | 0.32 | 92.1 | 716 |
| 46.5 | 4.2 | 3.69 | 204 | 0.32 | 77.7 | 573 |
| 60 | 3.9 | 3.79 | 203 | 0.38 | 68.8 | 537 |
| 75 | 4.1 | 3.73 | 181 | 0.39 | 58.2 | 477 |
| 90 | 4.1 | 3.70 | 186 | 0.42 | 53.1 | 547 |

What is claimed is:

1. A pathogen-inactivating compound adsorption system for reducing the concentration of a low molecular weight pathogen-inactivating compound in a biological composition, wherein the pathogen-inactivating compound adsorption system comprises a housing compatible with the biological composition and containing an adsorption medium comprising adsorbent particles having a network pore structure immobilized within a sintered matrix formed from polymeric particulate material, wherein the diameter of the adsorbent particles ranges from about 1 μm to about 200 μm, wherein the adsorbent particles have an affinity for said pathogen-inactivating compound, wherein the system is configured to remove said pathogen-inactivating compound from said biological composition in a flow process, wherein the system is configured so that the biological composition treated with the system maintains sufficient biological activity so that said biological composition is suitable for infusion within a human.

2. A system according to claim 1, wherein the diameter of the adsorbent particles is between about 50 and 150 μm.

3. A system according to claim 1, wherein the particle containing matrix is at least 3 mm thick.

4. A system according to claim 1, wherein the adsorbent particles comprise adsorbent resin particles have a surface area greater than about 750 m²/g, and the porous adsorbent particles are between 30 and 70 percent of the weight of the adsorption medium.

5. A system according to claim 1, wherein the adsorbent particles comprise adsorbent resin particles having a surface area greater than about 750 m²/g.

6. A system according to claim 5, wherein the adsorbent resin particles are polyaromatic.

7. A system according to claim 6, wherein said adsorbent resin particles have a pore diameter between about 25 and 800 Å.

8. A system according to claim 7, wherein said adsorbent resin particles have a pore diameter between about 25 and 150 Å.

9. A system according to claim 8, wherein said adsorbent resin particles have a pore diameter between about 25 and 50 Å.

10. A system according to claim 5, wherein the adsorbent resin particles do not require prewetting before use.

11. A system according to claim 5, wherein the adsorbent resin particles are hypercrosslinked.

12. A system according to claim 1 or claim 5, wherein the pathogen inactivating compound comprises a nucleic acid-binding compound.

13. A system according to claim 12, wherein the nucleic acid-binding compound comprises a psoralen.

14. A system according to claim 12, wherein the nucleic acid-binding compound comprises an acridine derivative.

15. A system according to claim 12, wherein the nucleic acid-binding compound comprises a dye.

16. A system according to claim 12, wherein the adsorbent particles have an affinity for a nucleic acid-binding compound having an electrophilic group capable of reacting with a nucleophilic group of a quencher that quenches undesired side reactions of the pathogen-inactivating compound.

17. A system according to claim 16, wherein the adsorbent particles additionally have an affinity for said quencher.

18. A system according to claim 12, wherein the adsorbent particles additionally have an affinity for a degradation product of said nucleic acid-binding compound.

19. A system according to claim 1, wherein the adsorbent particles have an internal surface area between about 300 and 1100 $m^2/g$.

20. A system according to claim 1 or claim 5 wherein the sintered matrix comprises a polyolefin.

21. A system according to claim 20 wherein the polyolefin comprises polyethylene.

22. A system according to claim 21 wherein the polyethylene comprises an ultra high molecular weight polyethylene.

23. A system according to claim 1 wherein the adsorbent particles comprise activated carbon.

24. A system according to claim 23 wherein the activated carbon has a surface area greater than 950 m 2/g.

25. A system according to claim 24 wherein the activated carbon has a surface area greater than 1200 $m^2/g$.

26. A system according to claim 25 wherein the activated carbon has a surface area of about 2000 $m^2/g$.

27. A system according to claim 23 wherein the activated carbon is formed by steam activation of coconut shells.

28. A system according to claim 5 wherein said adsorbent particles comprise nonionic macroporous and macroreticular resin particles having macropores and micropores.

29. A method for reducing the concentration of a low molecular weight compound comprising a pathogen-inactivating compound in a biological composition, said method comprising treating the biological composition with a system of claim 1 or claim 5, to bind the low molecular weight compound to the adsorbent particles and thereby reduce the concentration of the low molecular weight compound in the biological composition, wherein the biological composition treated with the system maintains sufficient biological activity so that said biological composition is suitable for infusion within a human.

30. A method for reducing the concentration of a low molecular weight compound comprising a nucleic acid-binding compound in a biological composition, said method comprising treating the biological composition with a system of claim 12 to bind the low molecular weight compound to the adsorbent particles and thereby reduce the concentration of the low molecular weight compound in the biological composition, wherein the biological composition treated with the system maintains sufficient biological activity so that said biological composition is suitable for infusion within a human.

31. A method according to claim 30 wherein the nucleic acid-binding compound comprises an acridine derivative.

32. A method according to claim 31, wherein the acridine derivative comprises N-(9-acridinyl)-β-alanine.

33. A method according to claim 30, wherein the nucleic acid-binding compound comprises a dye.

34. A method according to claim 33, wherein the dye comprises methylene blue.

35. A method for reducing the concentration of a low molecular weight compound comprising a psoralen nucleic acid-binding compound in a biological composition, said method comprising treating the biological composition with a system of claim 12 to bind the low molecular weight compound to the adsorbent particles and thereby reduce the concentration of the low molecular weight compound in the biological composition, wherein the biological composition treated with the system maintains sufficient biological activity so that said biological composition is suitable for infusion within a human.

36. A method according to claim 35, wherein no more than about ten percent of an amount of said psoralen nucleic acid-binding compound originally added to said biological composition remains as free psoralen in said biological composition.

37. A method according to claim 35, wherein said psoralen nucleic acid-binding compound is selected from the group consisting of 4'-(4-amino-2-oxa)butyl-4,5',8-trimethyl psoralen, 8-methoxypsoralen, halogenated psoralens, isopsoralens and psoralens linked to quaternary amines, 5'-bromomethyl-4,4',8-trimethylpsoralen, 4'-bromomethyl-4,5',8-trimethylpsoralen, 4'-(4-amino-2-aza)butyl-4,5',8-trimethylpsoralen, 4'-(2-aminoethyl)-4,5',8-trimethylpsoralen, 4'-(5-amino-2-oxa)pentyl-4,5',8-trimethylpsoralen, 4'-(5-amino-2-aza)pentyl- 4,5',8-trimethylpsoralen, 4'-(6-amino-2-aza)hexyl-4,5',8-trimethylpsoralen, 4'-(7-amino-4,5',8-trimethylpsoralen, 4'-(12-amino-8-aza-2,5-dioxa)dodecyl-4,5', 8-trimethylpsoralen, 4'-(13-amino-2-aza-6,11-dioxa) tridecyl-4,5',8-trimethylpsoralen, 4'-(7-amino-2-aza)hep 4,5', 8-trimethylpsoralen, 4'-(7-amino-2-aza-5-oxa)heptyl-4, 5',8-trimethylpsoralen, 4'-(-amino-2,6-diaza)nonyl-4,5',8-trimethylpsoralen, 4'-(8-amino-5-aza-2-oxa)octyl-4,5'-(9-amino-5-aza-2-oxa)nonyl-4,5', 8-trimethylpsoralen, 4'-(14-amino-2,6,11-triaza)te 4,5',8-trimethylpsoralen, 5'-(4-amino-2-aza)butyl-4,4',8-trimeth 2-aza)hexyl-4,4',8-trimethylpsoralen and 5'-(4-amino-2-oxa)butyl-4,4',8-trimethylpsoralen.

38. A method according claim 35, wherein the biological composition comprises a blood product.

39. A method according to claim 38, wherein the blood product consists essentially of plasma.

40. A method according to claim 38, wherein the blood composition flows through the system as a result of a pressure differential which arises due to a hydrostatic head.

41. A method according to claim 38, wherein the blood composition flows through the system as a result of a pressure differential which arises due to the use of a pump.

42. A method according to claim 38, wherein the blood composition flows through the system at a flux between about 0.1 $mL/cm^2/min$ and about 10 $mL/cm^2/min$.

43. A method according to claim 42, wherein the blood composition flows through the system at a flux between about 0.2 $mL/cm^2/min$ and about 5 $mL/cm^2/min$.

44. A method according to claim 38, wherein the blood composition contains an original amount of factor XI, and said blood composition has at least about 91% of said original amount of factor XI after said treating with said system.

45. A method according to claim 38 wherein said blood product additionally contains activated complement and said adsorbent particles additionally bind the activated complement in said blood product.

* * * * *

UNITED STATES PATENT AND TRADEMARK OFFICE
CERTIFICATE OF CORRECTION

PATENT NO. : 6,951,713 B2  
APPLICATION NO. : 10/016323  
DATED : October 4, 2005  
INVENTOR(S) : Derek J. Hei et al.

It is certified that error appears in the above-identified patent and that said Letters Patent is hereby corrected as shown below:

Title page, item [54] Inventors: and Column 1,
replace "ABSORBING" with --ADSORBING--.

In the Claims:

In Claim 24, column 45, line 30, please replace "m 2/g" with --$m^2/g$--.

In Claim 37, column 46, starting on line 19 ending on line 40, please remove

"A method according to claim 35, wherein said psoralen nucleic acid-binding compound is selected from the group consisting of 4'-(4-amino-2-oxa)butyl-4,5',8-trimethyl psoralen , 8-methoxypsoralen, halogenated psoralens, isopsoralens and psoralens linked to quaternary amines, 5'-bromomethyl-4,4',8-trimethylpsoralen, 4'-bromomethyl-4,5',8-trimethylpsoralen, 4'-(4-amino-2-aza)butyl-4,5',8-trimethylpsoralen, 4'-(2-aminoethyl)-4,5',8-trimethylpsoralen, 4'-(5-amino-2-oxa)pentyl-4,5',8-trimethylpsoralen, 4'-(5-amino-2-aza)pentyl-4,5',8-trimethylpsoralen, 4'-(6-amino-2-aza)hexyl-4,5',8-trimethylpsoralen, 4'-(7-amino-4,5',8-trimethylpsoralen, 4'-(12-amino-8-aza-2,5-dioxa)dodecyl-4,5',8-trimethylpsoralen, 4'-(13-amino-2-aza-6,11-dioxa)tridecyl-4,5',8-trimethylpsoralen, 4'-(7-amino-2-aza)heptyl-4,5', 8-trimethylpsoralen, 4'-(7-amino-2-aza-5-oxa)hep4,5',8-trimethylpsoralen, 4'-(-amino-2,6-diaza)nonyl-4,5',8-trimethylpsoralen, 4'-(8-amino-5-aza-2-oxa)octyl-4,5'-(9-amino-5-aza-2-oxa)nonyl-4,5',8-trimethylpsoralen, 4'-(14-amino-2,6,11-triaza)te   4,5',8-trimethylpsoralen, 5'-(4-amino-2-aza)butyl-4,4',8-trimeth    2-aza)hexyl-4,4',8-trimethylpsoralen and 5'-(4-amino-2-oxa)butyl-4,4',8-trimethylpsoralen."

UNITED STATES PATENT AND TRADEMARK OFFICE
CERTIFICATE OF CORRECTION

PATENT NO. : 6,951,713 B2
APPLICATION NO. : 10/016323
DATED : October 4, 2005
INVENTOR(S) : Derek J. Hei et al.

It is certified that error appears in the above-identified patent and that said Letters Patent is hereby corrected as shown below:

and replace with

--A method according to claim 35, wherein said psoralen nucleic acid-binding compound is selected from the group consisting of 4'-(4-amino-2-oxa)butyl-4,5',8-trimethyl psoralen , 8-methoxypsoralen, halogenated psoralens, isopsoralens and psoralens linked to quaternary amines, 5'-bromomethyl-4,4',8-trimethylpsoralen, 4'-bromomethyl-4,5',8-trimethylpsoralen, 4'-(4-amino-2-aza)butyl-4,5',8-trimethylpsoralen, 4'-(2-aminoethyl)-4,5',8-trimethylpsoralen, 4'-(5-amino-2-oxa)pentyl-4,5',8-trimethylpsoralen, 4'-(5-amino-2-aza)pentyl-4,5',8-trimethylpsoralen, 4'-(6-amino-2-aza)hexyl-4,5',8-trimethylpsoralen, 4'-(7-amino-2,5-oxa)heptyl-4,5',8-trimethylpsoralen, 4'-(12-amino-8-aza-2,5-dioxa)dodecyl-4,5',8-trimethylpsoralen, 4'-(13-amino-2-aza-6,11-dioxa)tridecyl-4,5',8-trimethylpsoralen, 4'-(7-amino-2-aza)heptyl-4,5', 8-trimethylpsoralen, 4'-(7-amino-2-aza-5-oxa)heptyl-4,5',8-trimethylpsoralen, 4'-(9-amino-2,6-diaza)nonyl-4,5',8-trimethylpsoralen, 4'-(8-amino-5-aza-2-oxa)octyl-4,5',8-trimethylpsoralen, 4'-(9-amino-5-aza-2-oxa)nonyl-4,5',8-trimethylpsoralen, 4'-(14-amino-2,6,11-triaza)tetradecyl-4,5',8-trimethylpsoralen, 5'-(4-amino-2-aza)butyl-4,4',8-trimethylpsoralen, 5'-(6-amino-2-aza)hexyl-4,4',8-trimethylpsoralen and 5'-(4-amino-2-oxa)butyl-4,4',8-trimethylpsoralen.--

Signed and Sealed this

Fifteenth Day of August, 2006

JON W. DUDAS
*Director of the United States Patent and Trademark Office*